(12) United States Patent
Tagmose et al.

(10) Patent No.: US 9,480,753 B2
(45) Date of Patent: Nov. 1, 2016

(54) FGF21 DERIVATIVES WITH ALBUMIN BINDER A-B-C-D-E- AND THEIR USE

(75) Inventors: Tina Møller Tagmose, Ballerup (DK); Patrick William Garibay, Holte (DK); Birgitte Andersen, Malov (DK); Henning Thøgersen, Farum (DK); Birgit Wieczorek, Koebenhavn N (DK)

(73) Assignee: Novo Nordisk A/S, Bagsvaerd (DK)

( * ) Notice: Subject to any disclaimer, the term of this patent is extended or adjusted under 35 U.S.C. 154(b) by 880 days.

(21) Appl. No.: 12/692,227

(22) Filed: Jan. 22, 2010

(65) Prior Publication Data

US 2010/0216715 A1    Aug. 26, 2010

Related U.S. Application Data

(60) Provisional application No. 61/151,355, filed on Feb. 10, 2009, provisional application No. 61/151,357, filed on Feb. 10, 2009, provisional application No. 61/225,387, filed on Jul. 14, 2009.

(30) Foreign Application Priority Data

| Jan. 23, 2009 | (EP) | 09151227 |
| Feb. 5, 2009 | (EP) | 09152144 |
| Jul. 8, 2009 | (EP) | 09164904 |

(51) Int. Cl.

| A01N 43/64 | (2006.01) |
| A61K 31/41 | (2006.01) |
| A01N 43/36 | (2006.01) |
| A61K 31/40 | (2006.01) |
| A01N 37/00 | (2006.01) |
| A61K 31/19 | (2006.01) |
| A61K 47/48 | (2006.01) |
| C07K 14/50 | (2006.01) |
| A61K 38/00 | (2006.01) |

(52) U.S. Cl.
CPC ... *A61K 47/48046* (2013.01); *A61K 47/48215* (2013.01); *A61K 47/48284* (2013.01); *C07K 14/50* (2013.01); *A61K 38/00* (2013.01)

(58) Field of Classification Search
None
See application file for complete search history.

(56) References Cited

U.S. PATENT DOCUMENTS

| 5,424,286 A | 6/1995 | Eng |
| 2012/0035099 A1 | 2/2012 | Garibay et al. |

FOREIGN PATENT DOCUMENTS

| CN | 101250547 | 8/2008 |
| JP | 2008507477 | 3/2008 |
| WO | 98/08871 | 3/1998 |
| WO | WO 03/011213 | 2/2003 |
| WO | WO 03/061712 | 7/2003 |
| WO | WO 2005/027978 | 3/2005 |
| WO | WO 2005/028516 | 3/2005 |
| WO | WO 2005/058958 | 6/2005 |
| WO | WO 2005/061712 | 7/2005 |
| WO | WO 2005/091944 | 10/2005 |
| WO | WO 2005/113606 | 12/2005 |
| WO | WO 2005/117984 | 12/2005 |
| WO | WO 2006/028595 | 3/2006 |
| WO | WO 2006/028714 | 3/2006 |
| WO | WO 2006/050247 | 5/2006 |
| WO | WO 2006/065582 | 6/2006 |
| WO | WO 2006/078463 | 7/2006 |
| WO | 2006/097537 | 9/2006 |
| WO | WO 2008/087190 | 7/2008 |
| WO | WO 2008/121563 | 10/2008 |
| WO | 2009/020802 A2 | 2/2009 |
| WO | 2009/030771 A1 | 3/2009 |
| WO | 2010/042747 A2 | 4/2010 |
| WO | 2010/065439 A1 | 6/2010 |
| WO | 2010/084169 A2 | 7/2010 |
| WO | 2010/142665 A1 | 12/2010 |

OTHER PUBLICATIONS

Yie et al., "FGF21 N- and C-termini play different roles in receptor interaction and activation," FEBS Letters, 583 (2009), 19-24.
Knudsen, L.B., Journal of Medicinal Chemistry, "Glucagon-like Peptide-1: The Basis of a New Class of Treatment for Type 2 Diabetes", 2004, vol. 47, No. 17, pp. 4128-4134.
Nauck, M.A et al., Regulatory Peptides, "Glucagon-like Peptide 1 and . . . ", 2005, vol. 128, No. 2, pp. 135-148.
CN Abstract 101250547.
Coskun, T. et al., "Fibroblast Growth Factor 21 Corrects Obesity in Mice", Endocrinology, 2008, vol. 149, No. 12, pp. 6018-6027.
Dennis, M.S. et al., "Albumin Binding as a General Strategy for Improving the Pharmacokinetics of Proteins", The Journal of Biological Chemistry, 2002, vol. 277, No. 38, pp. 35035-35043.
Erickson et al., Journal of Lipid Research, 2009, pp. S412-S416.
Grundy, S.M. et al., "Definition of Metabolic Syndrome", Circulation, 2004, vol. 109, pp. 433-438.

(Continued)

*Primary Examiner* — Jeffrey S Lundgren
*Assistant Examiner* — Stephanie Springer
(74) *Attorney, Agent, or Firm* — Nonna G. Akopyan

(57) ABSTRACT

The present invention relates to Fibroblast Growth Factor 21 (FGF21), more in particular to derivatives of FGF21 compounds having an albumin binder of the formula A-B-C-D-E- covalently attached. The invention also relates to novel FGF21 analogues, as well as to the pharmaceutical use of these FGF21 derivatives and analogues, in particular for the treatment of diabetes, dyslipidemia, obesity, cardiovascular diseases, metabolic syndrome, and/or Non Alcoholic Fatty Liver Disease (NAFLD). The derivatives of the invention are protracted, e.g. capable of maintaining a low blood glucose level for a longer period of time, capable of increasing the in vivo half-life of FGF21, and/or result in a lower clearance of FGF21. The derivatives of the invention are preferably furthermore of an improved oxidative stability.

10 Claims, No Drawings

(56) References Cited

OTHER PUBLICATIONS

Kharitonenkov, A. et al., "The Metabolic State of Diabetic Monkeys is Regulated by Fibroblast Growth Factor-21", Endocrinology, 2007, vol. 148, No. 2, pp. 774-781.
Kharitonenkov, A. et al., "FGF-21 as a Novel Metabolic Regulator", The Journal of Clinical Investigation, 2005, vol. 115, No. 6, pp. 1627-1635.
Kratz, F., "Albumin as a Drug Carrier: Design of Prodrugs, Drug Conjugates and Nanoparticles", Journal of Controlled Release, 2008, vol. 132, No. 3, pp. 171-183.
Xu, J. et al., "Fibroblast Growth Factor 21 Reverses Ilepatic Steatosis, Increases Energy Expenditure, and Improves Insulin Sensitivity in Diet-Induced Obese Mice", Diabetes, 2009, vol. 58, No. 1, pp. 250-259.
Micanovic et al., Journal of Cellular Physiology, "Different Roles of N- and C- Termini in the Functional Activity of FGF21", , Wiley Liss, New York, NY, US, vol. 219, No. 2, May 1, 2009, pp. 227-234.
Kharitonenkov A et al. "Fibroblast growth factor-21 as a therapeutic agent for metabolic diseases." BioDrugs 2008 vol. 22(1): 37-44.
Makrides S C et al: "Extended in vivo half-life of Human Soluble Complement Receptor Type 1 Fused to a Serum Albumin-Binding Receptor", Journal of Pharmacology and Experimental Therapeutics, 1996 American Society for Pharmacology and Experimental Therapeutics, vol. 277, No. 1, pp. 534-542.
Sjolander a et al: "The serum albumin-binding region of streptococcal protein G: a bacterial fusion partner with carrier-related properties", 1997 Journal of Immunological Methods, vol. 201, No. 1, pp. 115-123.
Kurtzhals p. et al: "Albumin Binding of Insulins Acylated With Fatty Acids: Characterization of the Ligand-Protein Interaction and Correlation Between Binding Affinity and Timing of the Insulin Effect in Vivo", Biochemical Journal, 1995 vol. 312, No. 3, pp. 725-731.

FGF21 DERIVATIVES WITH ALBUMIN BINDER A-B-C-D-E- AND THEIR USE

CROSS-REFERENCE TO RELATED APPLICATIONS

This application is a utility application which claims priority under 35 U.S.C. §119 of U.S. Provisional Application 61/151,355, filed Feb. 10, 2009; U.S. Provisional Application 61/151,357, filed Feb. 10, 2009; and U.S. Provisional Application 61/225,387, filed Jul. 14, 2009; this application further claims priority of European Application 09151227.7, filed Jan. 23, 2009; European Application 09152144.3, filed Feb. 5, 2009; and European Application 09164904.6, filed Jul. 8, 2009.

FIELD OF THE INVENTION

The present invention relates to Fibroblast Growth Factor 21 (FGF21), more in particular to derivatives of FGF21 compounds having an albumin binder of the formula A-B-C-D-E- covalently attached. The invention also relates to novel FGF21 analogues, as well as to the pharmaceutical use of these FGF21 derivatives and analogues, in particular for the treatment of diabetes, dyslipidemia, obesity, cardiovascular diseases, metabolic syndrome, and/or Non Alcoholic Fatty Liver Disease (NAFLD).

The derivatives of the invention are protracted, e.g. capable of maintaining a low blood glucose level for a longer period of time, capable of increasing the in vivo half-life of FGF21, and/or result in a lower clearance of FGF21. The derivatives of the invention are preferably furthermore of an improved oxidative stability.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jan. 22, 2010. The Sequence Listing is made up of 43 bytes, and the information contained in the attached "SEQUENCE LISTING" is identical to the information in the specification as originally filed. No new matter is added.

BACKGROUND OF THE INVENTION

Fibroblast growth factors are polypeptides expressed in developing and adult tissues. They are involved in several physiological mechanisms including for example metabolic regulation and cellular differentiation. A whole family of more than twenty fibroblast growth factors exists (the FGF family). Three members of the FGF family including FGF19, FGF21, and FGF23 form a subfamily functioning as endocrine factors involved in metabolic regulation.

Fibroblast Growth Factor 21 or FGF-21, herein for short FGF21, is expressed preferentially in the liver and has been shown to exert hormone-like metabolic effects.

For example, FGF21 has been demonstrated to activate glucose uptake in mouse adipocytes, to protect mice from diet induced obesity when over-expressed in transgenic mice, and to lower blood glucose and triglyceride levels when administered to diabetic rodents (Kharitonenkov et al., *J. Clin. Invest*. (2005), 115:1627-1635).

The lowering effect of FGF21 on blood glucose and triglycerides has also been shown in diabetic monkeys. FGF21 was also able to decrease LDL and to increase HDL significantly in diabetic monkeys (Kharitonenkov et al., *Endocrinology* (2007), 148(2):774-81).

In diet induced obese mice and ob/ob mice, FGF21 was furthermore shown to lower body weight, predominantly by an increase in energy expenditure and a reduction in adiposity (Coskun et al., *Endocrinology* (2008), 149(12): 6018-6027).

Based on these results FGF21 has been suggested as a pharmacological agent with the potential to treat diabetes, dyslipidemia, obesity, cardiovascular diseases, and metabolic syndrome. Metabolic syndrome includes aspects like insulin resistance, dyslipidemia, visceral obesity and hypertension, see e.g. the definition of metabolic syndrome in Grundy et al., *Circulation* (2004), (109): 433-438.

FGF21 may furthermore be used as a pharmacological agent with a potential to treat Non Alcoholic Fatty Liver Disease (NAFLD), see Coskun et al. *Endocrinology*, 2008 cited above, and Xu et al., *Diabetes* (2009, 58(1):250-9, published electronically 7 Oct. 2008 ahead of print). NAFLD has been defined by Erickson, *J. Lipid Res*. (2008), published electronically 12 Dec. 2008 ahead of print.

Yie et al. studied the role of the N- and C-termini of FGF21 in receptor interaction and activation, see *FEBS Letters*, 583 (2009), 19-24.

WO 2003/011213 A2 discloses a method for treating diabetes of type 1 and 2, or obesity, by use of FGF21 compounds with at least 95% identity to the FGF21 precursor amino acid sequence.

WO 2003/061712 A1 discloses muteins of FGF21 with improved pharmaceutical properties, e.g. A145E.

WO 2005/091944 A2 discloses PEGylated derivatives of FGF21, FGF21-K59C, and FGF21-K122C.

WO 2005/113606 A2 discloses various FGF21 fusion proteins with the Fc portion of an IgG4 immunoglobulin, or human serum albumin.

WO 2006/028595 A2 discloses further muteins of FGF21 with reduced capacity of O-glycosylation when expressed in yeast, e.g. L118C-A134C-S167A.

WO 2006/028714 A1 discloses additional muteins of FGF21 with reduced susceptibility for proteolytic degradation when expressed in yeast, e.g. L153I.

WO 2006/065582 A2 discloses still further muteins of FGF21 with reduced deamidation, e.g. des-HPIP-L118C-A134C-N121D.

WO 2006/078463 A2 discloses a method for treating cardiovascular disease by use of native mature FGF21 or specified variants thereof.

WO 2008/121563 discloses FGF21 polypeptides modified to include non-naturally encoded amino acids, as well as derivatives thereof.

SUMMARY OF THE INVENTION

Briefly, this invention is as defined in claim 1 below.

The present invention relates to derivatives of FGF21 compounds having an albumin binder covalently attached to the FGF21 compound, wherein the albumin binder has the formula A-B-C-D-E-, in which component A is a fatty acid or a derivative thereof. The invention also relates to novel FGF21 analogues, as well as the use of the derivatives and analogues of the invention in pharmaceutical compositions, in particular for the treatment of diabetes, dyslipidemia, obesity, cardiovascular diseases, metabolic syndrome, and/or Non Alcoholic Fatty Liver Disease (NAFLD).

The derivatives of the invention are protracted, e.g. capable of maintaining a low blood glucose level for a longer period of time, capable of increasing the in vivo half-life of FGF21, and/or result in a lower clearance of FGF21. The protracted FGF21 derivatives retain satisfactory biological activity and may be administered less frequently. The derivatives are preferably furthermore of an improved oxidative stability.

DETAILED DESCRIPTION OF THE INVENTION

The present invention relates to derivatives of an FGF21 compound having an albumin binder of the formula A-B-C-D-E- covalently attached, wherein A- is an element of formula I, II or III:

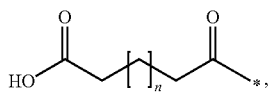
(formula I)

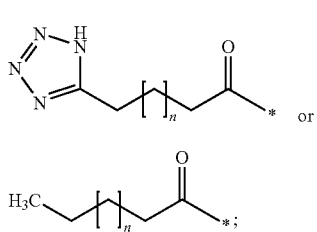
(formula II)

or (formula III)

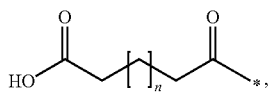

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

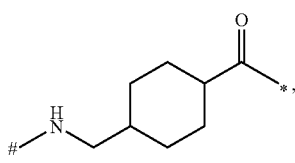
(formula IV or Trx)

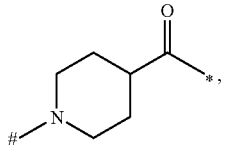
(formula V or Inp)

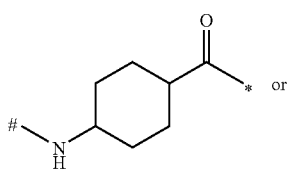
(formula VI)

or

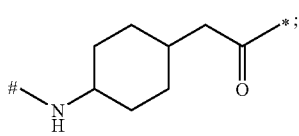
(formula VII)

wherein * is the point of attachment to -B2- or -C-, and # is the point of attachment to A- or -B2-; and -B2- is an element of formula IIX, IX or XXVIII or a combination of up to four elements of formula IIX and/or formula IX and/or formula XVIII:

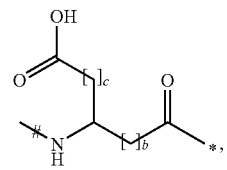
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

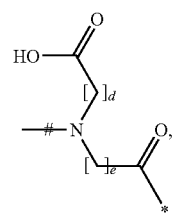
(formula IX)

wherein d is 1 or 2, e is 0, 1 or 2, * is the point of attachment to -C- or -B1-, and # is the point of attachment to A- or -B1-; or

—NH—SO$_2$—(CH$_2$)$_u$—CO—*   (formula XXVIII)

wherein u is 2, 3 or 4, * is the point of attachment to -C- or -B1-, and # is the point of attachment to A- or -B1-;

-C- is absent, represents a bond or is an element of formula X or XI:

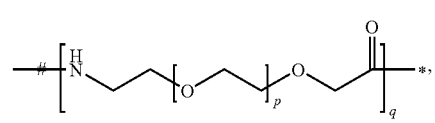
(formula X)

wherein p is 0, 1, 2, 3, 4, 5 or 6, q is 0, 1, 2, 3, 4, 5 or 6, * is the point of attachment to -D-, -E- or the FGF21 compound, and # is the point of attachment to -B-; or

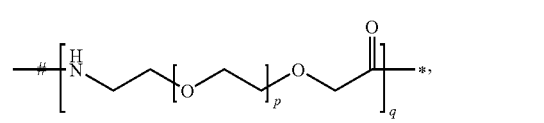
(formula XI)

wherein k is 0, 1, 2, 3, 4, 5, 11 or 23, m is 0, 1, 2, 3, 4, 5 or 6, * is the point of attachment to -D-, -E- or the FGF21 compound; and # is the point of attachment to -B-;

-D- is absent, represents a bond or is an element of formula XII or XIII:

—NH—(CH$_2$)$_r$—NH—CO—(CH$_2$)$_s$—*   (formula XII) or

—NH—(CH$_2$)$_t$—*   (formula XIII), wherein r is 2, 3, 4 or 5, s is 1, 2, 3 or 4, t is 1, 2, 3, 4, 5 or 6, * is the point of attachment to -E- or the FGF21 compound, and # is the point of attachment to -C-;

-E- is absent, represents a bond or is an element of formula XXII, XXIII, XXIIIa, XXIV, XXIVa, XXV, XXVI or XXVII:

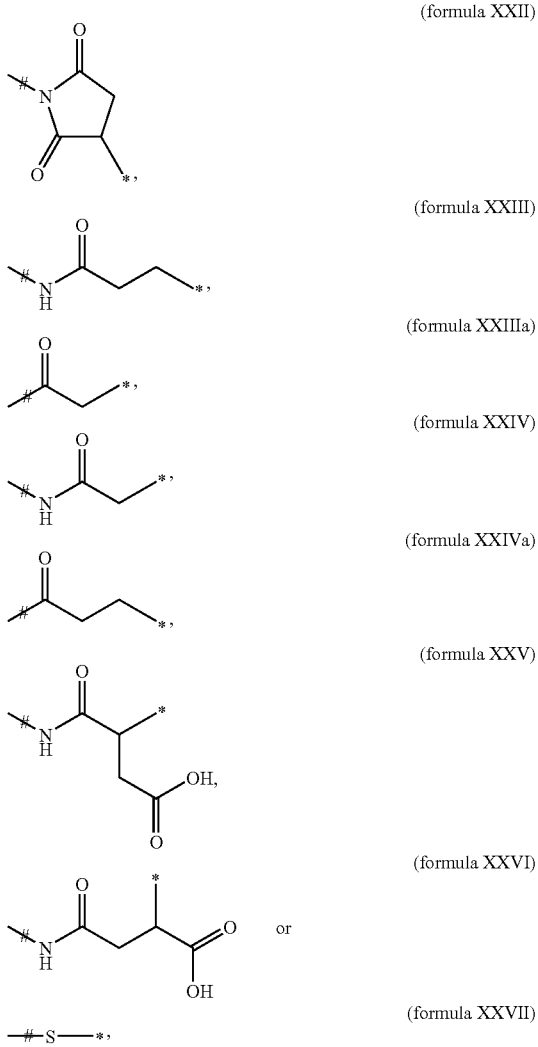

wherein * is the point of attachment to the FGF21 compound, and # is the point of attachment to -D- or -C-;
or a pharmaceutically acceptable salt thereof.

The invention also relates to novel FGF21 analogues comprising (a) at least one of the following modifications as compared to SEQ ID NO:1: −1G, −1C, −1S, S6C, S6K, A26E, Q27E, Q28R, A31E, K56R, K59R, K69R, S71C, D102T, K122R, I152K, L166F, S167G, M168L, V169aT, P171L, S172E, Q173A, G174V, Y179F, A180E, and/or S181K,R; independently optionally with an N-terminal M (e.g., −1M); and/or (b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S. SEQ ID NO:1 is the mature wild type human FGF21 peptide having 181 amino acid residues.

Finally, the invention relates to pharmaceutical compositions comprising a therapeutically effective amount of the analogues or derivatives of the invention, and a pharmaceutically acceptable carrier; as well as to methods for treating a patient exhibiting diabetes, dyslipidemia, obesity, cardiovascular diseases, metabolic syndrome, and/or Non Alcoholic Fatty Liver Disease (NAFLD) comprising administering to the patient a therapeutically effective amount of an analogue, derivative or composition of the invention.

In a first aspect, the derivative of the invention has an albumin binder of the formula A-B-C-D-E- covalently attached to a thiol group of the FGF21 compound, i.e. to a cysteine residue.

In a second aspect, the derivative of the invention has an albumin binder of the formula A-B-C- covalently attached to an amino group of the FGF21 compound, which can be the N-terminal amino group, and/or an internal amino group such as the epsilon-amino group of a lysine residue.

The derivatives of this invention and the analogues of this invention shall have biological effect similar to that of FGF21, for example, in relation to glucose lowering effect, improvement in dyslipidemia, obesity, cardiovascular diseases, metabolic syndrome, and/or Non Alcoholic Fatty Liver Disease (NAFLD)

DEFINITIONS

The term "FGF21 compound" as used herein refers to native human FGF21 as well as analogues thereof.

The sequence of the native human FGF21 protein is available from the UNIPROT database with accession no. Q9NSA1. The 209 amino acid precursor protein includes a signal peptide (amino acids 1-28) and a mature protein (amino acids 29-209). The mature protein is included herein as SEQ ID NO:1 (amino acids 1-181), and the signal peptide as SEQ ID NO:2 (amino acids 1-28).

An isoform or allelic form of native human FGF21 having a Pro instead of Leu in the mature protein at position 146 of SEQ ID NO:1 herein is known from, i.a., US2001012628 A1 (residue no. 174 of SEQ ID NO:2 in the published US application).

Another isoform having a shorter signal peptide in which Leu at position 23 of SEQ ID NO:2 herein is missing is known from WO 2003/011213 (see SEQ ID NO: 2 of the WO publication having a signal peptide of 27 amino acid residues).

Thus, particular examples of native human FGF21 are: SEQ ID NO:1, SEQ ID NO:1 having the substitution L146P, as well as any of these sequences preceded by the 27 or 28 amino acids signal peptide referred to above. Preferred examples of native human FGF21 are the mature parts, viz. SEQ ID NO:1 and the L146P isoform thereof.

The term "analogue" as referred to herein in the context of FGF21, i.e., an FGF21 analogue, refers to polypeptides that are or can be, deduced or derived from native FGF21, from SEQ ID NO:1 in particular, by modification of the amino acid sequence thereof. Such modification, amendment or change may include substitution, deletion, and/or addition of one or more amino acids. For example, amino acids may be added and/or deleted at the C-terminus, at the N-terminus, or internally in the amino acid sequence. Preferably amino acids are added and/or deleted at the C- and/or N-terminus, more preferably at the N-terminus. Amino acid sequences with C- or N-terminally deleted amino acids may also be referred to as truncated sequences, as is known in the art. Likewise, amino acids added internally in the sequence may be referred to as insertions. The term "variant" or "mutein" is now and then used herein instead of the term "analogue".

One example of an FGF21 analogue is the truncated form of native mature FGF21 in which the four N-terminal amino acid residues of the mature protein (HPIP) are removed, which is disclosed in, e.g., WO 2006/065582. This truncated form is said to stimulate glucose uptake in mouse 3T3-L1 adipocytes at the same level as the wild-type FGF21. This protein has the amino acid sequence of amino acids 5-181 of SEQ ID NO:1 herein.

A further example of an FGF21 analogue is the polypeptide of SEQ ID NO:1 which has an N-terminal Met (also designated "Met-FGF21" or as substitution −1M ((minus 1)M) of SEQ ID NO:1). An N-terminal Met is added when FGF21 compound is expressed in *E. coli*, see e.g. WO 2006/050247, Table 6.

Other examples of FGF21 analogues are the modified FGF21 sequences (often called muteins) which are disclosed in e.g. WO 2003/061712, WO 2005/091944, WO 2006/028595, WO 2006/028714, WO 2006/065582 and WO 2008/121563 (cf. the background art section herein).

Still further examples of FGF21 analogues are disclosed in the experimental part herein, as well as in the appended claims.

The term "amino acid" or "amino acid residue" as referred to herein in the context of FGF21 modifications includes the twenty standard alpha-amino acids being used by cells in protein biosynthesis and specified by the genetic code, viz. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The term also includes non-standard amino acids, such as selenocysteine and pyrrolysine which are also encoded by the genetic code but rare in proteins. Other non-standard amino acids found in proteins may be formed by post-translational modification, for example γ-carboxy-glutamate and hydroxyproline. Additional examples of non-standard or non-natural amino acids which are not encoded by the genetic code are ornithine and phosphoserine. Still further examples of non-standard amino acids are synthetic amino acids including amino acids manufactured by chemical synthesis, e.g. D-isomers of the amino acids encoded by the genetic code such as D-alanine, D-glutamine, D-histidine, and D-leucine, Aib (α-amino-isobutyric acid), Abu (α-aminobutyric acid), Tle (tert-butylglycine), β-alanine, 3-aminomethyl benzoic acid, anthranilic acid, des-amino-histidine (abbreviated DesaminoHis, alternative name imidazopropionic acid, abbreviated Impr), the beta analogues of amino acids such as β-alanine, 2-amino-histidine, β-hydroxy-histidine, homohistidine, Nα-acetyl-histidine, α-fluoro-methyl-histidine, α-methyl-histidine, α,α-dimethyl-glutamic acid, m-CF$_3$-phenylalanine (abbreviated m-CF$_3$-Phe), α,β-diaminopropionic acid (abbreviated Dap), 3-pyridylalanine, 2-pyridylalanine or 4-pyridylalanine, (1-aminocyclopropyl)carboxylic acid, (1-aminocyclobutyl)-carboxylic acid, (1-aminocyclopentyl)carboxylic acid, (1-aminocyclohexyl)carboxylic acid, (1-aminocycloheptyl)carboxylic acid, and (1-aminocyclooctyl)carboxylic acid.

For the present purposes the two recognized codes of the standard amino acids (one-letter and three-letter) are used interchangeably, or now and then the amino acid name is fully spelled out. These terms are of course considered fully equivalent (e.g. S=Ser=serine).

The term "derivative" as used herein refers to an FGF21 compound which has been covalently modified. The term is not limiting as such, rather descriptive, as it is intended to mark a distinction between changes made to the constituent FGF21 polypeptide compound as such ("analogues"), and the covalent binding of a side chain to the FGF21 compound, whereby the compound is "derivatised". If desired, this term can be substituted with other general chemical terms, for example compound.

The term "albumin binder" is also not intended to be limiting as such. Again, it is rather descriptive, as it reflects the overall aim or purpose of attaching the A-B-C-D-E-chain to the FGF21 compound, viz. that the resulting compound (derivative) is capable of binding to human serum albumin which provides or at least contributes to the protracted effect aimed at for the derivatives of the invention. If desired, this term can also be substituted with other general chemical terms, for example compound.

Nomenclature: Analogues and derivatives are named herein using, interchangeably, polypeptide nomenclature, organic chemical nomenclature, and chemical formulas, or mixtures thereof, whatever is deemed best suited for easing the understanding of the technical matter in question. For example, the derivative of Example 4 may be named S-122-[1-(2-{2-[2-(2-{2-[2-(2-{2-[(S)-4-carboxy-4-(17-carboxy-heptadeconoylamino)-butyrylamino]-ethoxy}-ethoxy)-acetylamino]-ethoxy}-ethoxy)-acetylamino]-ethylcarbamoyl}-ethyl)-2,5-dioxo-pyrrolidin-3-yl] [Cys122]-Met-FGF21 (meaning that [Cys122] Met-FGF21 is modified by 1-(2-{2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-ethyl)-2,5-dioxo-pyrrolidin-3-yl at the thiol group in Cys in position 122). But this compound may also be defined as K122C Met-FGF21, derivatised at C122 with the followings compound:

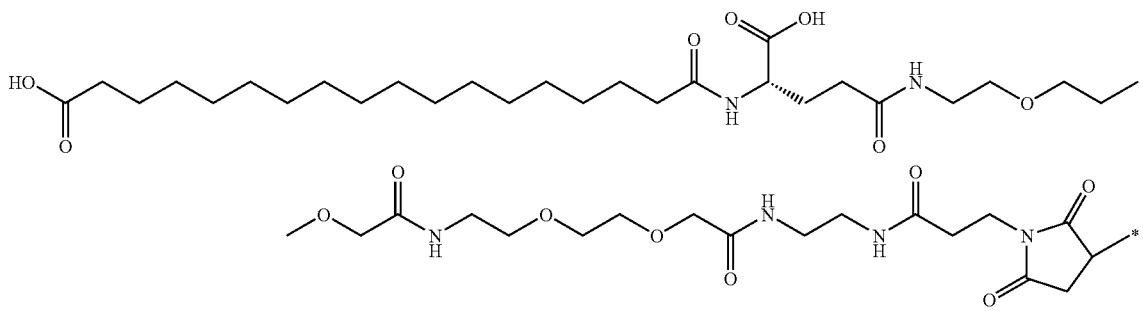

Variant nomenclature (Nomenclature of analogues): Variants (or analogues) of FGF21 are named herein using, interchangeably, polypeptide nomenclature, organic chemical nomenclature, chemical formulas, amino acid sequences, or a mix thereof, whatever is deemed best suited for easing the understanding of the technical matter in question.

For example, a substitution in a variant may be indicated as: "Original amino acid-position-substituted amino acid". The three or one letter code may be used. Accordingly, the notation "K122C" or "Lys122Cys" means, that the variant comprises a substitution of lysine with cysteine in the variant amino acid position corresponding to the amino acid at position 122 in FGF21 (SEQ ID NO:1), when the variant and FGF21 are aligned as described further below ("alignment").

Multiple modifications such as e.g. substitutions may be separated by commas (with a space after the comma), and if desired surrounded by brackets in order to make it clear that they belong to the same variant. The analogue which is derivatised in Example 7 may for example be designated "K56R, K59R, K69R, K122R Met-FGF21" or "(K56R, K59R, K69R, K122R) Met-FGF21" or it may be referred to as "SEQ ID NO:1 with K56R, K59R, K69R, and K122R and an N-terminal M". See Compound Y of Example 2 for the nomenclature of a variant with multiple modifications in the form of a mix of substitutions and insertions.

Alternative modifications such as alternative substituents at a given position may be separated by commas, as e.g. in the designation "S181K,R", which means that the Ser at position 181 may be substituted with Lys or Arg.

An extension can be described by reference to SEQ ID NO:1 by addition of position numbers (continued positive numbers in the C-terminal end and negative numbers in the N-terminal end) or, more simply, by adding the amino acids of the extension in question, using the correct sequence thereof, to the compound in question, which is then often given a trivial name, such as FGF21, again in order to ease the understanding of the relevant technical point. As an example the compound (s) MGGGGG-FGF21 designates the polypeptide of SEQ ID NO:1 (FGF21) with a G at position −1, a G at position −2, a G at position −3, a G at position −4, a G at position −5, and an M at position −6, by reference to SEQ ID NO:1. Likewise, the compound (q) MS-FGF21 (or Met-Ser-FGF21) designates the polypeptide of SEQ ID NO:1 (FGF21) with an S at position −1, and an M at position −2, by reference to SEQ ID NO:1.

An insertion in a variant may be indicated as: "Amino acid position number before the insertion-index-inserted amino acid". The amino acid position number before the insertion refers to the amino acid position in FGF21 (SEQ ID NO:1) just before the gap, which is created when the variant and FGF21 are aligned as described further below ("alignment"). For the amino acids, the three or one letter code may be used. The index is a lower case letter in alphabetical order, e.g. "a" for the first inserted amino acid residue, "b" for the second inserted amino acid residue, etc., as applicable. Accordingly, the notation"V169aT" (or "Val169aThr") or simply "169aT" (or "169aThr") all mean, that the variant comprises an insertion of threonine after valine at position 169 in FGF21 (SEQ ID NO:1), when the variant and FGF21 are aligned as described further below ("alignment").

In cases where there is an extra disulphide bridge in the FGF compound, the two Cys are typed adjacent to each other and connected by a dash, as, e.g., in "L118C-A134C", where there is a disulphide bridge between the Cys in position 118 and the Cys in position 134.

For purposes of the present invention, the alignment of two amino acid sequences may be made using the Needle program from the EMBOSS package (http://emboss.org). A preferred version is 2.8.0. The Needle program implements the global alignment algorithm described in Needleman, S. B. and Wunsch, C. D. (1970) *J. Mol. Biol.* 48, 443-453. The substitution matrix used is BLOSUM62, gap opening penalty is 10, and gap extension penalty is 0.5.

The degree or percentage of identity between an FGF21 analogue sequence of the present invention ("invention sequence"; e.g. SEQ ID NO:1 with K56R, K59R, and K69R) and a different amino acid sequence ("foreign sequence"; e.g. the FGF21 sequence of SEQ ID NO:1) is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "*"). The length of a sequence is the number of amino acid residues in the sequence (e.g. the length of SEQ ID NO:1 is 181).

This is an example of an alignment of the "invention sequence" and the "foreign sequence" that are referred to above:

```
FGF21_SEQ1   HPIPDSSPLLQFGGQVRQRYLYTDDAQQTEAHLEIREDGTVGGAADQSPESLLQLKALKP
56_59_69R    HPIPDSSPLLQFGGQVRQRYLYTDDAQQTEAHLEIREDGTVGGAADQSPESLLQLRALRP
             ********************************************************.**.*

FGF21_SEQ1   GVIQILGVKTSRFLCQRPDGALYGSLHFDPEACSFRELLLEDGYNVYQSEAHGLPLHLPG
56_59_69R    GVIQILGVRTSRFLCQRPDGALYGSLHFDPEACSFRELLLEDGYNVYQSEAHGLPLHLPG
             ********.***************************************************

FGF21_SEQ1   NKSPHRDPAPRGPARFLPLPGLPPALPEPPGILAPQPPDVGSSDPLSMVGPSQGRSPSYA
56_59_69R    NKSPHRDPAPRGPARFLPLPGLPPALPEPPGILAPQPPDVGSSDPLSMVGPSQGRSPSYA
             ************************************************************

FGF21_SEQ1   S
56_59_69R    S
             *
```

Accordingly, the percentage of identity of this FGF21 analogue to FGF21 is 178/181×100%=98.3%.

In the alternative, the degree of identity between two amino acid sequences may be determined by the program "align" which is a Needleman-Wunsch alignment (i.e. a global alignment). The sequences are aligned by the program, using the default scoring matrix BLOSUM50. The penalty for the first residue of a gap is 12, and for further residues of a gap the penalties are 2. The Needleman- Wunsch algorithm is described in Needleman, S. B. and Wunsch, C D., (1970), *Journal of Molecular Biology*, 48: 443-453, and the align program by Myers and W. Miller in Optimal Alignments in Linear Space" CABIOS (computer applications in the biosciences) (1988) 4:11-17. "Align" is part of the FASTA package version v20u6 (see W. R. Pearson and D. J. Lipman (1988), "Improved Tools for Biological Sequence Analysis", *PNAS* 85:2444-2448, and W. R. Pearson (1990) "Rapid and Sensitive Sequence Comparison with FASTP and FASTA," *Methods in Enzymology* 183:63-98).

A pharmaceutical composition comprising a derivative of an FGF21 compound or an FGF21 analogue of the invention may further comprise a pharmaceutically acceptable carrier. For injection, the carrier may be water, if desired supplemented with other materials, e.g. saline, such as physiological saline. Other pharmaceutically acceptable agents such as diluents and appropriate buffers may also be used. If desired, additional pharmaceutically acceptable agents such as emulsifiers, suspending agents, solvents, fillers, bulking agents, adjuvants, preservatives, antioxidants, colouring agents, and/or flavouring agents may also be used. The derivative of an FGF21 compound or an FGF21 analogue may be used in the form of a purified polypeptide or a derivative thereof, or formulated using appropriate pharmaceutically acceptable excipients, as is known in the art. The pharmaceutical composition may be administered in any way as is known in the art, e.g. injected, for example intravenously (i.v.) or subcutaneously (s.c.).

The derivative of an FGF21 compound or an FGF21 analogue may be included in the pharmaceutical composition in a therapeutically or prophylactically effective amount. The amount depends upon the therapeutic or prophylactic objective, such as the indication in question, the condition of the patient in need of treatment, the desired route of administration, etc. The skilled medical practitioner may have to adjust dosage and modify the administration depending on these factors, as is routine in the art.

Particular Embodiments

The following are particular embodiments of the derivative of the invention, in particular of the derivative of the first aspect of the invention, in which an albumin binder of the formula A-B-C-D-E- is covalently attached to a thiol group of the FGF21 compound, i.e. e.g. a cysteine residue:

In one embodiment, A- is an element of formula I:

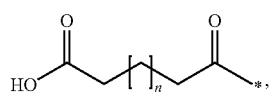
(formula I)

in which n is 14, 16 or 18.

In one embodiment, -B- comprises -B1-, preferably an element of formula IV or V:

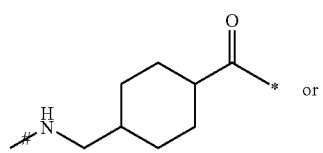
(formula IV)

or

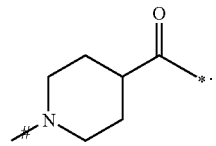
(formula V)

In one embodiment, -B- comprises -B2-, preferably one or two elements of formula IIX or IX:

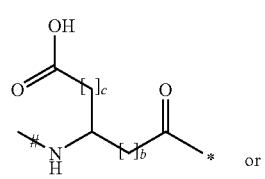
(formula IIX)

or

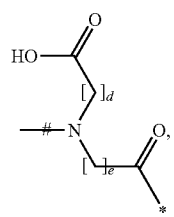
(formula IX)

in which more preferably c is 0 and b is 2 (gamma-Glu), or c is 0 and b is 1 (beta-Asp), or in which more preferably d is 1 and e is 2, or d is 2 and e is 1.

In one embodiment, -B- comprises -B2-, preferably one or two elements of formula IIX:

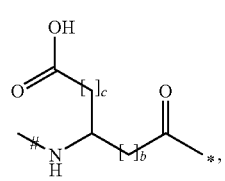
(formula IIX)

in which more preferably c is 0 and b is 2 (gamma-Glu) or c is 0 and b is 1 (beta-Asp).

In one embodiment, -C- is an element of formula X:

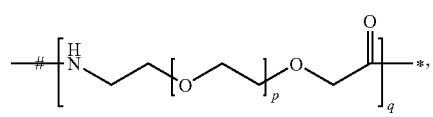
(formula X)

in which preferably q is 0, 1, 2, 3 or 4, more preferably q is 1 or 2.

In one embodiment, -C- is an element of formula X:

(formula X)

in which preferably p is 1 or 2, more preferably p is 1, even more preferably p is 1 and q is 1 or 2, or most preferably p is 1 and q is 2.

In one embodiment, -C- is an element of formula XI:

(formula XI)

in which preferably m is 0, 1 or 2, more preferably m is 1 or 2.

In one embodiment, -C- is an element of formula XI:

(formula XI)

in which preferably k is 1, 2, 3, 4, 5 or 11, more preferably k is 5.

In one embodiment, -C- is an element of formula XI:

(formula XI)

in which m is 1 and k is 4, 5 or 11, preferably m is 1 and k is 5.

In one embodiment, -D- is an element of formula XII:
—NH—(CH$_2$)$_r$—NH—CO—(CH$_2$)$_s$—* (formula XII), in which preferably r is 2, and/or in which preferably s is 1 or 2, most preferably r is 2 and s is 2.

In one embodiment, -D- is an element of formula XIII:
—NH—(CH$_2$)$_t$—* (formula XIII), in which preferably t is 1, 2 or 3, more preferably t is 2.

In one embodiment, -D- is absent.

In one embodiment, -E- is an element of formula XXII, XXIII, XXIV, XXV, XXVI or XXVII:

(formula XXII)

(formula XXIII)

(formula XXV)

(formula XXVI)

(formula XXIV)

(formula XXVII)

or a bond.

In one embodiment, -E- is an element of formula XXII, XXIII, XXV or XXVI:

(formula XXII)

(formula XXIII)

(formula XXV)

(formula XXVI)

or a bond.

In one embodiment, -E- is the reaction product of the FGF21 compound with an activated ester e.g. but not limited to N-hydroxy succinimide (formula XIV), or a reactive element of formula XV, XVI, XVII, IIXX, IXX, XX or XI:

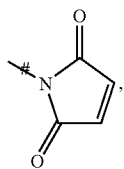
(formula XV)

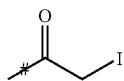
(formula XVI)

or the amide thereof (iodoacetamide),

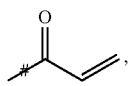
(formula XVII)

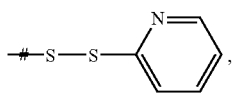
(formula IIXX)

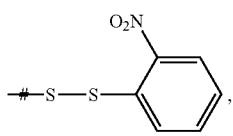
(formula IXX)

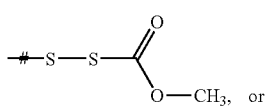
(formula XX)

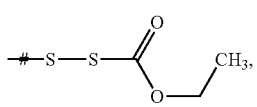
(formula XXI)

wherein # is the point of attachment to -C- or -D-.

In one embodiment, the derivative has one or two albumin binders of the formula A-B-C-D-E-.

In one embodiment, the derivative has two albumin binders, preferably wherein A- is an element of formula I, II or III:

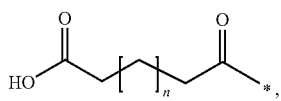
(formula I)

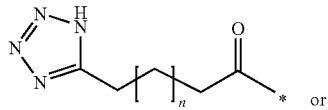
(formula II)
or

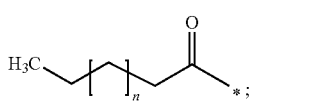
(formula III)

wherein n is 8, 9, 10, 11, 12 or 13.

In one embodiment, the derivative has two albumin binders, preferably wherein A- is an element of formula I, II or III:

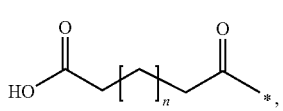
(formula I)

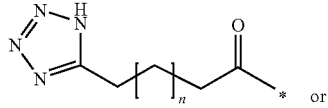
(formula II)
or

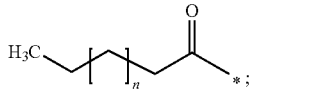
(formula III)

wherein n is 10, 11, 12 or 13.

In one embodiment, the derivative has one albumin binder, in which preferably A- is an element of formula I, II or III:

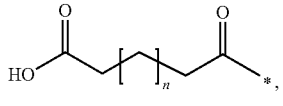
(formula I)

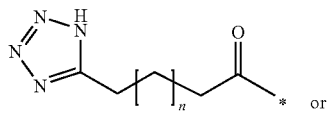
(formula II)
or

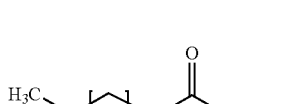
(formula III)

wherein n is 10, 11, 12, 13, 14, 15, 16, 17 or 18.

In one embodiment, the derivative has one albumin binder, in which preferably A- is an element of formula I, II or III:

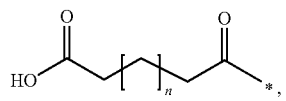
(formula I)
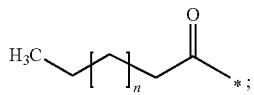
(formula III)
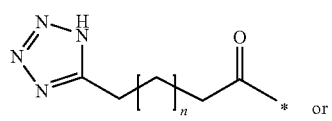
(formula II)
wherein n is 14, 15, 16, 17 or 18.
In one embodiment, A-B-C-D-E- is selected from the following formulas (1)-(12):
(1):
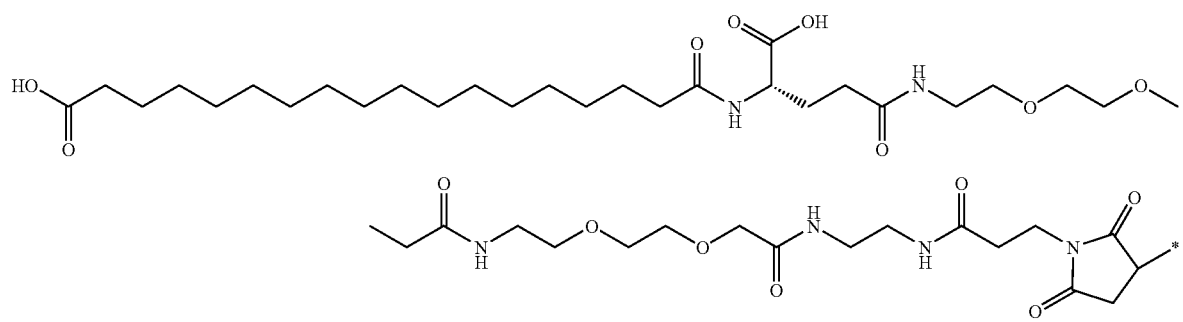
(2):
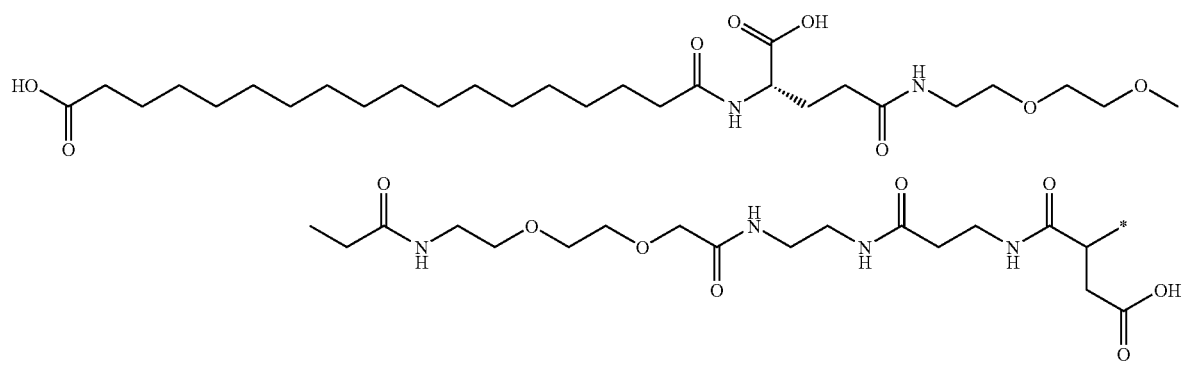
(3):
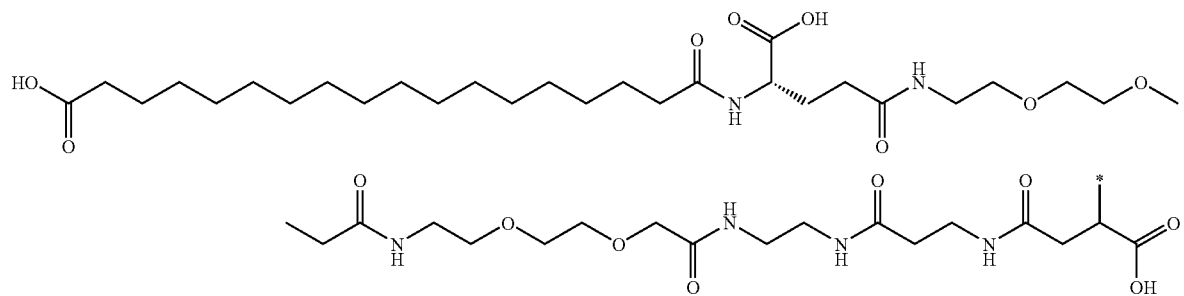

(4):
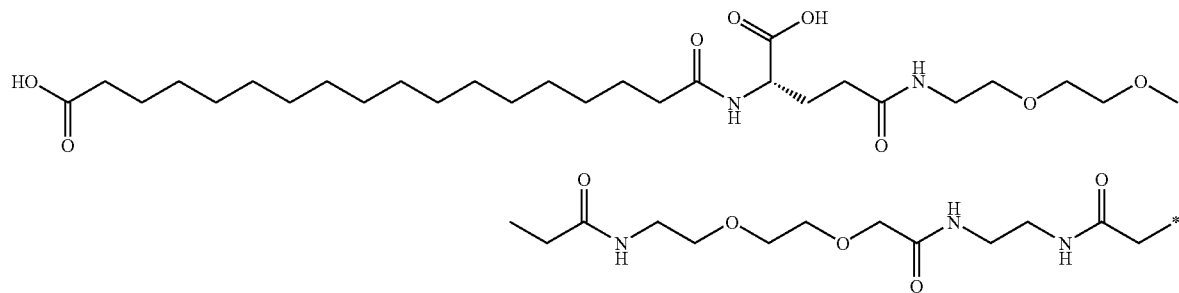
(5):
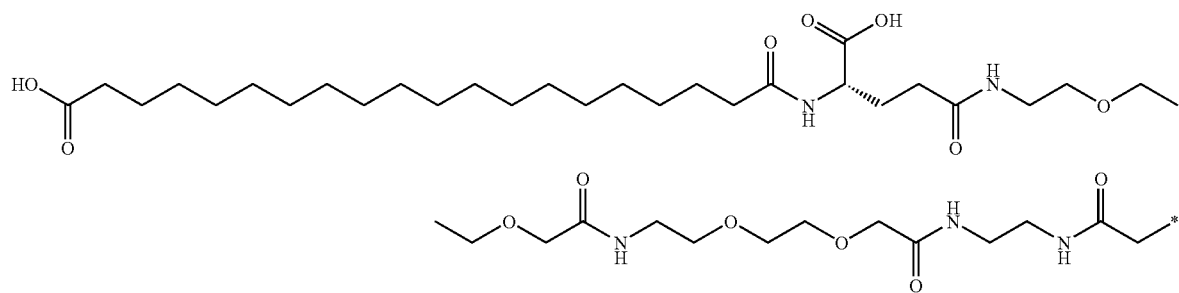
(6):
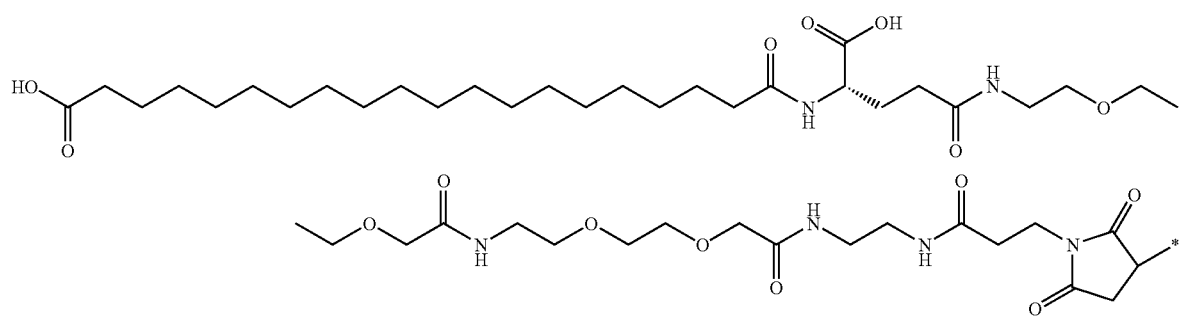
(7):
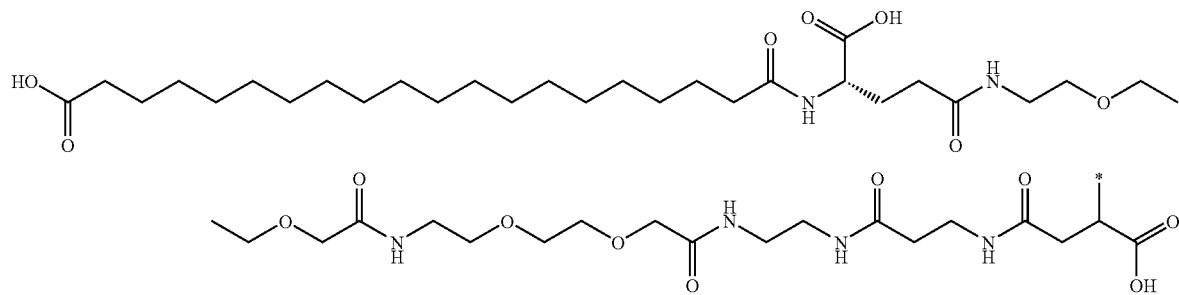

(8):
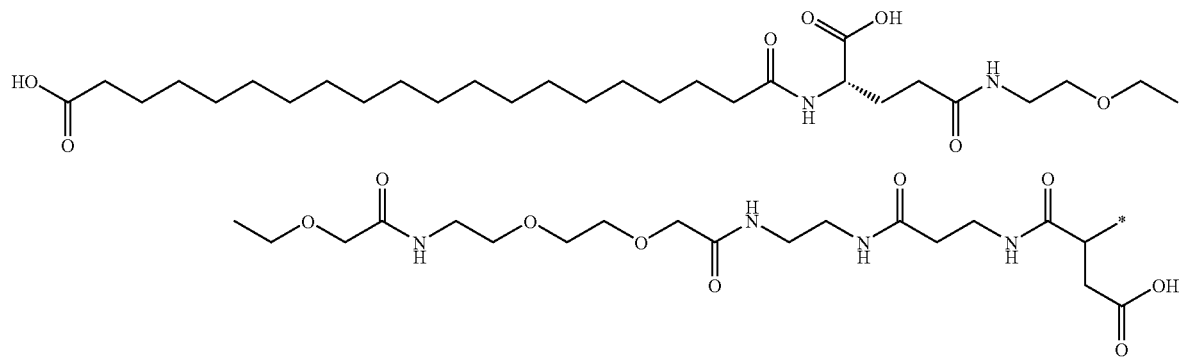
(9):
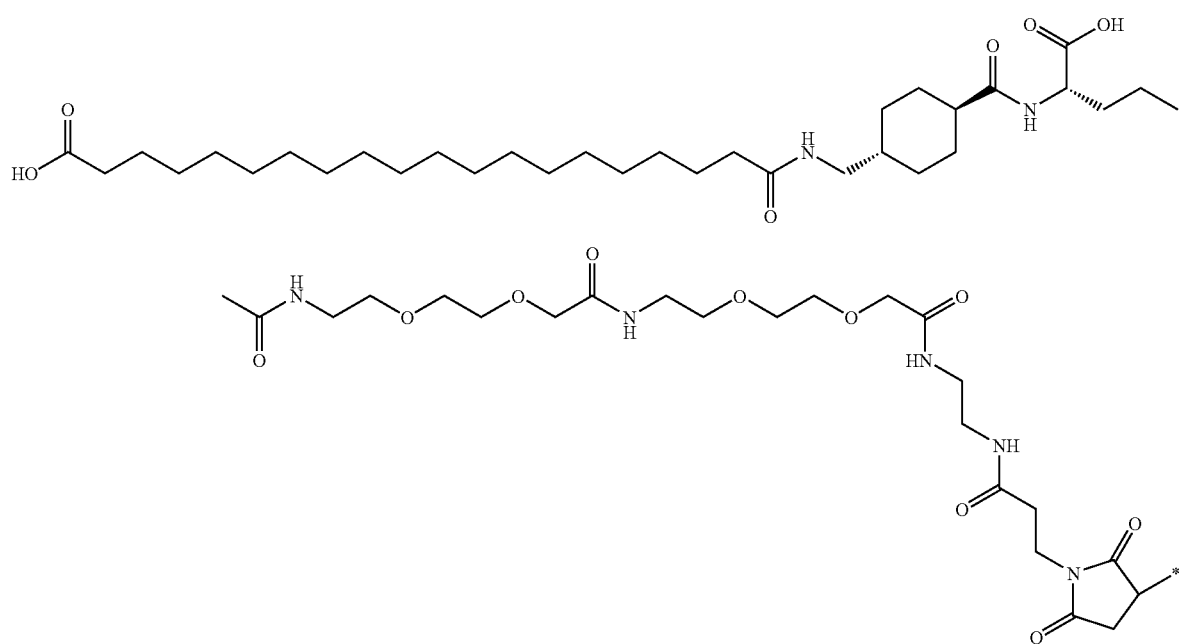
(10):
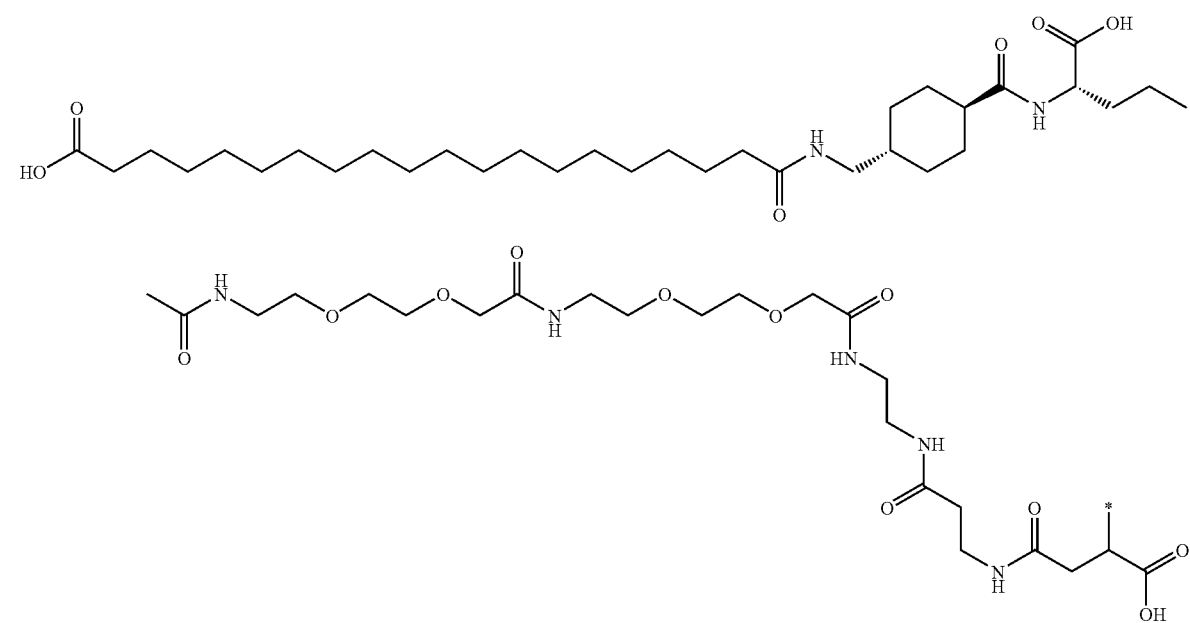

-continued
(11):
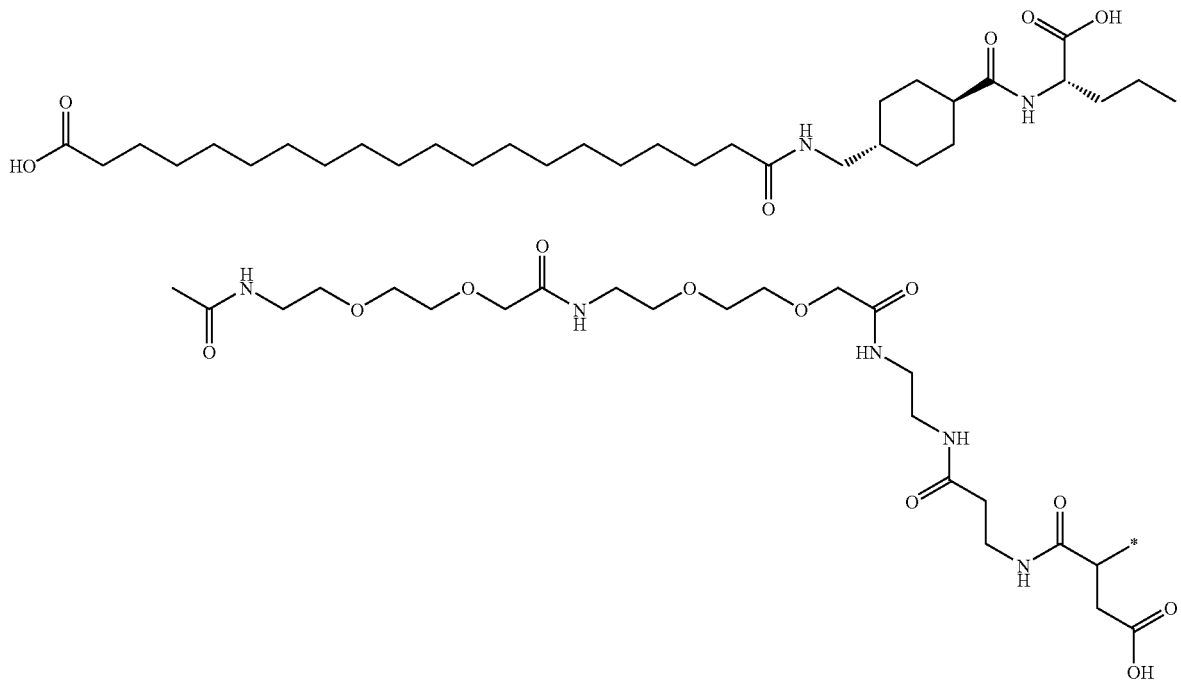
(12):
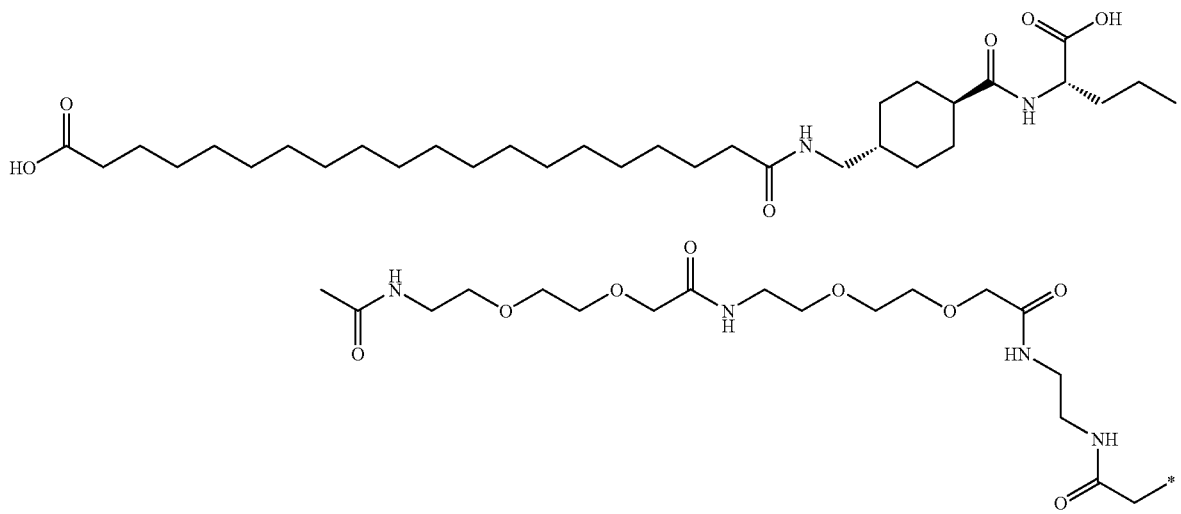
(13):
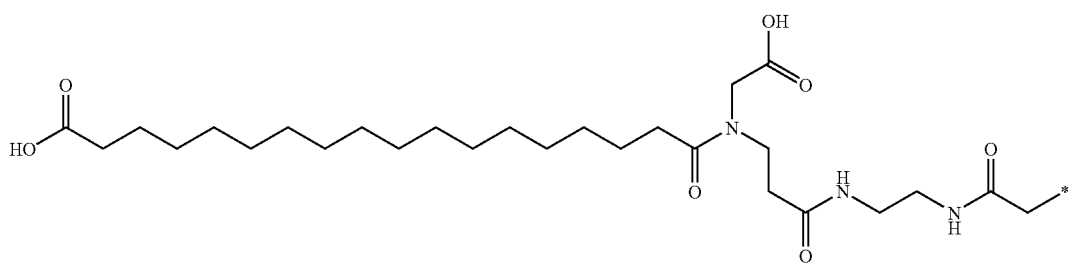

(14):
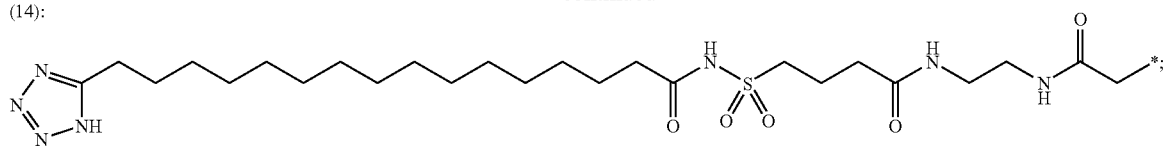
or pharmaceutically acceptable salts of any of the corresponding derivatives. The derivatives including (2) and (3) may by the way be generated by degradation of the derivative including formula (1).
In one embodiment, A-B-C-D-E- is selected from the following formulas (1)-(12):
(1):
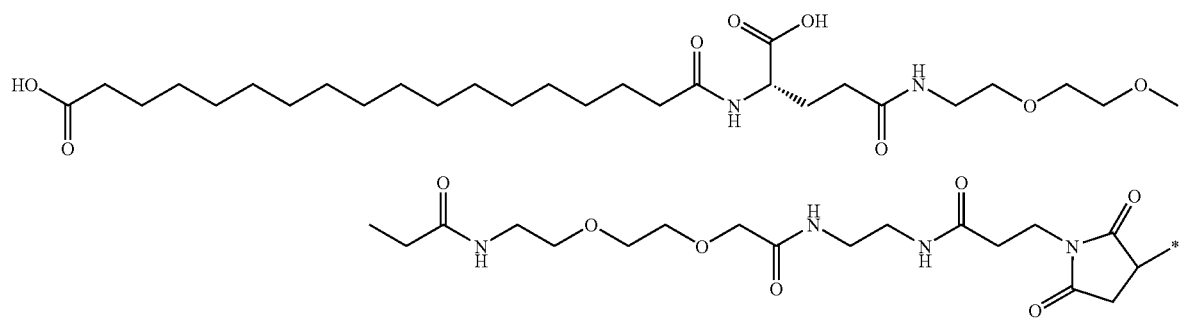
(2):
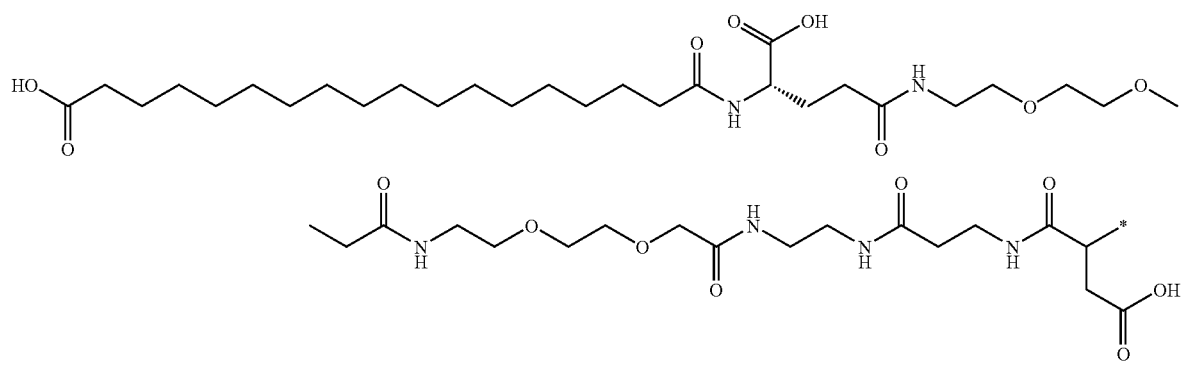
(3):
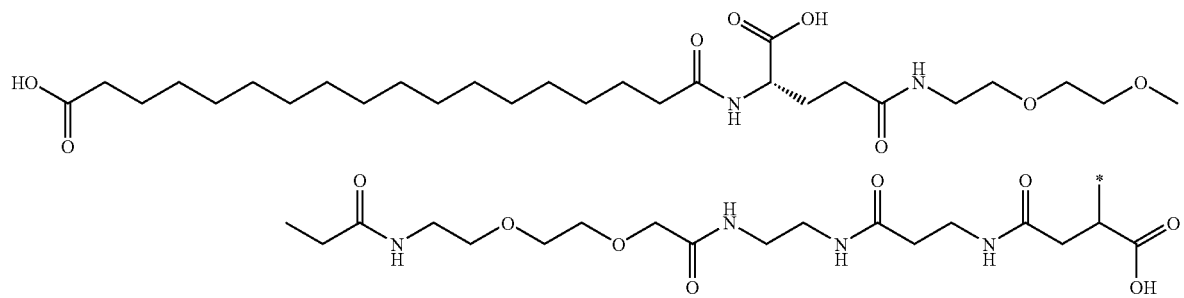

-continued
(4):
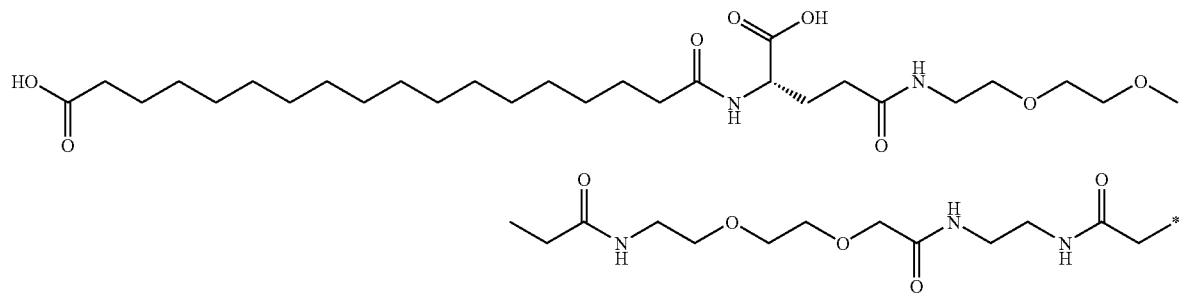
(5):
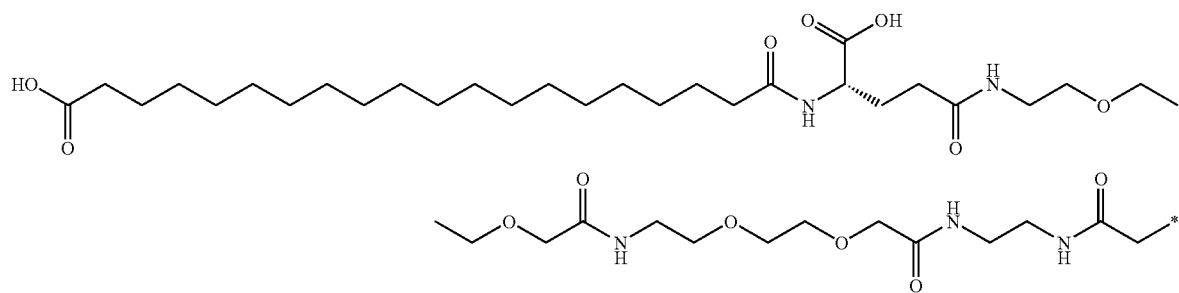
(6):
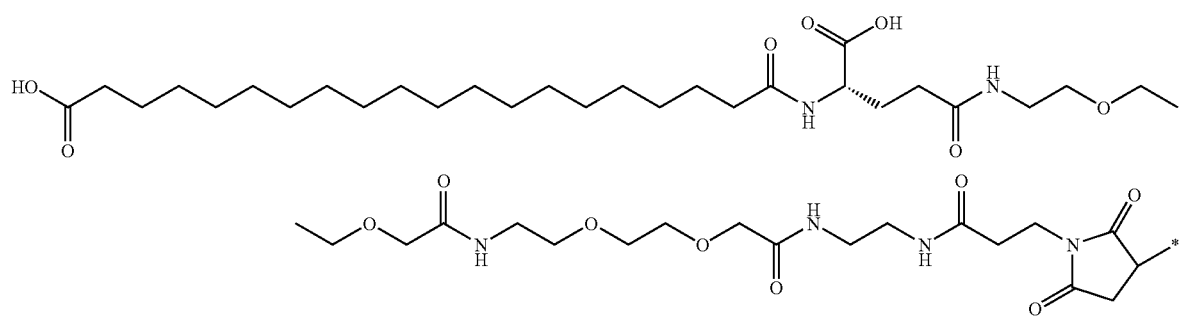
(7):
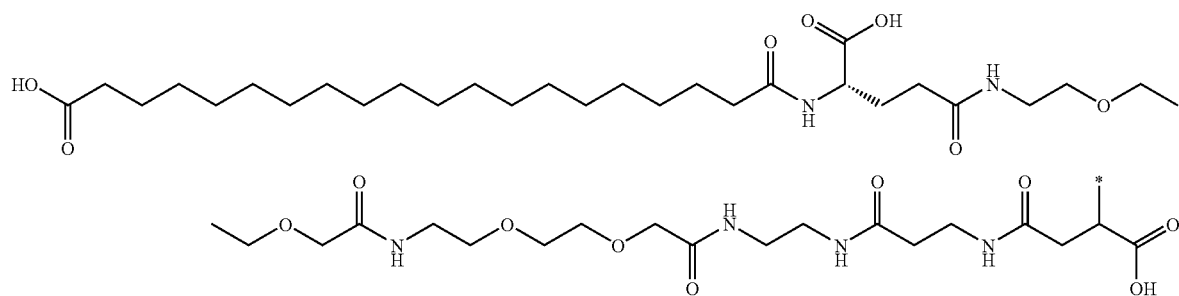

(8):
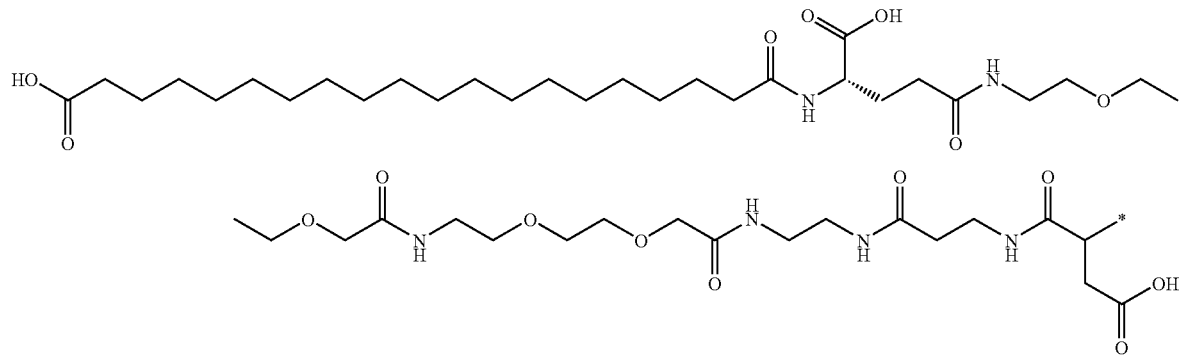
(9):
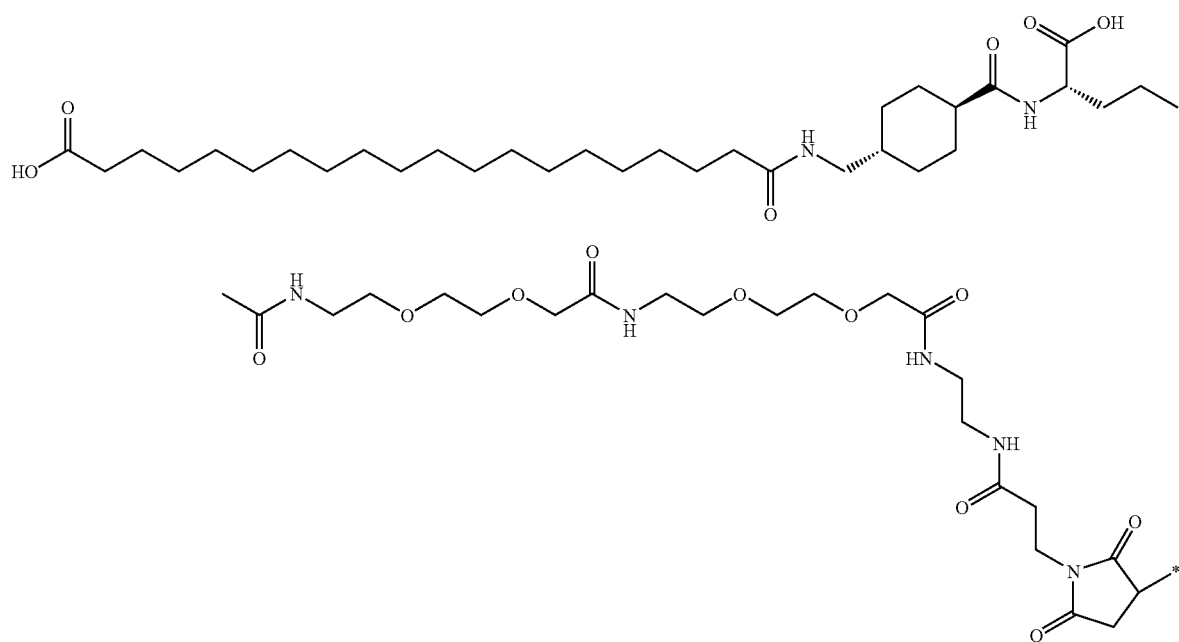
(10):
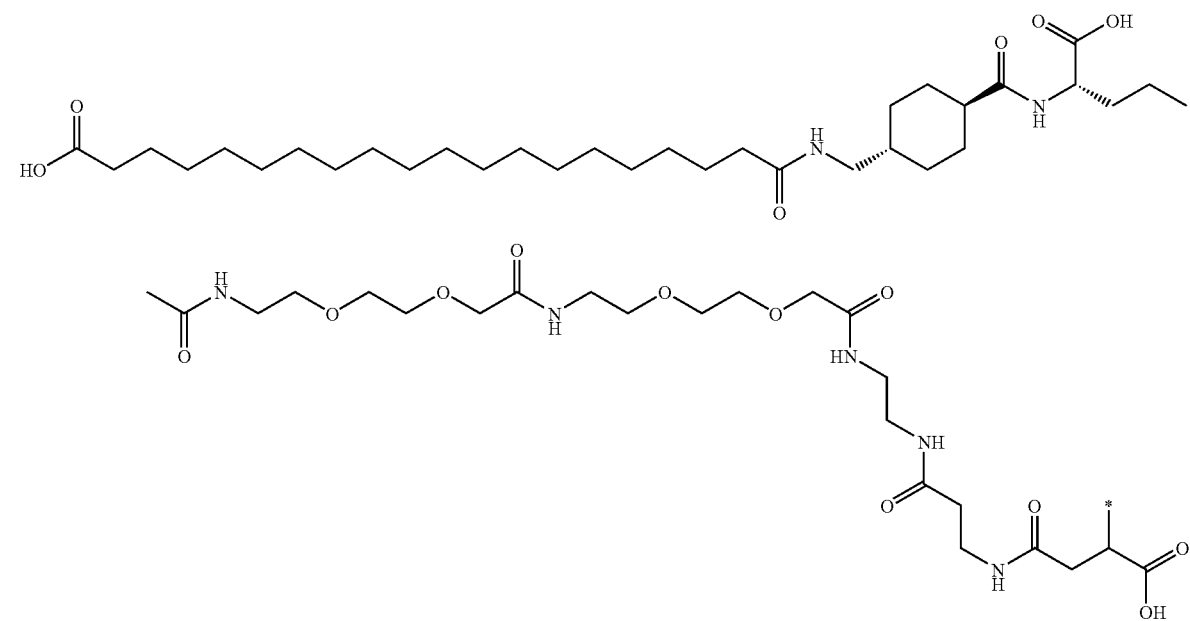

(11):

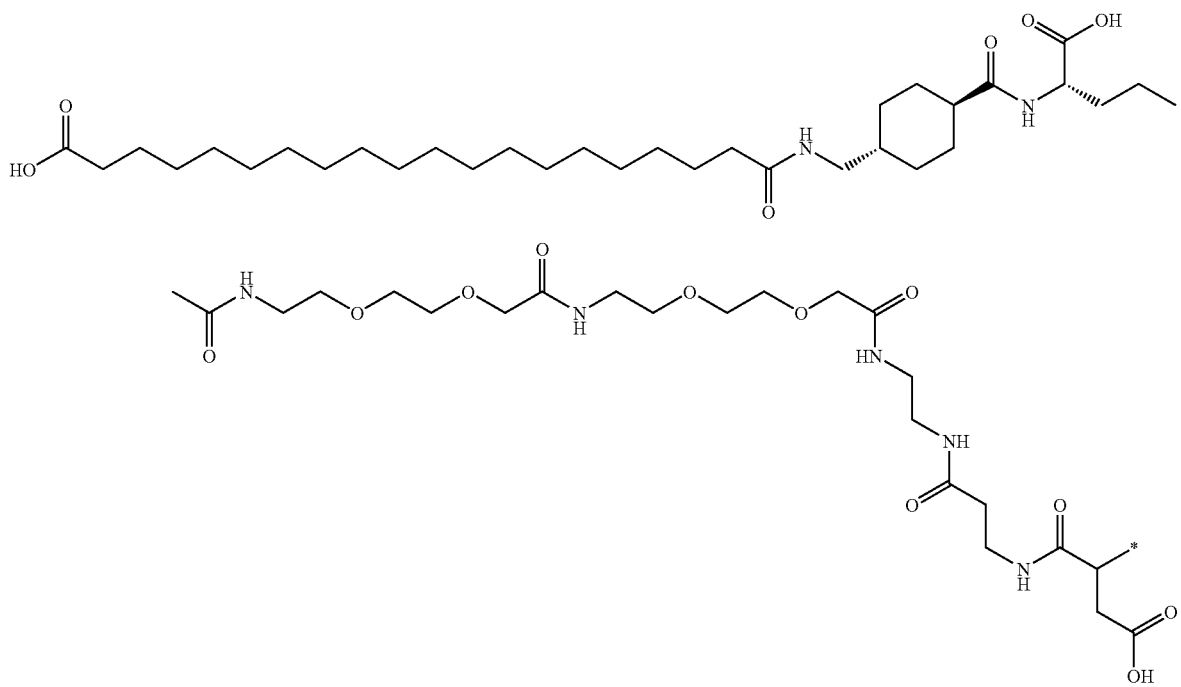

(12):

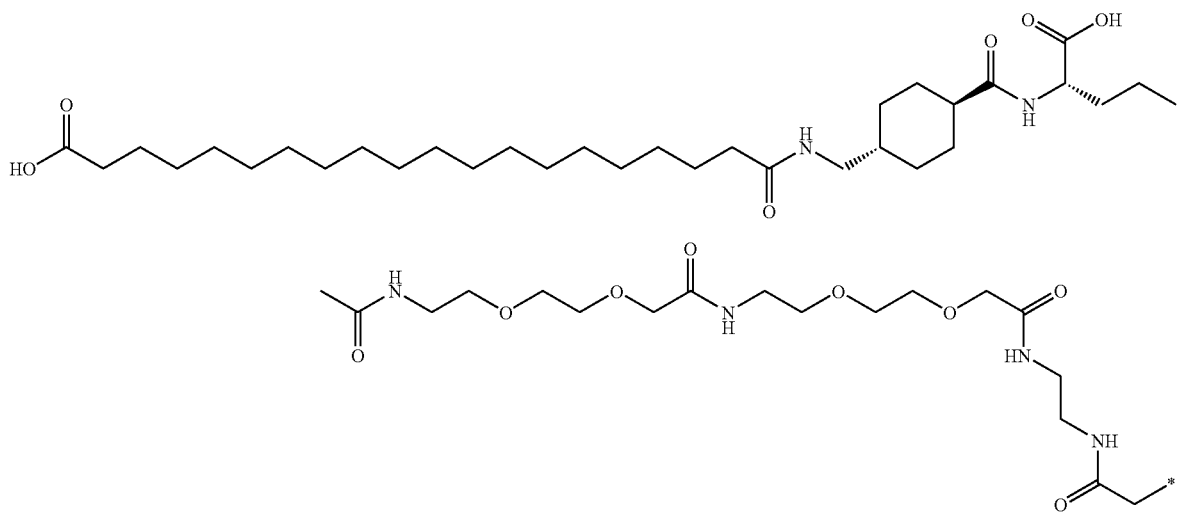

or pharmaceutically acceptable salts of any of the corresponding derivatives. The derivatives including (2) and (3) may by the way be generated by degradation of the derivative including formula (1).

In one embodiment, the albumin binder is attached to a cysteine residue at one or more (such as two) positions selected from positions −1 (e.g. in the analogue MetCys-FGF21), 6, 71, and 122 of the FGF21 compound, wherein the position numbering is by reference to SEQ ID NO:1.

In one embodiment, the compound of this invention is selected from the derivatives of Examples 4, 5 and 6, preferably the following: S-122-[1-(2-{2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-ethyl)-2,5-dioxo-pyrrolidin-3-yl] [Cys122]-Met- FGF21; S-71-[1-(2-{2-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-ethylcarbamoyl}-ethyl)-2,5-dioxo-pyrrolidin-3-yl] [Cys71] Met-FGF21; and S-71-({2-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-ethylcarbamoyl}-methyl) [Cys71] Met-FGF21; or a pharmaceutically acceptable salt of any of these compounds.

The following are particular embodiments of the derivative of the invention, in particular of the derivative of the second aspect of the invention, in which an albumin binder of the formula A-B-C- is covalently attached to an amino group of the FGF21 compound:

In one embodiment, A- is an element of formula I, II or III:

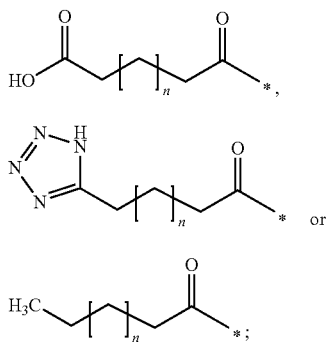
(formula I)

(formula II)

(formula III)

wherein n is 10, 11, 12, 13, 14, 15, 16, 17, 18 or 19, and * is the point of attachment to -B-;
-B- is -B1-, -B2- or combinations thereof, wherein -B1- is an element of formula IV, V, VI or VII:

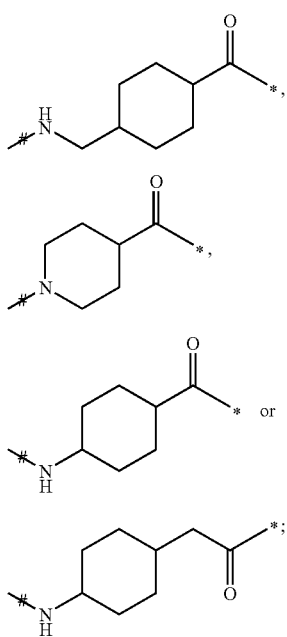
(formula IV or Trx)

(formula V or Inp)

(formula IV)

(formula VII)

wherein * is the point of attachment to -B2- or -C-, and # is the point of attachment to A- or -B2-; and
-B2- is an element of formula IIX, IX or XXVII or a combination of up to four elements of formula IIX and/or formula IX and/or XXVII:

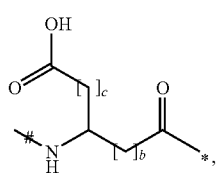
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-, or

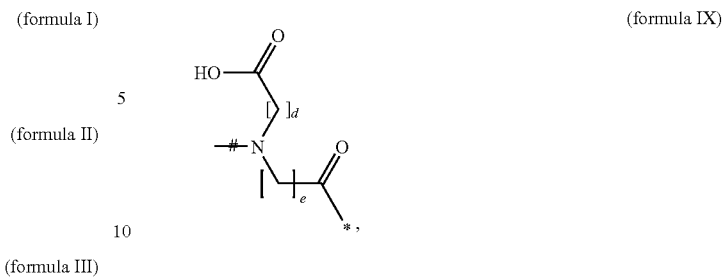
(formula IX)

wherein d is 1 or 2, e is 0, 1 or 2, * is the point of attachment to -C- or -B1-, and # is the point of attachment to A- or -B1-; or

—NH—SO$_2$—(CH$_2$)$_u$—CO—*     (formula XXVIII)

wherein u is 2, 3 or 4, * is the point of attachment to -C- or -B1-, and # is the point of attachment to A- or -B1- and;
-C- is an element of formula X or XI:

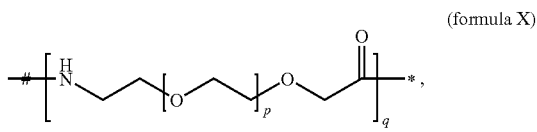
(formula X)

wherein p is 0, 1, 2, 3, 4, 5 or 6, q is 0, 1, 2, 3, 4, 5 or 6, * is the point of attachment to the FGF21 compound, and # is the point of attachment to -B-; or

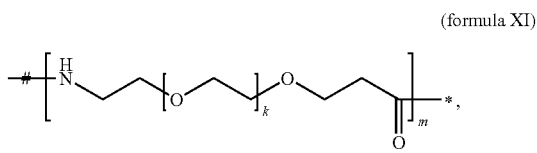
(formula XI)

wherein k is 0, 1, 2, 3, 4, 5, 11 or 23, m is 0, 1, 2, 3, 4, 5 or 6, * is the point of attachment to the FGF21 compound; and # is the point of attachment to -B-;
or a pharmaceutically acceptable salt thereof.

In one embodiment, A- is an element of formula I, II or III:

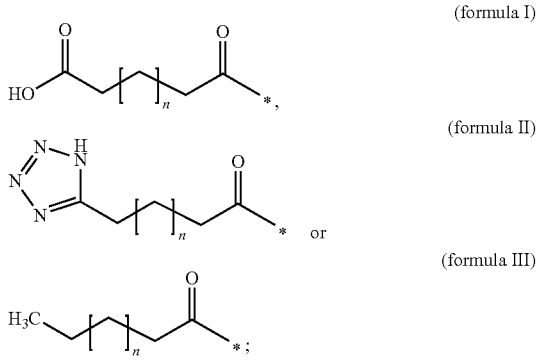
(formula I)

(formula II)

(formula III)

wherein n is 10, 11, 12, 13, 14, 15, 16, 17, 18 or 19, and * is the point of attachment to -B-;

-B- is -B1-, -B2- or combinations thereof, wherein
-B1- is an element of formula IV, V, VI or VII:

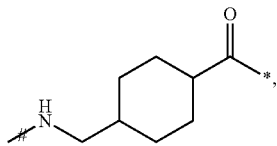
(formula IV or Trx)

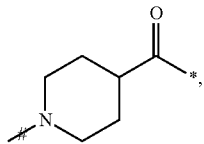
(formula V or Inp)

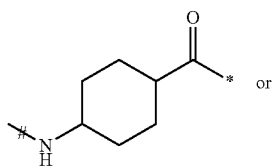
(formula VI)

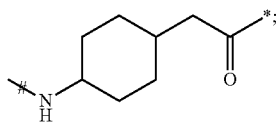
(formula VII)

wherein * is the point of attachment to -B2- or -C-, and # is the point of attachment to A- or -B2-; and
-B2- is an element of formula IIX or IX or a combination of up to four elements of formula IIX and/or formula IX:

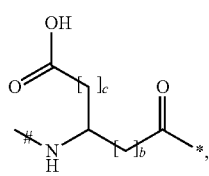
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-, or

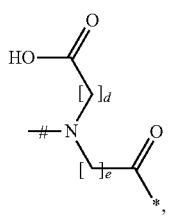
(formula IX)

wherein d is 1 or 2, e is 0, 1 or 2, * is the point of attachment to -C- or -B1-, and # is the point of attachment to A- or -B1-;

-C- is an element of formula X or XI:

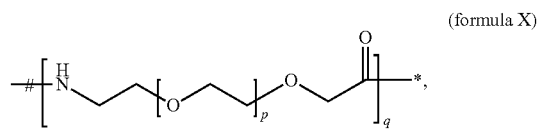
(formula X)

wherein p is 0, 1, 2, 3, 4, 5 or 6, q is 0, 1, 2, 3, 4, 5 or 6, * is the point of attachment to the FGF21 compound, and # is the point of attachment to -B-; or

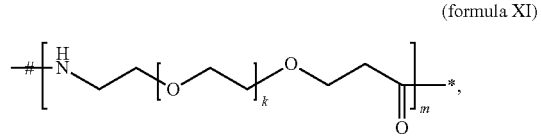
(formula XI)

wherein k is 0, 1, 2, 3, 4, 5, 11 or 23, m is 0, 1, 2, 3, 4, 5 or 6, * is the point of attachment to the FGF21 compound; and # is the point of attachment to -B-;
or a pharmaceutically acceptable salt thereof.

In one embodiment, A- is an element of formula I:

(formula I)

in which n is preferably 14, 16 or 18.

In one embodiment, -B- comprises -B1-, preferably an element of formula IV or V:

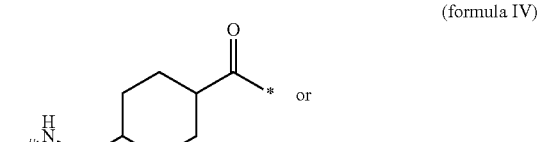
(formula IV)

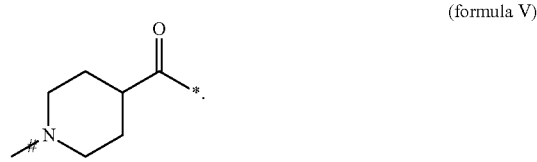
(formula V)

In one embodiment, -B- comprises -B2-, preferably one or two elements of formula IIX:

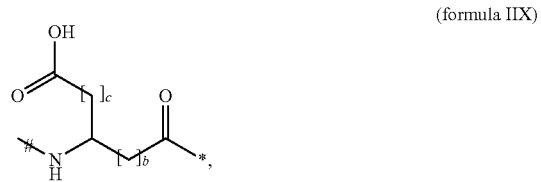
(formula IIX)

in which more preferably c is 0 and b is 2 (gamma-Glu) or c is 0 and b is 1 (beta-Asp).

In one embodiment, -B- comprises -B2-, preferably one or two elements of formula IX:

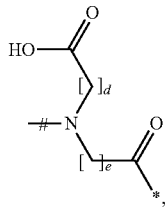
(formula IX)

in which more preferably d is 1 and e is 2, or d is 2 and e is 1.

In one embodiment, -B- comprises -B2-, preferably one or two elements of formula XXVIII:

—NH—SO$_2$—(CH$_2$)$_u$—CO—* (formula XXVIII), in which more preferably u is 3.

In one embodiment, -C- is an element of formula X:

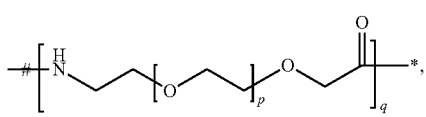
(formula X)

in which preferably q is 0, 1, 2, 3 or 4, more preferably q is 1 or 2.

In one embodiment, -C- is an element of formula X:

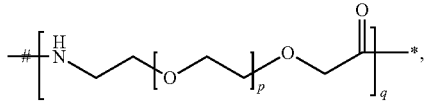
(formula X)

in which preferably p is 1 or 2, more preferably p is 1.

In one embodiment, -C- is an element of formula X:

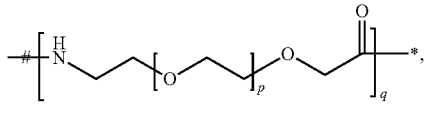
(formula X)

in which p is 1 and q is 1 or 2, preferably p is 1 and q is 2.

In one embodiment, -C- is an element of formula XI:

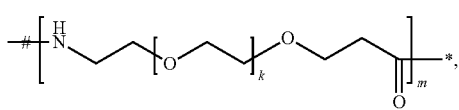
(formula XI)

in which preferably m is 0, 1 or 2, more preferably m is 1 or 2.

In one embodiment, -C- is an element of formula XI:

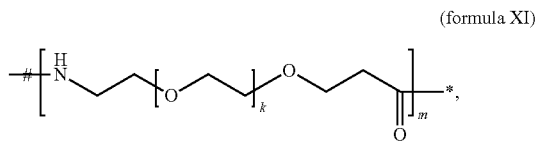
(formula XI)

in which preferably k is 1, 2, 3, 4, 5 or 11, more preferably k is 5, even more preferably m is 1 and k is 4, 5 or 11, or most preferably m is 1 and k is 5.

In one embodiment, the compound of this invention is a derivative having one or two albumin binders of the formula A-B-C-.

In one embodiment, the compound of this invention is a derivative which has two albumin binders, wherein preferably A- is an element of formula I, II or III:

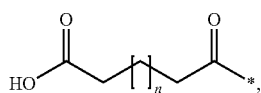
(formula I)

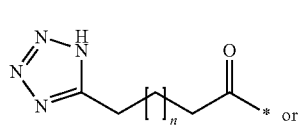
(formula II)

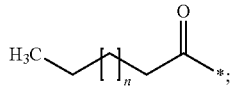
(formula III)

wherein n is 8, 9, 10, 11, 12 or 13.

In one embodiment, the compound of this invention is a derivative which has two albumin binders, wherein preferably A- is an element of formula I, II or III:

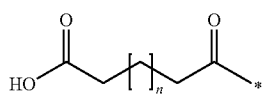
(formula I)

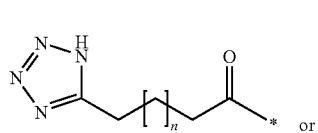
(formula II)

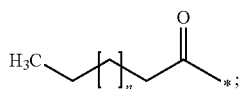
(formula III)

wherein n is 10, 11, 12 or 13.

In one embodiment, the compound of this invention is a derivative which has one albumin binder, wherein preferably A- is an element of formula I, II or III:

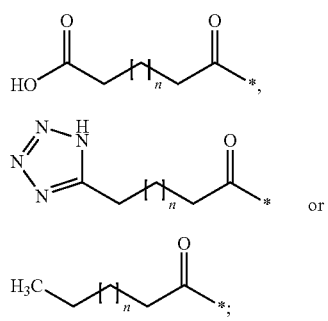

(formula I)

(formula II)

or (formula III)

wherein n is 10, 11, 12, 13, 14, 15, 16, 17 or 18.

In one embodiment, the compound of this invention is a derivative which has one albumin binder, wherein preferably A- is an element of formula I, II or III:

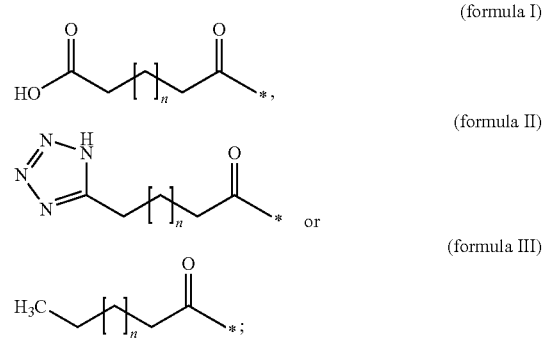

(formula I)

(formula II)

or (formula III)

wherein n is 14, 15, 16, 17 or 18.

In one embodiment, the compound of this invention is a derivative, wherein A-B-C- is selected from the following formulas (13)-(19):

(13):

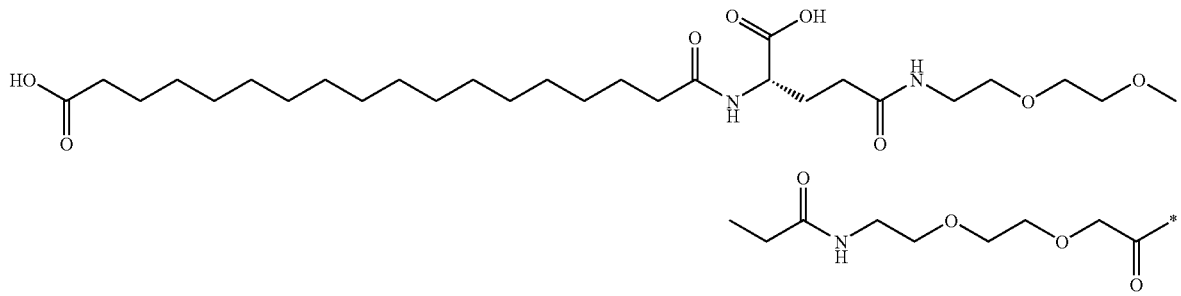

(14):

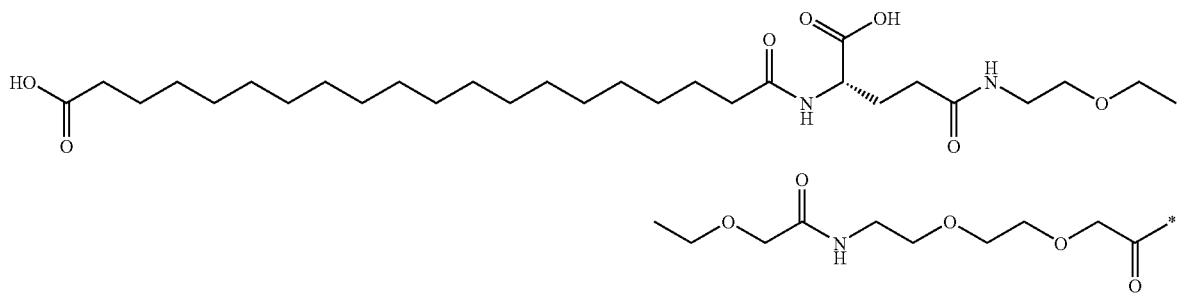

(15):

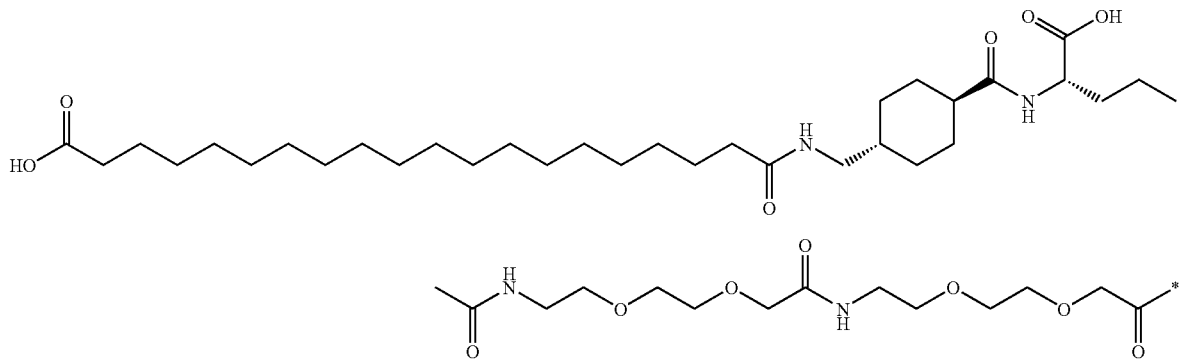

(16):
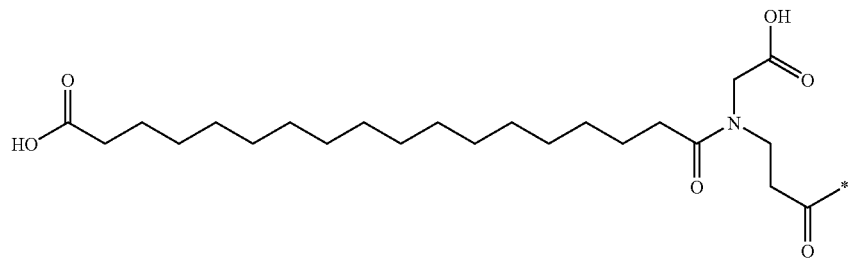
(17):
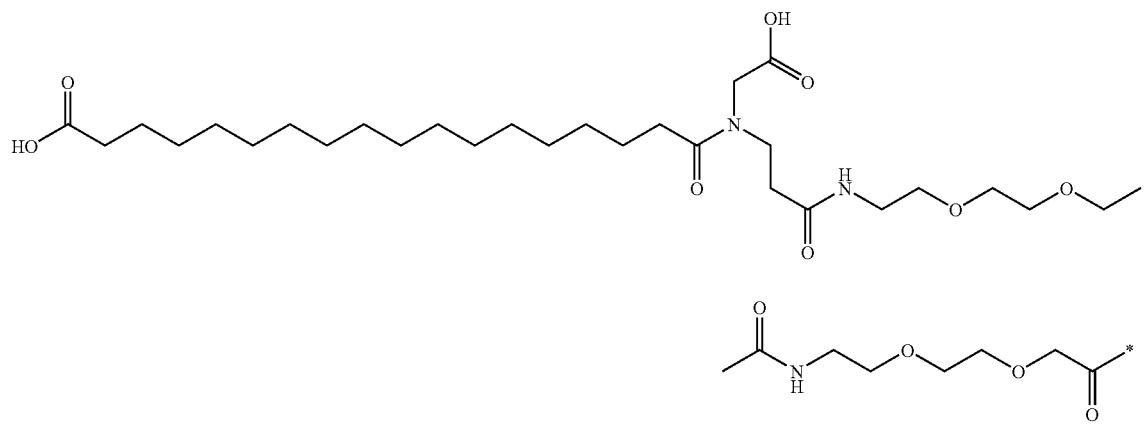
(18):
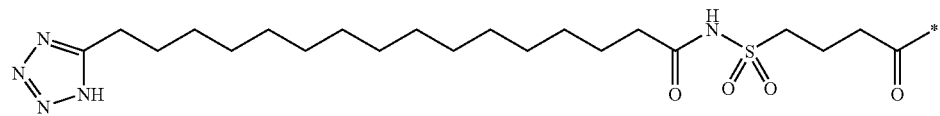
(19):
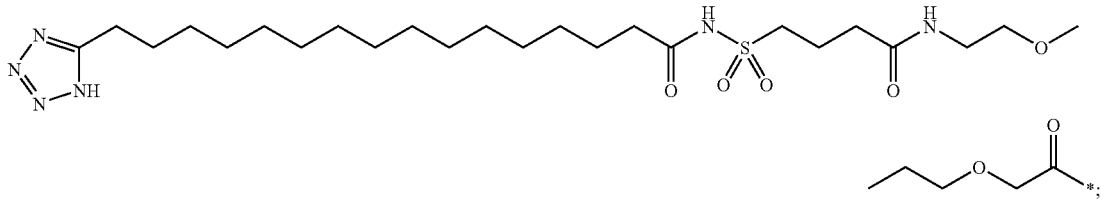
or a pharmaceutically acceptable salt of any one of the corresponding derivatives.
In one embodiment, the compound of this invention is a derivative, wherein A-B-C- is selected from the following formulas (13)-(15):
(13):
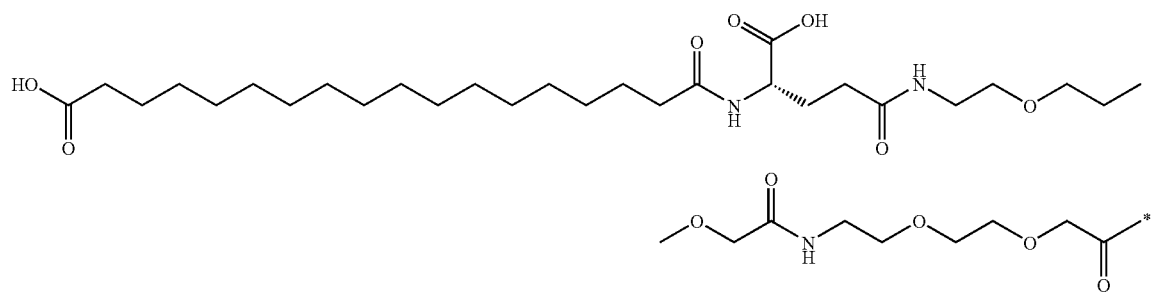

(14):

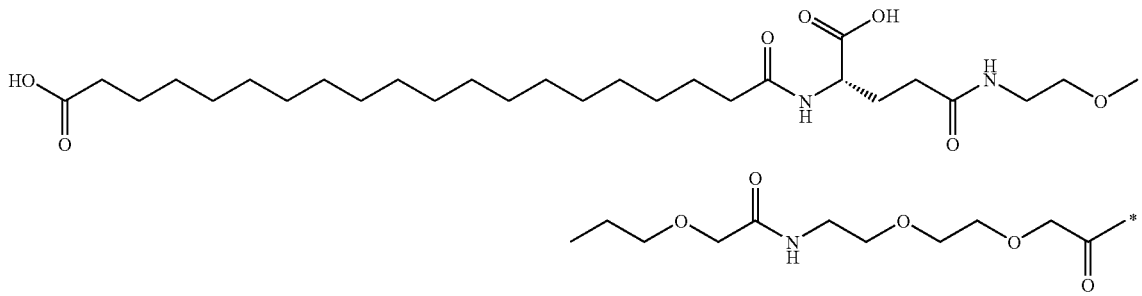

(15):

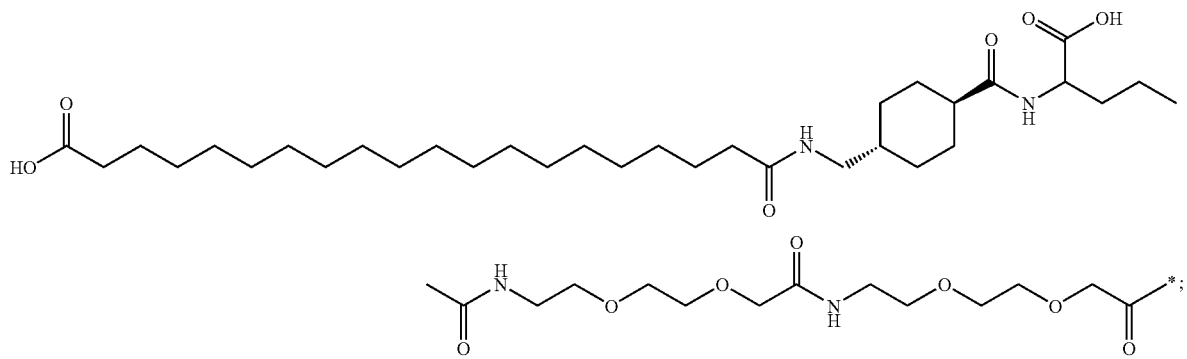

or a pharmaceutically acceptable salt of any one of the corresponding derivatives.

In one embodiment, the compound of this invention is one wherein the attachment of the albumin binder takes place via the amino group of the N-terminal amino acid residue, preferably under the formation of an amide bond.

In one embodiment, the compound of this invention is one wherein the attachment of the albumin binder takes place via the epsilon amino group of a lysine residue, preferably under the formation of an amide bond.

In one embodiment, the compound of this invention is one wherein one albumin binder is attached to the N-terminal amino acid residue and another to an internal lysine residue.

In one embodiment, the compound of this invention is one wherein the albumin binder(s) is/are attached to a lysine residue at one or more (such as two) positions selected from positions 56, 59, 69, 122 and 152 of the FGF21 compound, wherein the position numbering is by reference to SEQ ID NO:1.

In one embodiment, the compound of this invention is a compound of Example 7, preferably the following: N-alpha1-[2-(2-{2-[2-(2-{2-[(S)-4-carboxy-4-(17-carboxy-hepta-decanoylamino)-butyrylamino]-ethoxy}-ethoxy)-acetylamino]-ethoxy}-ethoxy)-acetyl] [Arg56, Arg59, Arg69, Arg122]-Met-FGF21; or a pharmaceutically acceptable salt thereof.

The following are additional particular embodiments of the derivative of the invention, as characterized by the structure of the constituent FGF21 compound:

Preferably, the FGF21 compound has an identity of at least 80%, to SEQ ID NO:1, preferably at least 85%, more preferably at least 90%, even more preferably at least 95%.

Preferably, the FGF21 compound has a maximum of 36 amino acid changes (modifications) as compared to SEQ ID NO:1, preferably a maximum of 30, 25, 20, 15, 14, 13, 12, 11, 10, 9, 8, 7, 6, 5, 4, 3, 2 or 1 amino acid change(s); more preferably a maximum of 15, 14, 13, 12, 11 or 10 amino acid modifications; even more preferably a maximum of 9, 8, 7, 6 or 5 amino acid modifications; or most preferably a maximum of 4, 3, 2 or 1 amino acid modification(s).

Preferably, the FGF21 compound has an N-terminal extension of up to 25 amino acid residues. Such extensions may be referred to using negative residue numbers, i.e. residue numbers −1 to −25 of SEQ ID NO:1. This N-terminal extension is a linker which is contemplated to facilitate the attachment of an albumin binder as defined and claimed herein to the N-terminus of the FGF21 compound. When this linker is used, the derivative may comprise only (or consist of) element A-, meaning that elements -B-, -C-, -D- and -E- may all be absent. Preferably, however, an element -B- and/or an element -C- is included in addition to A-, more preferably a -B1- element of Trx or Inp, or most preferably a -B2- element of formula IIX, IX or XXVII, in particular gamma-Glu. The N-terminal extension preferably has up to 20 amino acid residues, more preferably up to 15 amino acid residues, even more preferably up to 10 amino acid residues, or most preferably up to 6 amino acid residues.

Preferably, at least 50%, preferably at least 60%, more preferably at least 70%, even more preferably at least 80%, or most preferably at least 90% of the N-terminally extending amino acid residues are glycine or serine.

In one embodiment, the FGF21 compound comprises the amino acid sequence of SEQ ID NO:1.

In one embodiment, the FGF21 compound comprises (a) at least one of the following modifications as compared to SEQ ID NO:1: −1M, −1G, −1C, −1S, S6C, S6K, A26E, Q27E, Q28R, A31E, K56R, K59R, K69R, S71C, D102T, L118C, K122C, K122R, A134C, I152K, L166F, S167G, M168L, V169aT, P171L, S172E, Q173A, G174V, Y179F, A180E, and/or S181 K, R (preferably at least one of the following: −1 M, −1 G, −1 C, −1S, S6C, S6K, A26E, Q27E, Q28R, A31E, K56R, K59R, K69R, S71C, D102T, L118C, K122C, K122R, A134C, I152K and/or M168L); and/or (b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S.

In one embodiment, the FGF21 compound comprises (a) the following modifications, as compared to SEQ ID NO:1: (i) K122C, (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31E), Q27E, M168L, (Y179F, A180E, S181R), (V169aT, P171L, S172E, Q173A, G174V, Y179F, A180E, S181K), and/or (L166F, S167G, M168L, V169aT, P171L, S172E, Q173A, G174V, Y179F, A180E, S181K) (preferably K122C, (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31E), Q27E, and/or M168L), (ii) −1G, and (−1G, M168L), or (iii) S6C, (L118C-A134C, K56R, K59R, K69R, K122R), and (S6K, K56R, K59R, K69R, K122R), wherein the FGF21 compound of (i) and (iii) may further, optionally, include an N-terminal M; and/or (b) an N-terminal extension as compared to SEQ ID NO:1 selected from the following: (iv) MG-, MC-, MS-, MSGSGSGSGSG-, MGGGGG-, MSHSGSGSGSGSGSGSGSG-, MSGGGGG-, MSGSGGS-, MSGGSSG-, and MSGSGSG-, wherein the N-terminal M in each of the FGF21 compounds of (iv) may, optionally, be deleted.

In one embodiment, the FGF21 compound comprises Y179F, A180E and S181K or S181R (i); preferably it additionally comprises V169aT, P171L, S172E, Q173A and G174V (ii); more preferably it additionally comprises L166F, S167G and M168L (iii); most preferably it comprises (i), (ii) and (iii). Each of these embodiments (i)-(iii) optionally includes an N-terminal M (e.g., −1M).

In one embodiment, the FGF21 compound comprises the following substitutions as compared to SEQ ID NO:1: (a) K122C; (b) (K59R, K69R, K122R); (c) (K56R, K69R, K122R); (d) (K56R, K59R, K69R); (e) S71C; (f) S6C; (g) (K56R, K59R, K69R, K122R); (h) (K56R, K59R, K69R, K122R, I152K); (i) (L118C-A134C, K56R, K59R, K69R, K122R); (j) (S6K, K56R, K59R, K69R, K122R); or (k) M168L.

In one embodiment, the FGF21 compound comprises the following amendments as compared to FGF21 (SEQ ID NO:1): (i) Met-Gly- at the N-terminus, (ii) M168L, (iii) embodiment (i) and (ii), (iv) Met-Cys- at the N-terminus, (v) Gly- at the N-terminus, (vi) embodiment (v) and (ii), (vii) Met-Ser- at the N-terminus, or (iix) Ser- at the N-terminus; preferably the FGF21 compound is selected from the following: (l) Met-Gly-FGF21, (m) Met-Gly-FGF21-M168L, (n) Met-Cys-FGF21, (o) Gly-FGF21-M168L, (p) Gly-FGF21, (q) Met-Ser-FGF21, or (r) Ser-FGF21; wherein FGF21 refers to the polypeptide of SEQ ID NO:1.

In one embodiment, the FGF21 compound comprises the following N-terminal extensions as compared to SEQ ID NO:1: (q) MS-FGF21, (s) MSGSGSGSGSG-, (t) MGGGGG-, (u) MSHSGSGSGSGSGSGSGSG-, (v) MSGGGGG-, (x) MSGSGGS-, (y) MSGGSSG-, and (z) MSGSGSG-; as well as any one of the embodiments (q), (s), (t), (u), (v), (x), (y), and (z) without the N-terminal Met.

In one embodiment, the FGF21 compound is selected from the following variants of the polypeptide of SEQ ID NO:1: (a) K122C, (e) S71C, (f) S6C, (n) Met-Cys-FGF21, any one of the compounds (a), (e) and (f) with an N-terminal Met, and compound (n) without the N-terminal Met.

In one embodiment, the FGF21 compound is selected from the following variants of the polypeptide of SEQ ID NO:1: (b) (K59R, K69R, K122R); (c) (K56R, K69R, K122R); (d) (K56R, K59R, K69R); (g) (K56R, K59R, K69R, K122R); (h) (K56R, K59R, K69R, K122R, I152K); (i) (L118C-A134C, K56R, K59R, K69R, K122R); (j) (S6K, K56R, K59R, K69R, K122R); (k) (179F, 180E, 181R); (I) (169aT, 171L, 172E, 173A, 174V, 179F, 180E, 181K); as well as and (m) (166F, 167G, 168L, 169aT, 171L, 172E, 173A, 174V, 179F, 180E, 181K); as well as any one of the compounds (b), (c), (d), (g), (h), (i), (j), (k), (I) and (m) with an N-terminal Met (preferably (b)-(j)±1- N-terminal Met).

In one embodiment, the FGF21 compound has a proline at position 146, wherein the position number refers to SEQ ID NO:1, which is an allelic wild type form of FGF21 known from the prior art.

The following are additional particular embodiments of the derivative of the invention, as characterized by biological and chemical properties:

In one embodiment, the derivative of this invention is preferably protracted, cf. Example 11 of the Experimental section herein.

In one embodiment, the derivative of this invention has a T½ when dosed s.c. in mice of at least 1.5 hours, preferably at least 2 hours, more preferably at least 4 hours, even more preferably at least 5 hours, or most preferably at least 6 hours.

In one embodiment, the derivative has a T½ when dosed s.c. in mice of at least 10 hours, preferably at least 15 hours, more preferably at least 24 hours, or most preferably at least 48 hours. The mice are db/db mice, preferably mice that lack the leptin receptor.

In one embodiment, the dosage of the derivative is 0.5 mg/kg, although a dosage in the range of 0.1 to 1.0 mg/kg may also be used.

In another embodiment, the derivative of this invention has a T½ when dosed i.v. in mini pig of at least 15 hours, preferably at least 20 hours, more preferably at least 30 hours, even more preferably at least 40 hours, or most preferably at least 50 hours.

The derivative of this invention may even have a T½ when dosed i.v. in mini pig of at least 60 hours, preferably of at least 70 hours, more preferably of at least 75 hours. The mini pigs are preferably normal male Gottingen mini pigs. The number of pigs in each treatment group is preferably n=3-4. The pigs are preferably 12-15 months old, and more preferably of a weight of approximately 25 kg. The pigs are preferably dosed a single intravenous dose of preferably 0.1 mg/kg (approximately 5 nmol/kg).

The plasma concentration of the derivatives and analogues of the invention as well as comparative FGF21 compounds may be determined by any suitable method known in the art. A preferred assay is Fibroblast Growth Factor-21 Human ELISA, available from BioVendor with catalogue no. RD191108200R (e.g. BioVendor GmbH, Im Neuenheimer Feld 583, D-69120 Heidelberg, Germany).

The derivative preferably has an acceptable potency, cf. Example 8 of the Experimental section herein.

In one embodiment, the potency is at least 1%, preferably at least 5%, more preferably at least 10%, even more preferably at least 20%, or most preferably at least 30% of the potency of Met-FGF21, wherein the potency is determined by measuring glucose uptake in 3T3-L1 adipocytes.

In one embodiment, the potency is at least 40%, preferably at least 50%, more preferably at least 60%, even more preferably at least 70%, relative to the potency of Met-FGF21.

In one embodiment, the potency may even be at least 80%, preferably at least 90%, more preferably at least 100%, even more preferably at least 110%, or most preferably at least 120%, relative to the potency of Met-FGF21.

For each of these embodiments the potency is preferably determined by measuring glucose uptake in 3T3-L1 adipocytes.

The potency is calculated as the $EC_{50}$ of the derivative relative to the $EC_{50}$ of Met-FGF21.

The 3T3-L1 adipocytes derive from mouse 3T3-L1 fibroblasts, preferably ATCC CL-173.

The glucose uptake in 3T3-L1 adipocytes may be measured as outlined in Example 8.

The derivative of this invention preferably has an acceptable potency and an extended half-life:

In one embodiment, the derivative of this invention has a T½ when dosed s.c. in mice of at least 1.5 hours, preferably at least 2 hours, more preferably at least 4 hours, even more preferably at least 5 hours, or most preferably at least 6 hours—and at the same time a potency as described in any one of the above embodiments.

In one embodiment, the derivative of this invention has a T½ when dosed s.c. in mice of at least 10 hours, preferably at least 15 hours, more preferably at least 24 hours, or most preferably at least 48 hours—and at the same time a potency as described in any one of the above embodiments.

In one embodiment, the derivative of this invention has a T½ when dosed i.v. in mini pig of at least 15 hours, preferably at least 20 hours, more preferably at least 30 hours, even more preferably at least 40 hours, or most preferably at least 50 hours—and at the same time a potency as described in any one of the above embodiments.

In one embodiment, the derivative has a T½ when dosed i.v. in mini pig of at least 60 hours, preferably of at least 70 hours, more preferably of at least 75 hours—and at the same time a potency as described in any one of the above embodiments.

The derivative has effect in vivo on the blood glucose level of db/db mice, cf. Example 11 of the Experimental section herein:

The derivative is capable of lowering blood glucose in vivo in db/db mice relative to a vehicle control.

In one embodiment, the blood glucose value is lowered 24 hours, preferably 48 hours, after a last dose of the derivative has been administered.

In one embodiment, the blood glucose value is lowered by at least 10%, preferably by at least 15%, more preferably by at least 20%, even more preferably by at least 25%, or most preferably by at least 30%, based on the mean blood glucose measurements in mM and relative to the corresponding vehicle control. As an example, by reference to the data of Table 3: 48 hours after the last dose, the derivative of Example 4, dosed 0.22 mg/kg, gives rise to a mean blood glucose measurement of 17.1 mM. At the same point in time, the vehicle gives rise to a mean blood glucose measurement of 23.9 mM. Accordingly, the derivative of Example 4, dosed 0.22 mg/kg, gives rise to a lowering or reduction of blood glucose of 100%−(100×17.1/23.9)%=28%, as compared to the vehicle control.

In one embodiment, the blood glucose value is lowered by at least 35%, preferably by at leat 40%, more preferably by at least 45%, or most preferably by at least 50%, vide the test method in example 10.

The derivatives of the invention are preferably oxidation stable, by reference to Example 9 herein.

In one embodiment, the derivative of this invention is more stable than Met-FGF21 toward oxidation. This can be tested by storage at various temperatures and checking for oxidation or by incubation in the presence of 300 mM $H_2O_2$ for 1 hour at 25° C.

The term "stable", i.e., stability, refers to potency, determined as described above.

After incubation with $H_2O_2$ the derivative has a potency of at least 15%, preferably at least 20%, more preferably at least 30%, even more preferably at least 40%, or most preferably at least 50%, wherein the potency is relative to Met-FGF21 treated in the same way, however without $H_2O_2$.

The following are particular embodiments of the FGF21 analogues of the invention, first defined by structure, next by biological and chemical properties, and lastly a few additional structural embodiments:

One embodiment is an FGF21 analogue comprising (a) at least one of the following modifications as compared to SEQ ID NO:1: −1G, −1C, −1S, S6C, S6K, A26E, Q27E, Q28R, A31E, K56R, K59R, K69R, S71C, D102T, K122R, I152K, L166F, S167G, M168L, V169aT, P171L, S172E, Q173A, G174V, Y179F, A180E, and/or S181K,R (preferably −1G, −1C, −1S, S6C, S6K, A26E, Q27E, Q28R, A31E, K56R, K59R, K69R, S71C, D102T, K122R, I152K, and/or M168L); and/or (b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S.

One embodiment is an FGF21 analogue, which comprises (a) the following modifications, as compared to SEQ ID NO:1: (i) (K122C), (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31E), Q27E, M168L, (Y179F, A180E, S181 R), (V169aT, P171L, S172E, Q173A, G174V, Y179F, A180E, S181K), or (L166F, S167G, M168L, V169aT, P171L, S172E, Q173A, G174V, Y179F, A180E, S181K) (preferably (K59R, K69R, K122R), (K56R, K69R, K122R), (K56R, K59R, K69R), S71C, (K56R, K59R, K69R, K122R), and/or (K56R, K59R, K69R, K122R, I152K), D102T, A26E, (Q28R, A31E), Q27E, and/or M168L), (ii) −1G, and (−1G, M168L), or (iii) S6C, (L118C-A134C, K56R, K59R, K69R, K122R), and (S6K, K56R, K59R, K69R, K122R), wherein the FGF21 analogue of (i) and (iii) may further, optionally, include an N-terminal M; and/or (b) an N-terminal extension as compared to SEQ ID NO:1 selected from the following: (iv) MG-, MC-, MS-, MSGSGSGSGSG-, MGGGGG-, MSHSGSGSGSGSGSGSGSG-, MSGGGGG-, MSGSGGS-, MSGGSSG-, and MSGSGSG-, wherein the N-terminal M in each of the FGF21 analogues of (iv) may, optionally, be deleted.

One embodiment is an FGF21 analogue, which comprises (a) the following modifications, as compared to SEQ ID NO:1: (i) (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31E), Q27E, M168L, (Y179F, A180E, S181R), (V169aT, P171L, S172E, Q173A, G174V, Y179F, A180E, S181K), or (L166F, S167G, M168L, V169aT, P171L, S172E, Q173A, G174V, Y179F, A180E, S181K) (preferably (K59R, K69R, K122R), (K56R, K69R, K122R), (K56R, K59R, K69R), S71C, (K56R, K59R, K69R, K122R), and/or (K56R, K59R, K69R, K122R, I152K), D102T, A26E, (Q28R, A31E), Q27E, and/or M168L), (ii) −1G, and (−1G, M168L), or (iii) S6C, (L118C-A134C, K56R, K59R, K69R, K122R), and (S6K, K56R, K59R, K69R, K122R), wherein the FGF21 analogue of (i) and (iii) may further, optionally, include an N-terminal M; and/or (b) an N-terminal extension as compared to SEQ ID NO:1 selected from the following: (iv) MG-, MC-, MS-, MSGSGSGSGSG-, MGGGGG-, MSHSGSGSGSGSGSGSGSG-, MSGGGGG-, MSGSGGS-, MSGGSSG-, and MSGSGSG-, wherein the N-terminal M in each of the FGF21 analogues of (iv) may, optionally, be deleted.

One embodiment is an FGF21 analogue comprising one or more of the following modifications, as compared to the polypeptide of SEQ ID NO:1: S6C, S6K, K56R, K59R, K69R, S71C, K122R, I152K, L166F, S167G, M168L, V169aT, P171L, S172E, Q173A, G174V, Y179F, A180E, and/or S181K,R (preferably S6C, S6K, K56R, K59R, K69R, S71C K122R, I152K, and/or M168L). This embodiment includes novel single substitutions in the mature part of FGF21, in numerical order.

One embodiment is an FGF21 analogue comprising one or more of the following modifications, as compared to the polypeptide of SEQ ID NO:1: S6C, S71C, M168L, (S6K, K56R, K59R, K69R, K122R), (K56R, K59R, K69R), (K56R, K69R, K122R), (K59R, K122R), (K56R, K59R, K69R, K122R), (K56R, K59R, K69R, K122R, I152K), and (K56R, K59R, K69R, K122R, L118C-A134C), (L166F, S167G, M168L, V169aT, P171L, S172E, Q173A, G174V, Y179F, A180E, S181K), (V169aT, P171L, S172E, Q173A, G174V, Y179F, A180E, S181K), and/or (Y179F, A180E, 5181 R); preferably : S6C, S71C, M168L, (S6K, K56R, K59R, K69R, K122R), (K56R, K59R, K69R), (K56R, K69R, K122R), (K59R, K69R, K122R), (K56R, K59R, K69R, K122R), (K56R, K59R, K69R, K122R, I152K), and/or (K56R, K59R, K69R, K122R, L118C-A134C). This embodiment includes novel analogues of the invention with their constituent single and multiple or combined substitutions in the mature part of FGF21. The single substitutions are listed first, then the combined ones in numerical order after the first substitution, next after an increasing number of substitutions.

One embodiment is an FGF21 analogue comprising Y179F, A180E and S181K or S181R (i); preferably additionally comprising V169aT, P171L, S172E, Q173A and G174V (ii); more preferably additionally comprising L166F, S167G and M168L (iii); most preferably comprising (i), (ii) and (iii).

In one embodiment, the FGF21 analogue of any of the above embodiments may further include a Met at position −1 of SEQ ID NO:1.

One embodiment is an FGF21 analogue selected from amongst the following: (I) Met-Gly-FGF21, (m) Met-Gly-FGF21-M168L, (n) Met-Cys-FGF21, (o) Gly-FGF21-M168L, (p) Gly-FGF21, (q) Met-Ser-FGF21, or (r) Ser-FGF21; wherein FGF21 designates the polypeptide of SEQ ID NO:1.

One embodiment is an FGF21 analogue which has an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are glycine or serine.

One embodiment is an FGF21 analogue which comprises the following N-terminal extensions as compared to SEQ ID NO:1: (q) MS-FGF21, (s) MSGSGSGSGSG-, (t) MGGGGG-, (u) MSHSGSGSGSGSGSGSGSG-, (v) MSGGGGG-, (x) MSGSGGS-, (y) MSGGSSG-, and (z) MSGSGSG-; as well as any one of the embodiments (q), (s), (t), (u), (v), (x), (y), and (z) without the N-terminal Met.

One embodiment is an FGF21 analogue which is selected from amongst the following: (r) MSGSGSGSGSG-FGF21, (s) MGGGGG-FGF21, (t) MSHSGSGSGSGSGSGSGSG-FGF21, (u) MSGGGGG-FGF21, (v) MSGSGGS-FGF21, (x) MSGGSSG-FGF21, and (y) MSGSGSG-FGF21, as well as any one of embodiments (r), (s), (t), (u), (v), (x) and (y) without the N-terminal Met; wherein FGF21 refers to SEQ ID NO:1.

One embodiment is the FGF21 analogue of any of the above embodiments which has a P (proline) at position 146, wherein the position number refers to SEQ ID NO:1.

In one embodiment, the FGF21 analogue has a potency of at least 1% relative to the potency of Met-FGF21, wherein the potency is determined by measuring glucose uptake in 3T3-L1 adipocytes.

In one embodiment, the FGF21 analogue has a potency of at least 5%, preferably at least 10%, more preferably at least 20%, even more preferably at least 30%, or most preferably at least 40%, relative to the potency of Met-FGF21.

In one embodiment, the FGF21 analogue has a potency of at least 50%, preferably at least 60%, more preferably at least 70%, even more preferably at least 80%, or most preferably at least 90%, relative to the potency of Met-FGF21.

In one embodiment, the FGF21 analogue has a potency of at least 100%, preferably at least 120%, more preferably at least 140%, even more preferably at least 160%, or most preferably at least 180%, relative to the potency of Met-FGF21.

In one embodiment, the FGF21 analogue has a potency of at least 200%, preferably at least 250%, more preferably at least 300%, even more preferably at least 350%, or most preferably at least 400%, relative to the potency of Met-FGF21.

Potency is determined as described for FGF21 derivatives, above.

The FGF21 analogues of this invention are capable of lowering blood glucose in db/db mice relative to a vehicle control.

In one embodiment, the blood glucose is lowered by at least 1%, preferably by at least 2%, more preferably by at least 3%, even more preferably by at least 4%, or most preferably by at least 5%, based on the mean blood glucose measurements in mM and relative to the corresponding vehicle control, vide the test metjhod in example 10.

The term "stable" or stability refers to potency, determined as described above.

In one embodiment, the potency of the analogue of this invention after incubation with $H_2O_2$ is at least 15%, preferably at least 20%, more preferably at least 30%, even more preferably at least 40%, or most preferably at least 50%, wherein the potency is relative to Met-FGF21 treated in the same way, however without H$_2$O$_2$.

These analogues are preferred for being oxidation stable:

In one embodiment, the analogues comprising the following amendments as compared to FGF21 (SEQ ID NO:1): (i) Met-Gly- at the N-terminus, (ii) M168L, (iii) embodiment (i) and (ii), (iv) Met-Cys- at the N-terminus, (v) Gly- at the N-terminus, (vi) embodiment (v) and (ii), (vii) Met-Ser- at the N-terminus, or (iix) Ser- at the N-terminus; preferably the FGF21 analogue is selected from the following: (l) Met-Gly-FGF21, (m) Met-Gly-FGF21-M168L, (n) Met-Cys-FGF21, (o) Gly-FGF21-M168L, (p) Gly-FGF21, (q) Met-Ser-FGF21, or (r) Ser-FGF21; wherein FGF21 refers to the polypeptide of SEQ ID NO:1—if desired with a P (proline) at position 146.

The FGF21 compounds, including FGF21 analogues, and derivatives of FGF21 compounds can be prepared analogously as described for similar compounds. More specifically, reference is made to the specific working examples below.

Example 1 and 2 below describes the cloning and expression of FGF21 and FGF21 analogues in *E. coli*. Alternatively, FGF21 and FGF21 analogues, optionally with N-terminal extensions, can be expressed in yeast as follows:

FGF21 with N-terminal amino acid extensions can be expressed in *S. cerevisiae*. In one embodiment, this requires strain design in which a strain disrupted in PMT2, PEP4 and YPS1 is created. This strain can be designed using classical techniques relying on homologous recombination allowing specific integration at the respective loci. FGF21 with N-terminal extension is coded for on an *S. cerevisiae* expression vector which can be maintained in S. cerevisiea. To direct the FGF21 analogue to the secretory pathway a pre-pro sequence including a signal peptide (for example the MFalpha pre-pro leader sequence) may be provided in the recombinant expression vector. This sequence is joined to the DNA encoding the FGF21 analogue in correct reading frame. This signal peptide ensures secretion to the media. Upstream and adjacent to the FGF21 analogue sequence a dibasic amino acid sequence is placed ensuring cleavage of the prepro sequence from the FGF21 analogue before secretion to the media. The cleavage is likely to be caused by KEX2 activity. The FGF21 analogue can be harvested from the media.

The derivatives of an FGF compound and the FGF21 analogues can be, if desired, be formulated together with other medicaments such as insulin.

All the embodiments in the following chapter, i.e., embodiments 1-180, are according to claim 1 below, to the extent possible.

Further Particular Embodiments

1. A derivative of an FGF21 compound having an albumin binder of the formula A-B-C-D-E- covalently attached, wherein A- is an element of formula I, II or III:

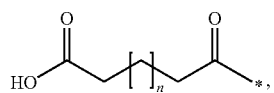 (formula I)

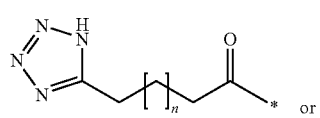 (formula II)

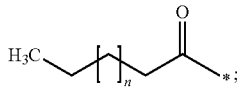 (formula III)

wherein n is 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

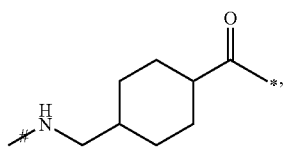 (formula IV or Trx)

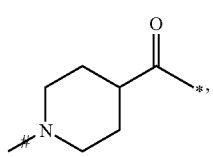 (formula V or Inp)

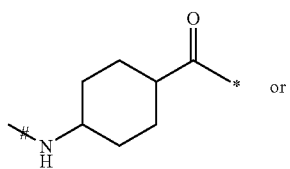 (formula VI)

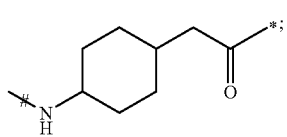 (formula VII)

wherein * is the point of attachment to -B2- or -C-, and # is the point of attachment to A- or -B2-; and -B2- is an element of formula IIX or IX or a combination of up to four elements of formula IIX and/or formula IX:

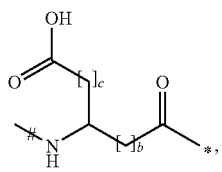 (formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-, or

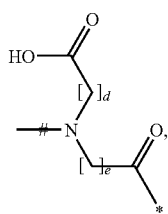
(formula IX)

wherein d is 1 or 2, e is 0, 1 or 2, * is the point of attachment to -C- or -B1-, and # is the point of attachment to A- or -B1-;

-C- is absent, represents a bond or is an element of formula X or XI:

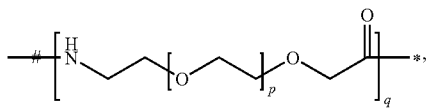
(formula X)

wherein p is 0, 1, 2, 3, 4, 5 or 6, q is 0, 1, 2, 3, 4, 5 or 6, * is the point of attachment to -D-, -E- or the FGF21 compound, and # is the point of attachment to -B-; or

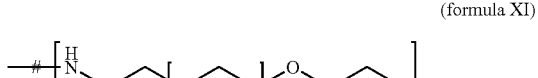
(formula XI)

wherein k is 0, 1, 2, 3, 4, 5, 11 or 23, m is 0, 1, 2, 3, 4, 5 or 6, * is the point of attachment to -D-, -E- or the FGF21 compound; and # is the point of attachment to -B-;

-D- is absent, represents a bond or is an element of formula XII or XIII:

—NH—(CH$_2$)$_r$—NH—CO—(CH$_2$)$_s$—*   (formula XII) or

—NH—(CH$_2$)$_t$—*   (formula XIII), wherein r is 2, 3, 4 or 5, s is 1, 2, 3 or 4, t is 1, 2, 3, 4, 5 or 6, * is the point of attachment to -E- or the FGF21 compound, and # is the point of attachment to -C-;

-E- is absent, represents a bond or an element of formula XXII, XXIII, XXIIIa, XXIV, XXIVa, XXV, XXVI or XXVII:

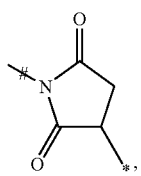
(formula XXII)

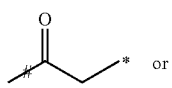
(formula XXIIIa)

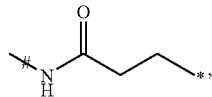
(formula XXIII)

(formula XXIVa) or

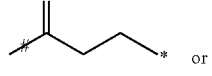
(formula XXIV)

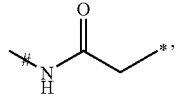
(formula XXV)

(formula XXVI) or

—#—S—*·   (formula XXVII)

wherein * is the point of attachment to the FGF21 compound, and # is the point of attachment to -D- or -C-;

or a pharmaceutically acceptable salt thereof.

2. A derivative of an FGF21 compound having an albumin binder of the formula A-B-C-D-E- covalently attached, wherein A- is an element of formula I, II or III:

(formula I)

(formula II)

(formula III)

wherein n is 10, 11, 12, 13, 14, 15, 16, 17, 18 or 19, and * is the point of attachment to -B-;

-B- is absent, represents a bond or is selected from -B1-, -B2- or combinations thereof, wherein
-B1- is an element of formula IV, V, VI or VII:

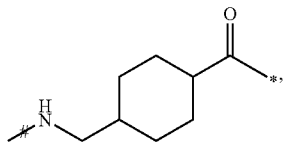
(formula IV or Trx)

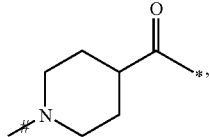
(formula V or Inp)

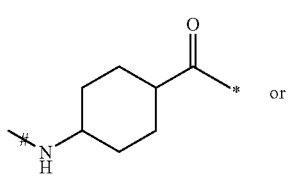
(formula VI) or

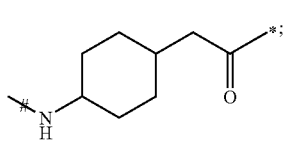
(formula VII)

wherein * is the point of attachment to -B2- or -C-, and # is the point of attachment to A- or -B2-; and
-B2- is an element of formula IIX or IX or a combination of up to four elements of formula IIX and/or formula IX and or formula XXVII:

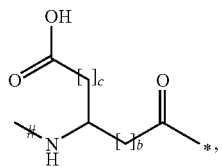
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-, or

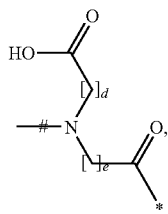
(formula IX)

wherein d is 1 or 2, e is 0, 1 or 2, * is the point of attachment to -C- or -B1-, and # is the point of attachment to A- or -B1- or

—NH—SO$_2$—(CH$_2$)$_u$—CO—*  (formula XXVIII)

wherein u is 2, 3 or 4, * is the point of attachment to -C- or -B1-, and # is the point of attachment to A- or -B1-;
-C- is absent, represents a bond or is an element of formula X or XI:

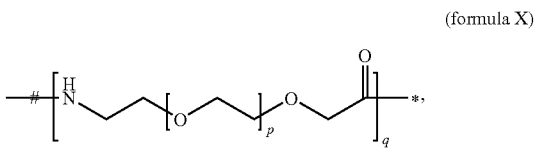
(formula X)

wherein p is 0, 1, 2, 3, 4, 5 or 6, q is 0, 1, 2, 3, 4, 5 or 6, * is the point of attachment to -D-, -E- or the FGF21 compound, and # is the point of attachment to -B-; or

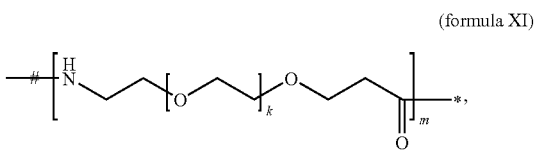
(formula XI)

wherein k is 0, 1, 2, 3, 4, 5, 11 or 23, m is 0, 1, 2, 3, 4, 5 or 6, * is the point of attachment to -D-, -E- or the FGF21 compound; and # is the point of attachment to -B-;
-D- is absent, represents a bond or is an element of formula XII or XIII:

—NH—(CH$_2$)$_r$—NH—CO—(CH$_2$)$_s$—*  (formula XII) or

—NH—(CH$_2$)$_t$—*  (formula XIII), wherein r is 2, 3, 4 or 5, s is 1, 2, 3 or 4, t is 1, 2, 3, 4, 5 or 6, * is the point of attachment to -E- or the FGF21 compound, and # is the point of attachment to -C-;
-E- is absent, represents a bond or an element of formula XXII, XXIII, XXIIIa, XXIV, XXIVa, XXV, XXVI or XXVII:

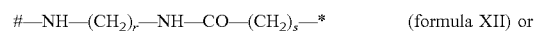
(formula XXII)

(formula XXIIIa)

(formula XXIII)

(formula XXIVa)

or (formula XXIV)

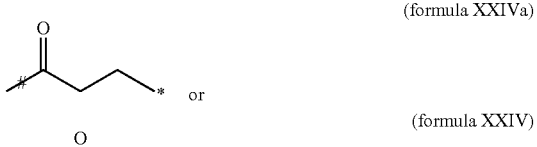

-continued

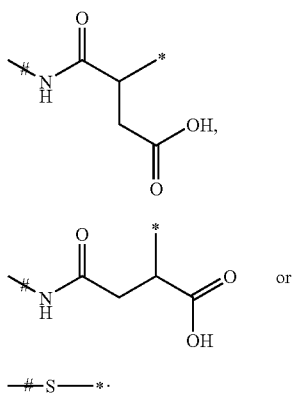
(formula XXV)

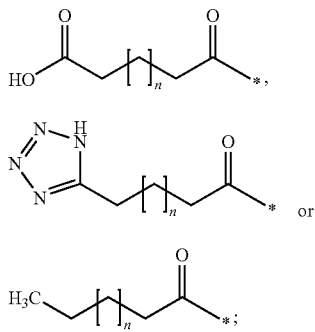
(formula XXVI)

—#—S—*.
(formula XXVIII)

wherein * is the point of attachment to the FGF21 compound, and # is the point of attachment to -D- or -C-; or a pharmaceutically acceptable salt thereof.

3. The derivative of embodiment 1 or 2, wherein if A is an element of formula (III), then at least one of -B-, -C-, -D- and -E- is present and/or does not represent a bond.
4. The derivative of any one of the preceding embodiments to the extent possible, wherein -B- and -C- are present and do not represent a bond.
5. A derivative of an FGF21 compound having an albumin binder of the formula A-B-C-D-E- covalently attached, according to any one of the preceding embodiments to the extent possible, wherein A- is an element of formula I, II or III:

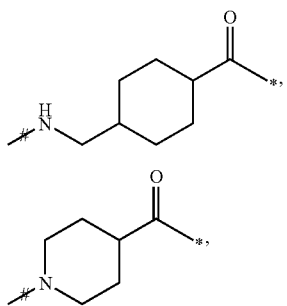
(formula I)

(formula II)

(formula III)

wherein n is 10, 11, 12, 13, 14, 15, 16, 17, 18 or 19, and * is the point of attachment to -B-;
-B- is -B1-, -B2- or combinations thereof, wherein
-B1- is an element of formula IV, V, VI or VII:

(formula IV or Trx)

(formula V or Inp)

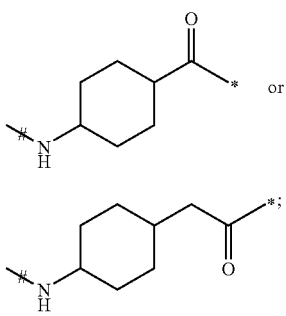
(formula VI)

(formula VII)

wherein * is the point of attachment to -B2- or -C-, and # is the point of attachment to A- or -B2-; and
-B2- is an element of formula IIX, IX or XXVIII or a combination of up to four elements of formula IIX and/or formula IX and/or formula XXVIII:

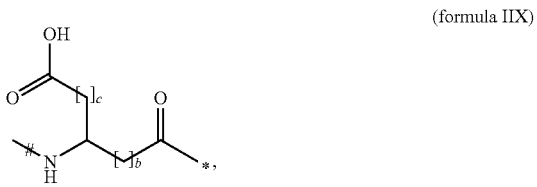
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-,

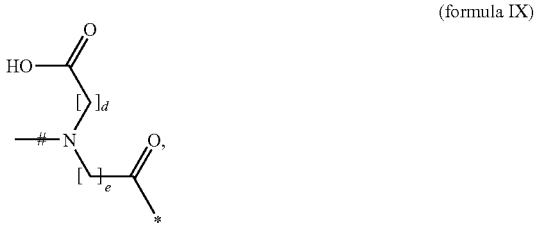
(formula IX)

wherein d is 1 or 2, e is 0, 1 or 2, * is the point of attachment to -C- or -B1-, and # is the point of attachment to A- or -B1-; or \#—NH—SO$_2$—(CH$_2$)$_u$—CO—*  (formula XXVIII)

wherein u is 2, 3 or 4, * is the point of attachment to -C- or -B1-, and # is the point of attachment to A- or -B1-;
-C- is an element of formula X or XI:

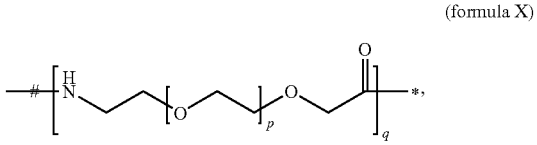
(formula X)

wherein p is 0, 1, 2, 3, 4, 5 or 6, q is 0, 1, 2, 3, 4, 5 or 6, * is the point of attachment to -D-, -E- or the FGF21 compound, and # is the point of attachment to -B-; or

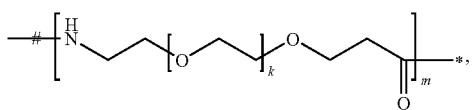
(formula XI)

wherein k is 0, 1, 2, 3, 4, 5, 11 or 23, m is 0, 1, 2, 3, 4, 5 or 6, * is the point of attachment to -D-, -E- or the FGF21 compound; and # is the point of attachment to -B-;

-D- is optional, and when present an element of formula XII or XIII:

—NH—(CH$_2$)$_r$—NH—CO—(CH$_2$)$_s$—*   (formula XII) or

—NH—(CH$_2$)$_t$—*   (formula XIII), wherein r is 2, 3, 4 or 5, s is 1, 2, 3 or 4, t is 1, 2, 3, 4, 5 or 6, * is the point of attachment to -E- or the FGF21 compound, and # is the point of attachment to -C-;

-E- is optional, and when present a bond or an element of formula XXII, XXIII, XXIIIa, XXIV, XXIVa, XXV, XXVI or XXVII:

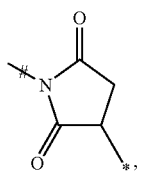
(formula XXII)

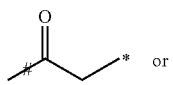
(formula XXIIIa)

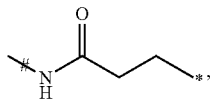
(formula XXIII)

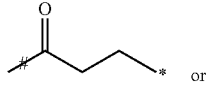
(formula XXIVa)

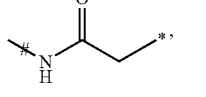
(formula XXIV)

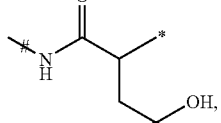
(formula XXV)

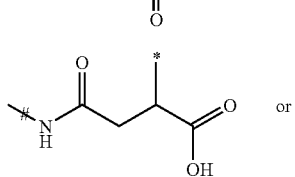
(formula XXVI)

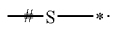
(formula XXVII)

wherein * is the point of attachment to the FGF21 compound, and # is the point of attachment to -D- or -C-;

or a pharmaceutically acceptable salt thereof.

6. A derivative of an FGF21 compound having an albumin binder of the formula A-B-C-D-E- covalently attached, according to any one of the preceding embodiments to the extent possible, wherein A- is an element of formula I, II or III:

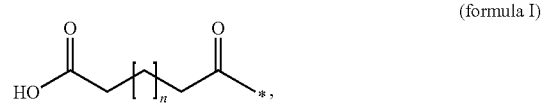
(formula I)

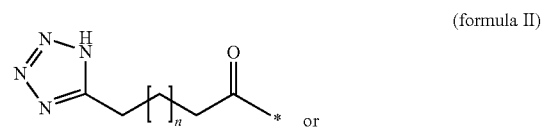
(formula II)

(formula III)

wherein n is 10, 11, 12, 13, 14, 15, 16, 17, 18 or 19, and * is the point of attachment to -B-;

-B- is -B1-, -B2- or combinations thereof, wherein

-B1- is an element of formula IV, V, VI or VII:

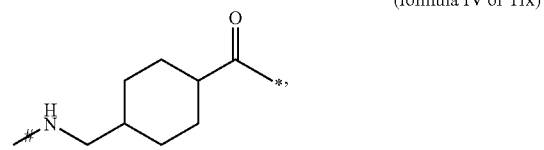
(formula IV or Trx)

(formula V or Inp)

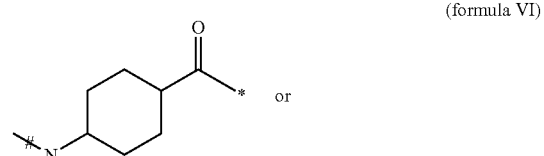
(formula VI)

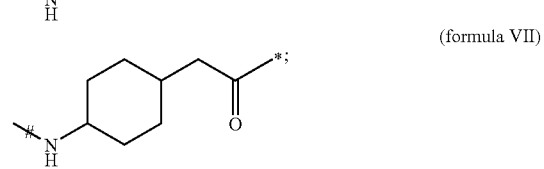
(formula VII)

wherein * is the point of attachment to -B2- or -C-, and # is the point of attachment to A- or -B2-; and -B2- is an element of formula IIX or IX or a combination of up to four elements of formula IIX and/or formula IX:

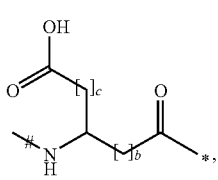
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2- or

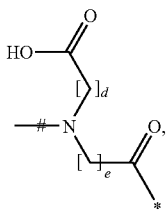
(formula IX)

wherein d is 1 or 2, e is 0, 1 or 2, * is the point of attachment to -C- or -B1-, and # is the point of attachment to A- or -B1-;

-C- is an element of formula X or XI:

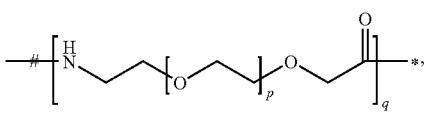
(formula X)

wherein p is 0, 1, 2, 3, 4, 5 or 6, q is 0, 1, 2, 3, 4, 5 or 6, * is the point of attachment to -D-, -E- or the FGF21 compound, and # is the point of attachment to -B-; or

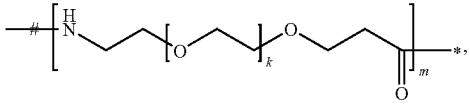
(formula XI)

wherein k is 0, 1, 2, 3, 4, 5, 11 or 23, m is 0, 1, 2, 3, 4, 5 or 6, * is the point of attachment to -D-, -E- or the FGF21 compound; and # is the point of attachment to -B-;

-D- is optional, and when present an element of formula XII or XIII:

—NH—(CH₂)ᵣ—NH—CO—(CH₂)ₛ—*  (formula XII) or

—NH—(CH₂)ₜ—*  (formula XIII), wherein r is 2, 3, 4 or 5, s is 1, 2, 3 or 4, t is 1, 2, 3, 4, 5 or 6, * is the point of attachment to -E- or the FGF21 compound, and # is the point of attachment to -C-;

-E- is optional, and when present a bond or an element of formula XXII, XXIII, XXIIIa, XXIV, XXIVa, XXV, XXVI or XXVII:

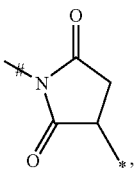
(formula XXII)

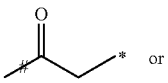
(formula XXIIIa)

or

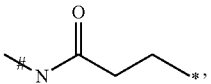
(formula XXIII)

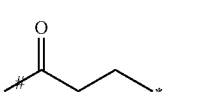
(formula XXIVa)

or

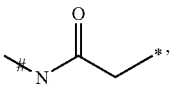
(formula XXIV)

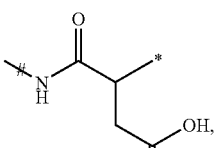
(formula XXV)

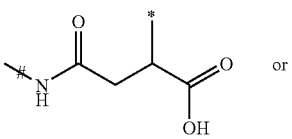
(formula XXVI)

or

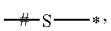
(formula XXVII)

wherein * is the point of attachment to the FGF21 compound, and # is the point of attachment to -D- or -C-;

or a pharmaceutically acceptable salt thereof.

7. A derivative of an FGF21 compound having an albumin binder of the formula A-B-C-D-E- covalently attached to a thiol group of the FGF21 compound, according to any one of the preceding embodiments to the extent possible, wherein A- is an element of formula I, II or III:

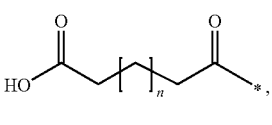
(formula I)

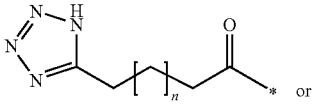
(formula II)

or

-continued

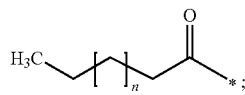
(formula III)

wherein n is 10, 11, 12, 13, 14, 15, 16, 17, 18 or 19, and * is the point of attachment to -B-;

-B- is -B1-, -B2- or combinations thereof, wherein

-B1- is an element of formula IV, V, VI or VII:

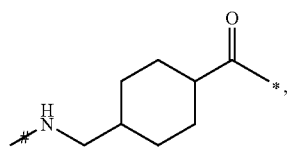
(formula IV or Trx)

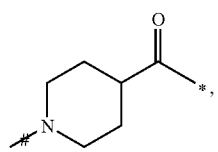
(formula V or Inp)

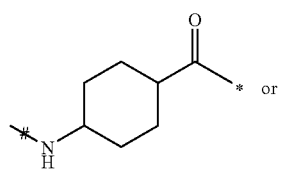
(formula VI) * or

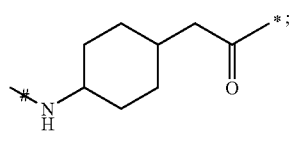
(formula VII)

wherein * is the point of attachment to -B2- or -C-, and # is the point of attachment to A- or -B2-; and -B2- is an element of formula IIX or IX or a combination of up to four elements of formula IIX and/or formula IX:

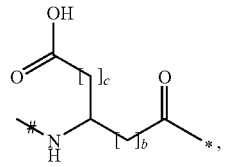
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2- or

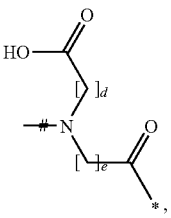
(formula IX)

wherein d is 1 or 2, e is 0, 1 or 2, * is the point of attachment to -C- or -B1-, and # is the point of attachment to A- or -B1-;

-C- is an element of formula X or XI:

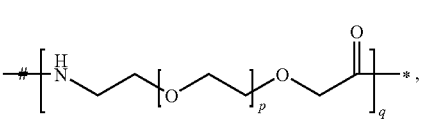
(formula X)

wherein p is 0, 1, 2, 3, 4, 5 or 6, q is 0, 1, 2, 3, 4, 5 or 6, * is the point of attachment to -D-, -E- or the FGF21 compound, and # is the point of attachment to -B-; or

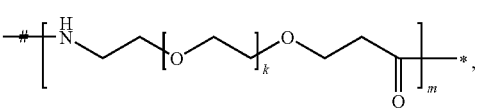
(formula XI)

wherein k is 0, 1, 2, 3, 4, 5, 11 or 23, m is 0, 1, 2, 3, 4, 5 or 6, * is the point of attachment to -D-, -E- or the FGF21 compound; and # is the point of attachment to -B-;

-D- is an element of formula XII or XIII:

—NH—(CH$_2$)$_r$—NH—CO—(CH$_2$)$_s$—*  (formula XII) or

—NH—(CH$_2$)$_t$—*  (formula XIII), wherein r is 2, 3, 4 or 5, s is 1, 2, 3 or 4, t is 1, 2, 3, 4, 5 or 6, * is the point of attachment to -E- or the FGF21 compound, and # is the point of attachment to -C-;

-E- is an element of formula XXII, XXIII, XXIIIa, XXIV, XXIVa, XXV, XXVI or XXVII;

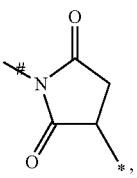
(formula XXII)

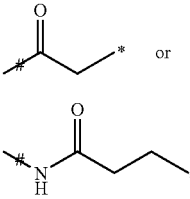
(formula XXIIIa)
or

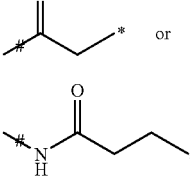
(formula XXIII)

-continued

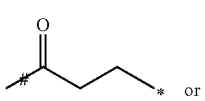 or

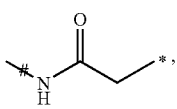

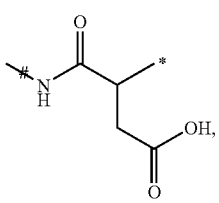

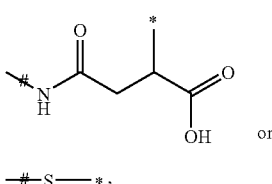 or

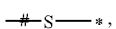

wherein * is the point of attachment to the FGF21 compound, and # is the point of attachment to -D- or -C-;
or a pharmaceutically acceptable salt thereof.

8. The derivative according to any one of the preceding embodiments to the extent possible, especially according to the preceding embodiment, wherein -E- is an element of formula XXII, XXIII, XXIV, XXV, XXVI or XXVII

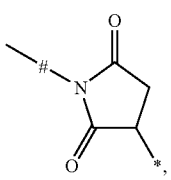 (formula XXII)

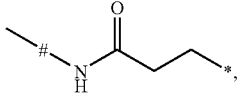 (formula XXIII)

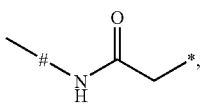 (formula XXIV)

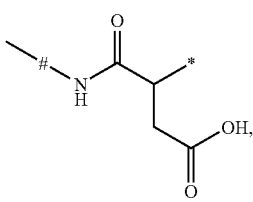 (formula XXV)

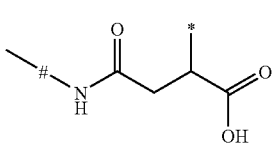 or (formula XXVI)

 (formula XXVII)

wherein * is the point of attachment to the FGF21 compound, and # is the point of attachment to -D- or -C-.

9. The derivative according to any one of the preceding embodiments to the extent possible, in which A- is an element of formula I:

 (formula I)

wherein n is as defined herein.

10. The derivative according to any one of the preceding embodiments to the extent possible, in which n is 14, 16 or 18, preferably 14 or 16.

11. The derivative according to any one of the preceding embodiments to the extent possible, in which A- is an element of formula I, preferably one wherein n is 13.

12. The derivative according to any one of the preceding embodiments to the extent possible, in which -B- comprises -B1-, preferably an element of formula IV or V:

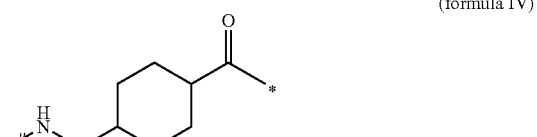 (formula IV)

or (formula V)

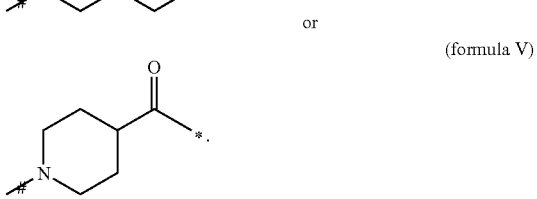

13. The derivative according to any one of the preceding embodiments to the extent possible, in which -B- comprises -B2-, preferably one or two elements of formula IIX:

 (formula IIX)

in which more preferably c is 0 and b is 2 or c is 0 and b is 1.

14. The derivative according to any one of the preceding embodiments to the extent possible, in which -B- is -B2-, more precisely an element of formula IX, (formula IX)

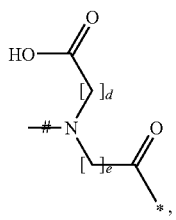

preferably one wherein d is 1 and e is 2.

15. The derivative according to any one of the preceding embodiments to the extent possible, in which -B- is a bond.

16. The derivative according to any one of the preceding embodiments to the extent possible, in which -C- is an element of formula X:

(formula X)

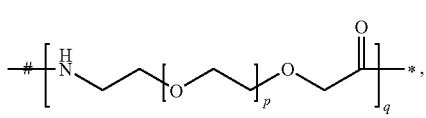

in which preferably q is 0, 1, 2, 3 or 4, more preferably q is 1 or 2, and even more preferred q is 2.

17. The derivative according to any one of the preceding embodiments to the extent possible, in which -C- is an element of formula X:

(formula X)

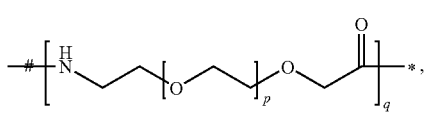

in which preferably p is 1 or 2, more preferably p is 1.

18. The derivative according to any one of the preceding embodiments to the extent possible, in which p is 1 and q is 1 or 2, preferably p is 1 and q is 2.

19. The derivative according to any one of the preceding embodiments to the extent possible, in which in which -C- is an element of formula XI:

(formula XI)

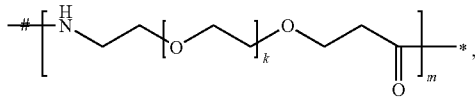

in which preferably m is 0, 1 or 2, more preferably m is 1 or 2.

20. The derivative according to any one of the preceding embodiments to the extent possible, in which in which -C- is an element of formula XI:

(formula XI)

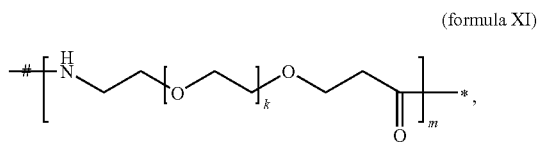

in which preferably k is 1, 2, 3, 4, 5 or 11, more preferably k is 5.

21. The derivative according to any one of the preceding embodiments to the extent possible, in which m is 1 and k is 4, 5 or 11, preferably m is 1 and k is 5.

22. The derivative according to any one of the preceding embodiments to the extent possible, in which -D- is an element of formula XII:

—NH—(CH$_2$)$_r$—NH—CO—(CH$_2$)$_s$*   (formula XII), in which preferably r is 2, and/or in which preferably s is 1 or 2, most preferably r is 2 and s is 2.

23. The derivative according to any one of the preceding embodiments to the extent possible, in which -D- is an element of formula XIII:

—NH—(CH$_2$)$_t$—*   (formula XIII), in which preferably t is 1, 2 or 3, more preferably t is 2.

24. The derivative according to any one of the preceding embodiments to the extent possible, in which -D- is absent.

25. The derivative according to any one of the preceding embodiments to the extent possible, in which -E- is an element of formula XXII, XXIII, XXIV, XXV, XXVI or XXVII:

(formula XXII)

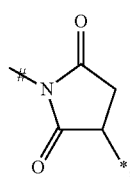

(formula XXIII)

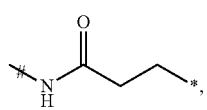

(formula XXIV)

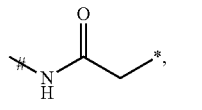

(formula XXV)

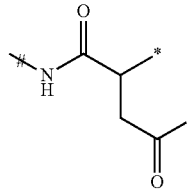

(formula XXVI)

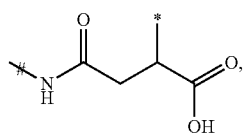

-continued

  (formula XXVII)

or a bond.

26. The derivative according to any one of the preceding embodiments to the extent possible, in which -E- is an element of formula XXII, XXIII, XXIIIa, XXV or XXVI:

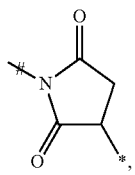  (formula XXII)

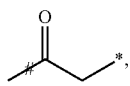  (formula XXIIIa)

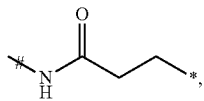  (formula XXIII)

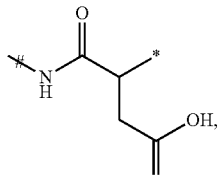  (formula XXV)

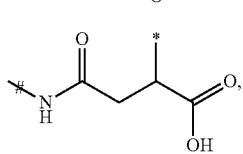  (formula XXVI)

or a bond.

27. The derivative according to any one of the preceding embodiments to the extent possible, in which -E- is an element of formula XXIV.

28. The derivative according to any one of the preceding embodiments to the extent possible, having one or two albumin binders of the formula A-B-C-D-E-.

29. The derivative according to any one of the preceding embodiments to the extent possible, having an albumin binders of the formula A-B-C-D-E- wherein A- is an element of formula I or II, -B- is a bond or an element of formula IIX or IX, -C- is an element of formula X, -D- is an element of formula XII or XIII, and -E- is an element of formula XXII or XXIV, and, preferably, n is 13, 14 or 16, b is 2, d is 1, e is 2, p is 1, q is 2, r is 2, s is 2, and t is 2.

30. The derivative according to any one of the preceding embodiments to the extent possible, which has two albumin binders.

31. The derivative according to any one of the preceding embodiments to the extent possible, wherein A- is an element of formula I, II or III:

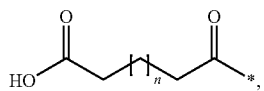  (formula I)

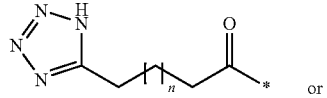  (formula II)

or

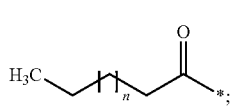  (formula III)

wherein n is 10, 11, 12 or 13.

32. The derivative according to any one of the preceding embodiments to the extent possible, wherein A- is an element of formula I, II or Ill:

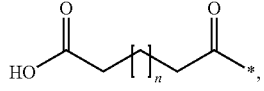  (formula I)

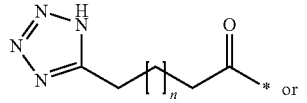  (formula II)

or

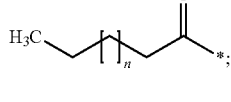  (formula III)

wherein n is 8, 9, 10, 11, 12 or 13.

33. The derivative according to any one of the preceding embodiments to the extent possible, which has one albumin binder.

34. The derivative according to any one of the preceding embodiments to the extent possible, wherein A- is an element of formula I, II or Ill:

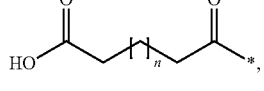  (formula I)

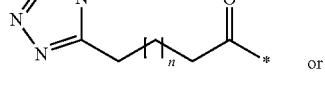  (formula II)

or

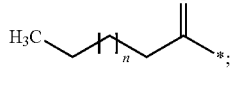  (formula III)

wherein n is 14, 15, 16, 17, 18 or 19.

35. The derivative according to any one of the preceding embodiments to the extent possible, wherein A- is an element of formula I, II or Ill:

(formula I)
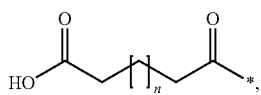
(formula II)
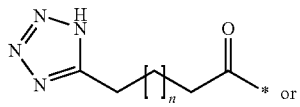  or
(formula III)
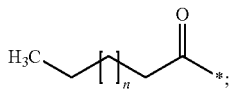
wherein n is 12, 13, 14, 15, 16, 17 or 18.
36. A derivative of an FGF21 compound having an albumin binder of the formula A-B-C-D-E- covalently attached according to any one of the preceding embodiments to the extent possible, wherein A-B-C-D-E- is selected from the following formulas (1)-(14):
(1):
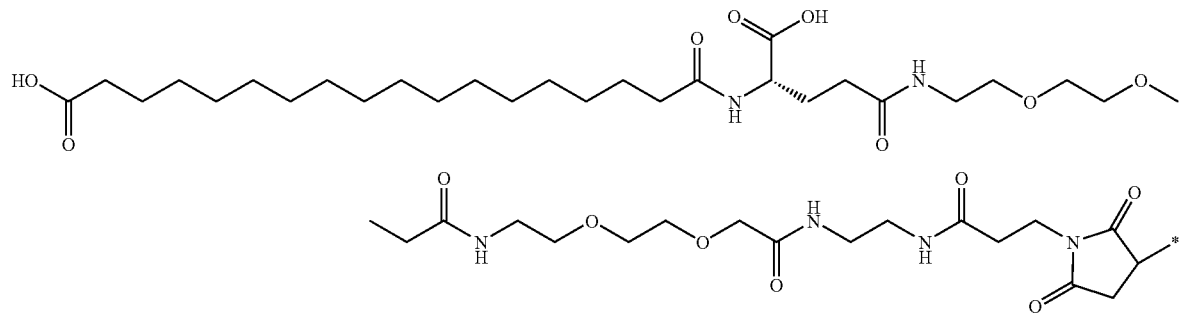
(2):
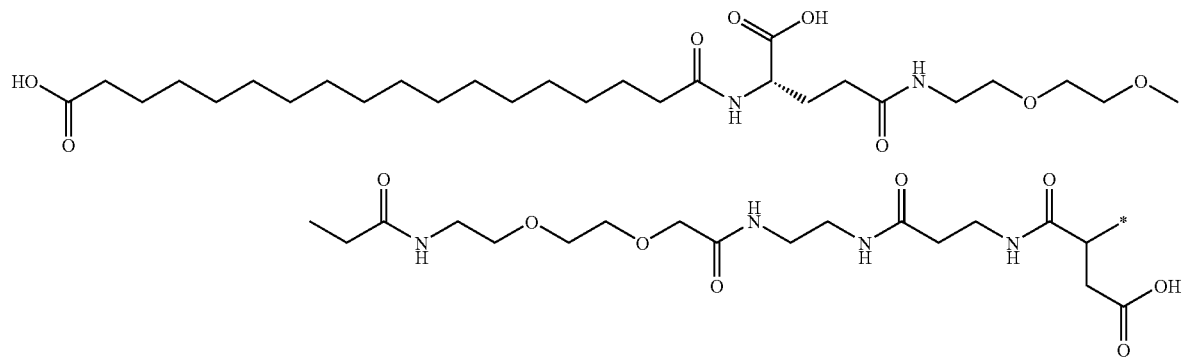
(3):
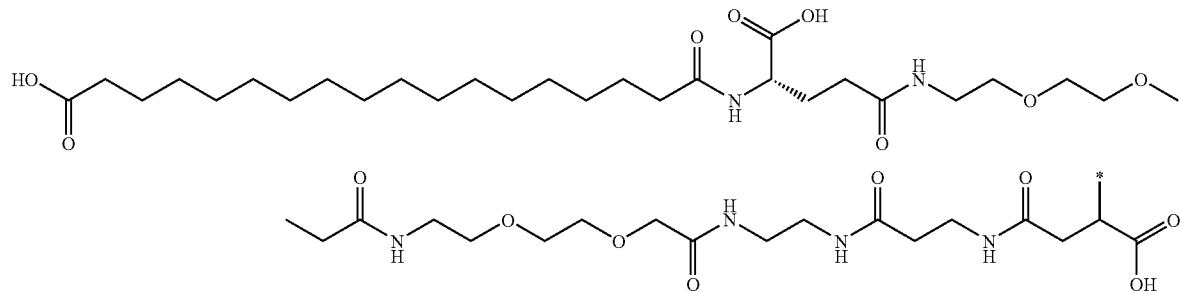

(4):
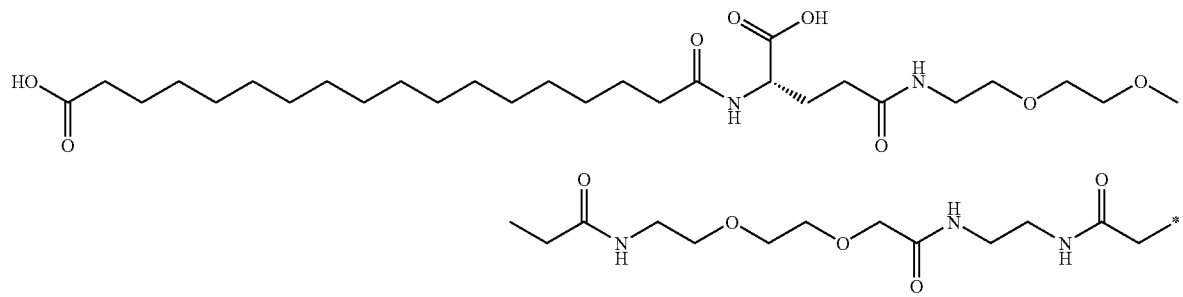
(5):
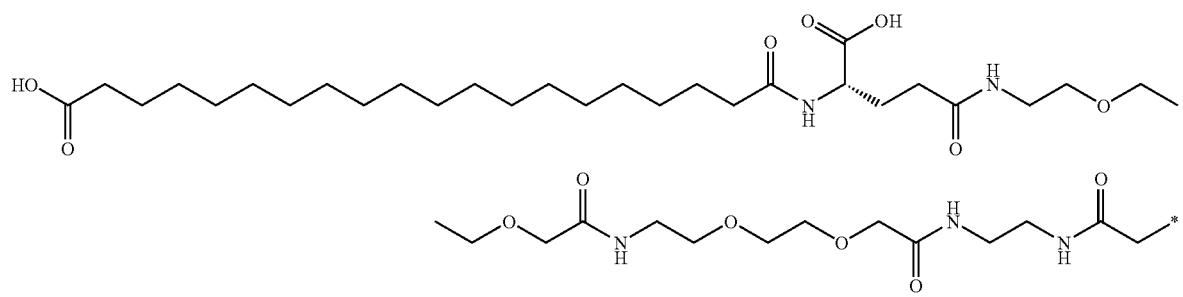
(6):
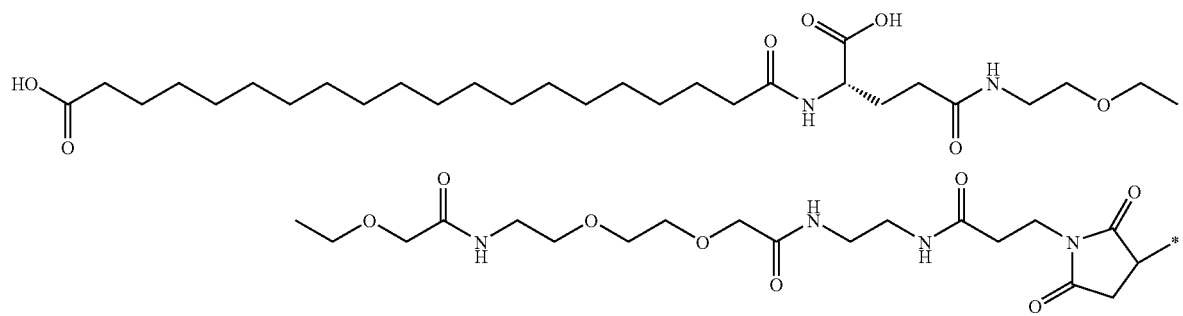
(7):
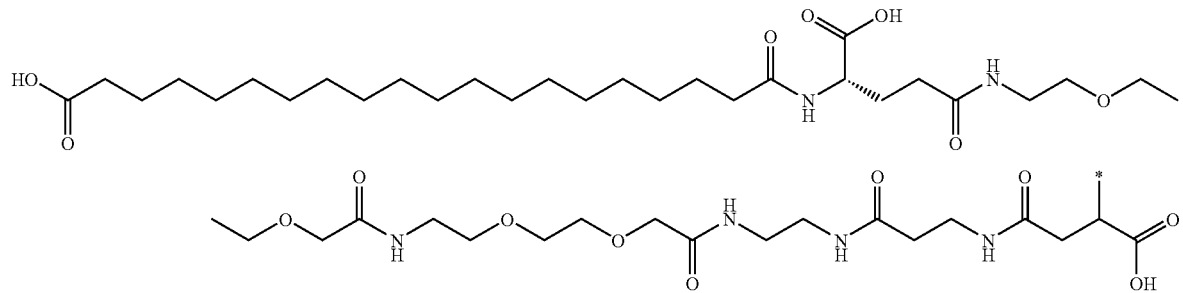

(8):
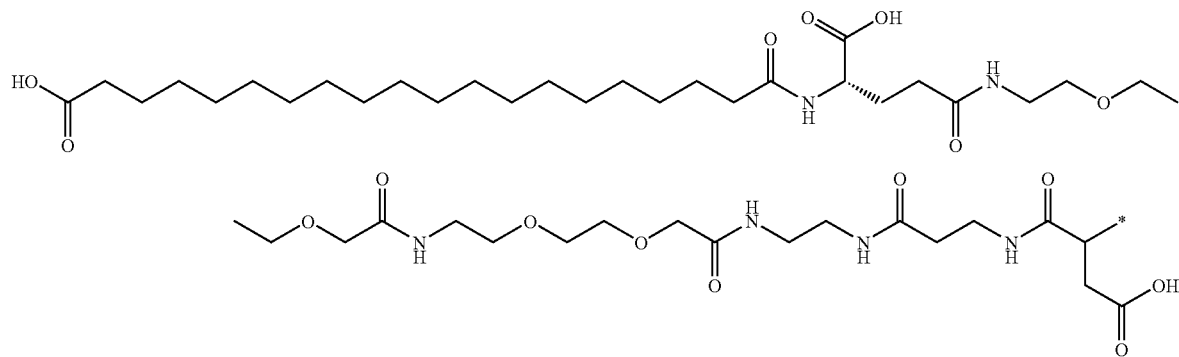
(9):
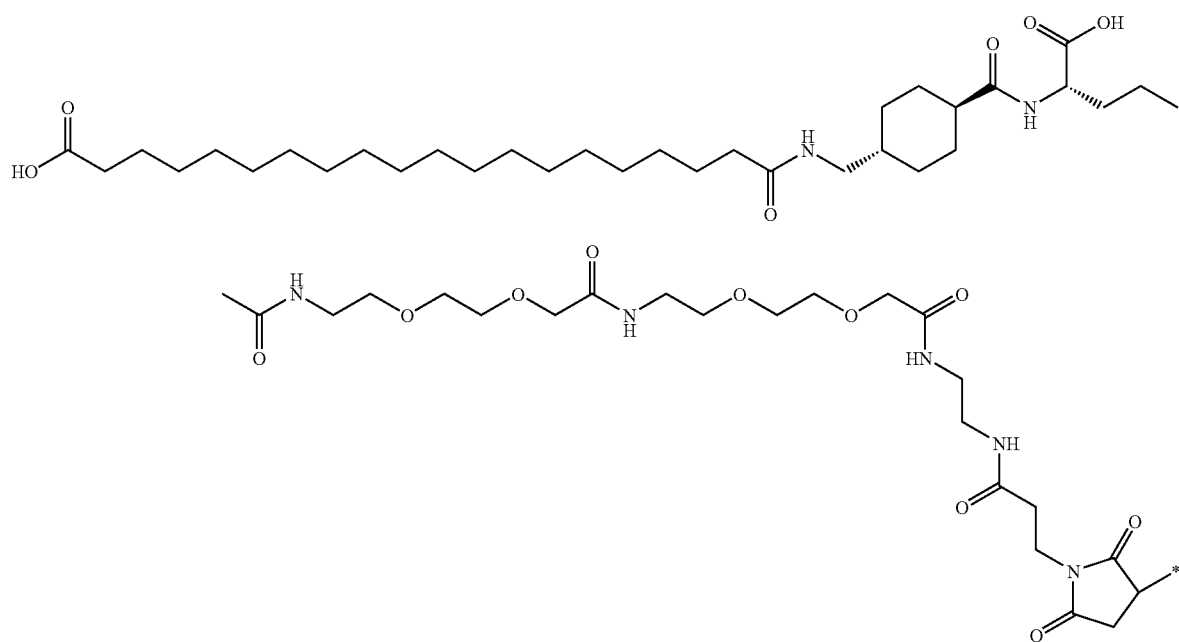
(10):
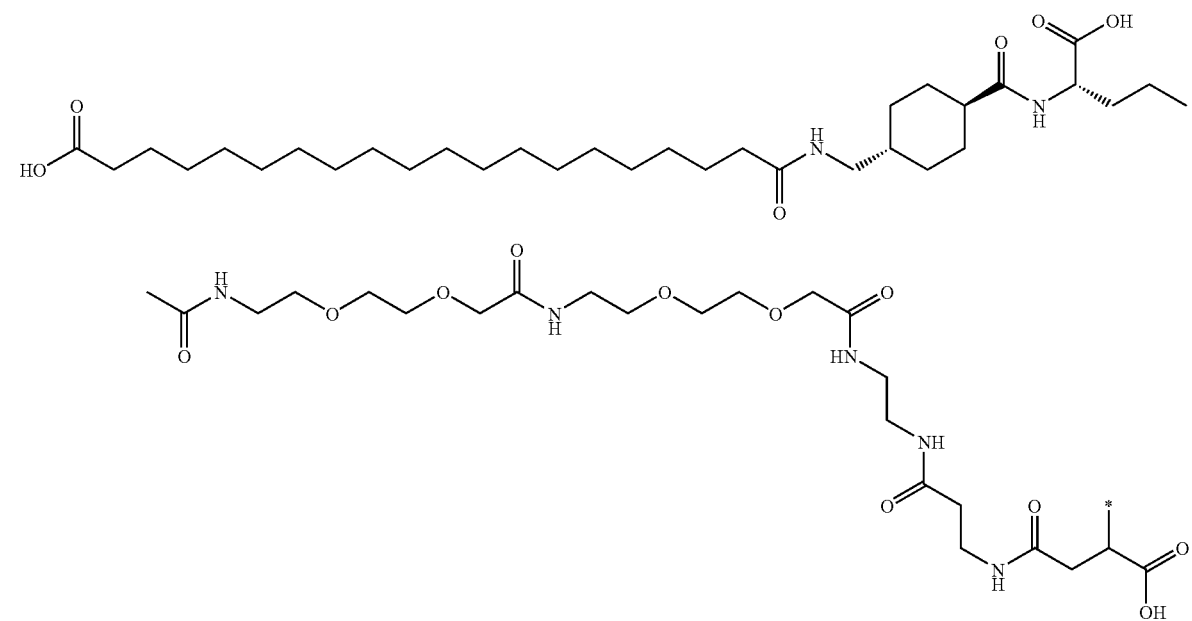

(11):
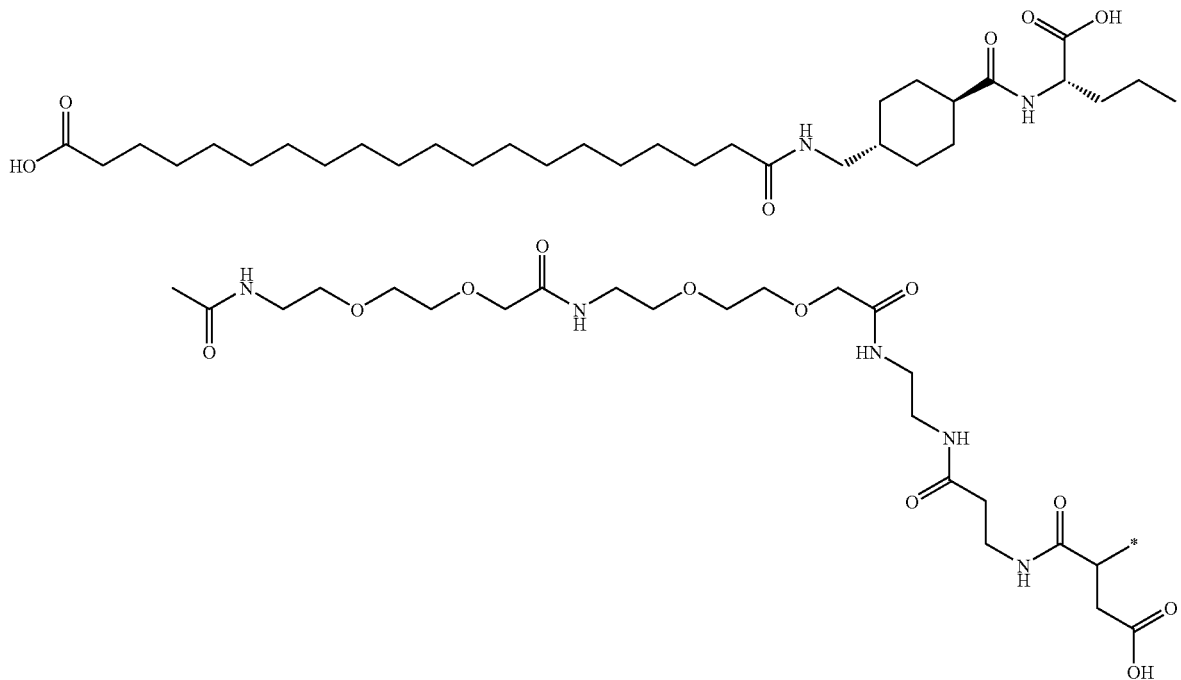
(12):
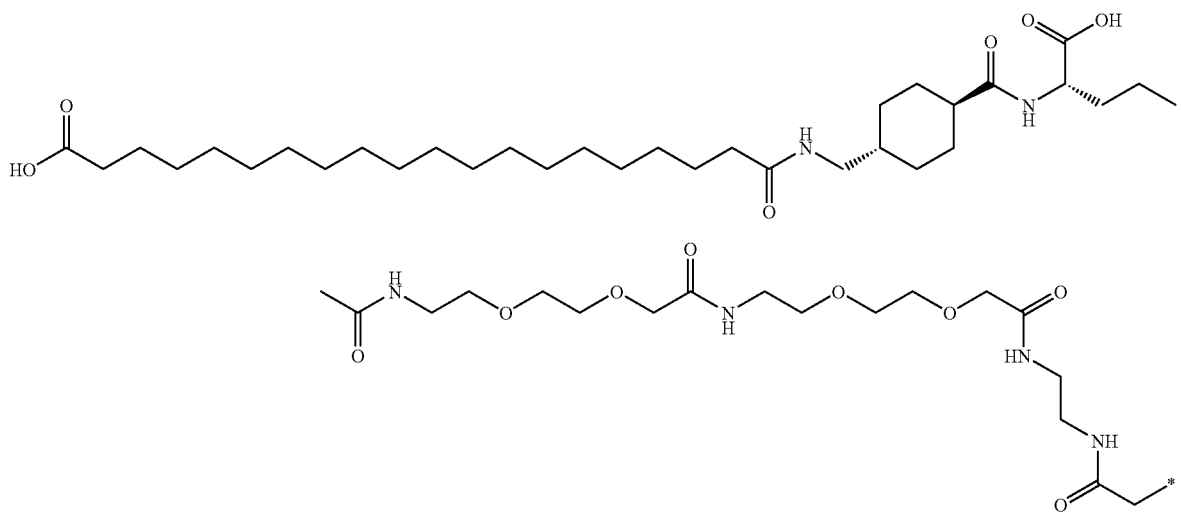
(13):
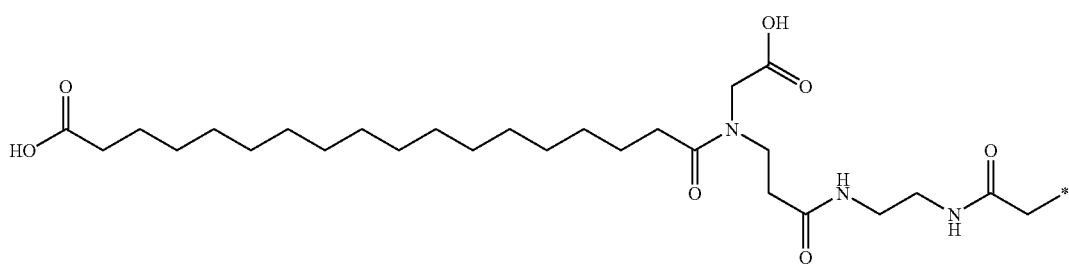

(14):
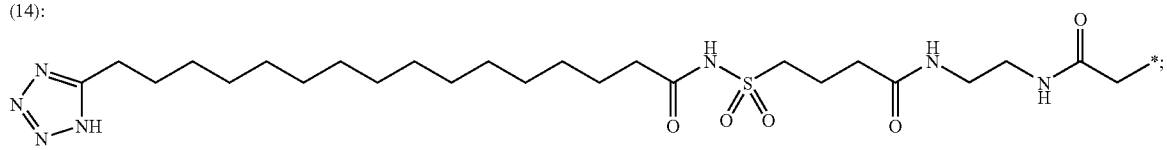
or a pharmaceutically acceptable salt of any one of the corresponding derivatives.
37. A derivative of an FGF21 compound having an albumin binder of the formula A-B-C-D-E- covalently attached according to any one of the preceding embodiments to the extent possible, wherein A-B-C-D-E- is selected from the following formulas (1)-(12):
(1):
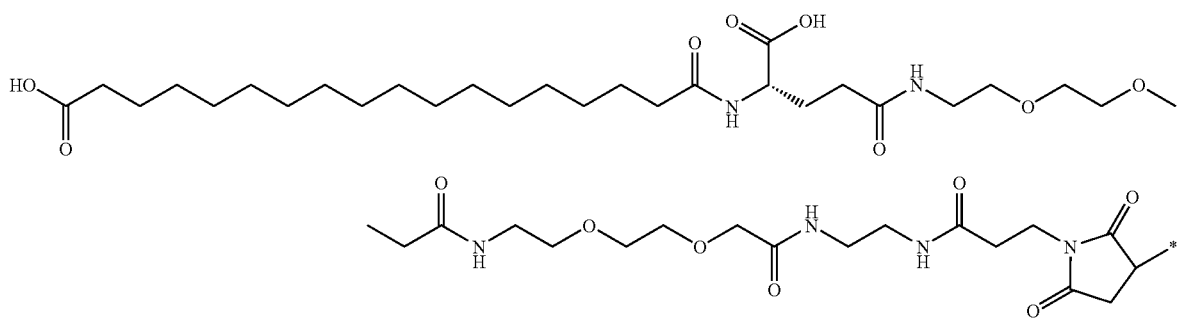
(2):
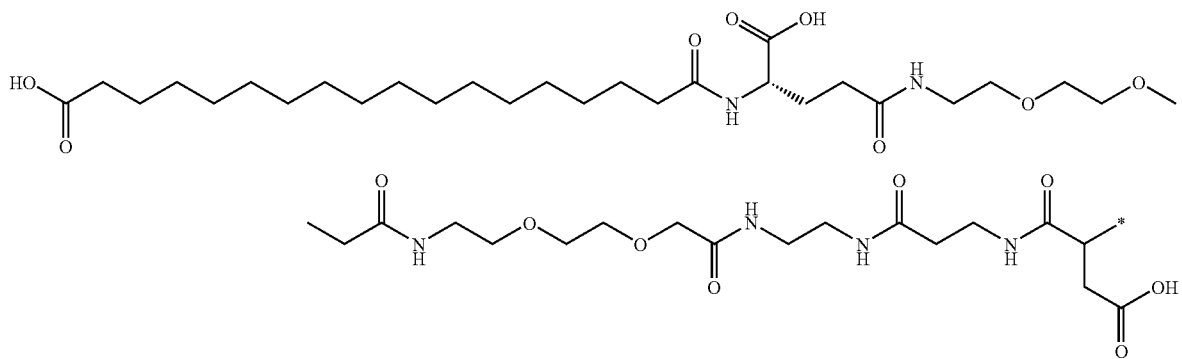
(3):
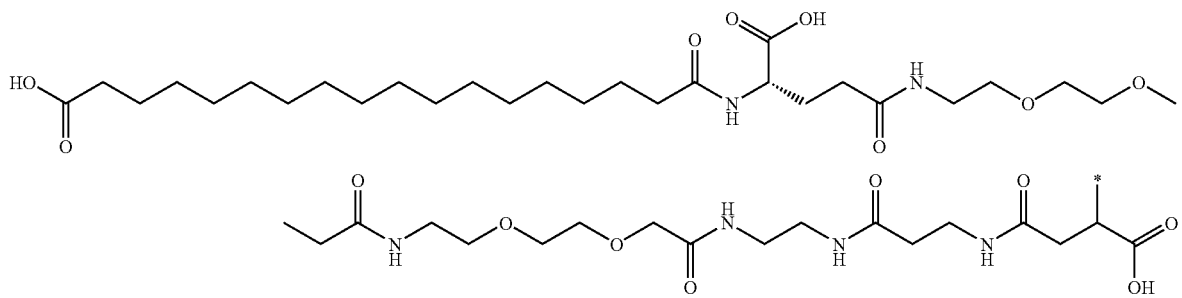

-continued
(4):
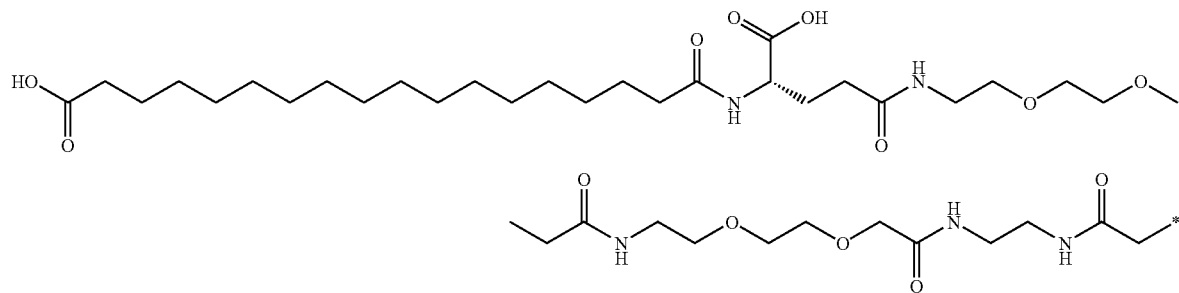
(5):
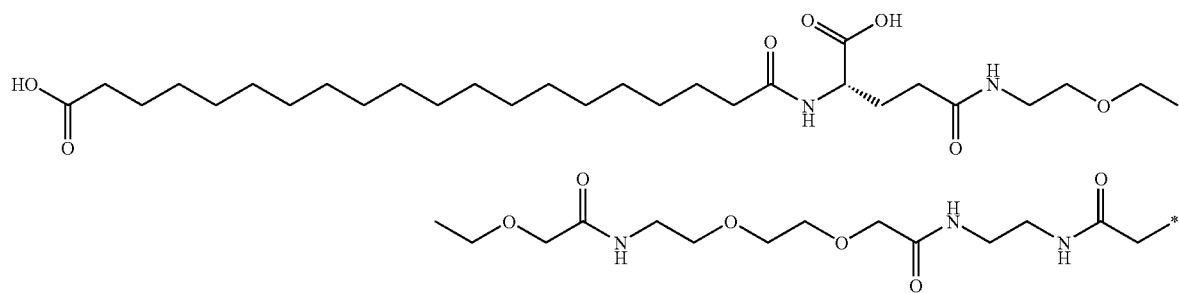
(6):
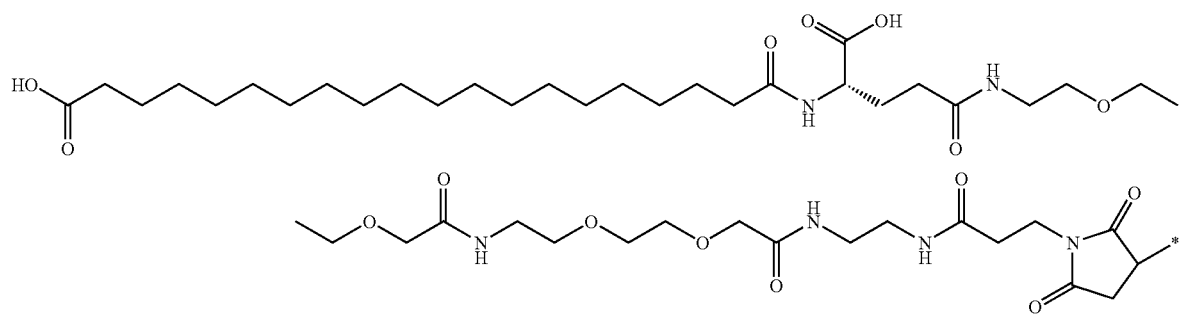
(7):
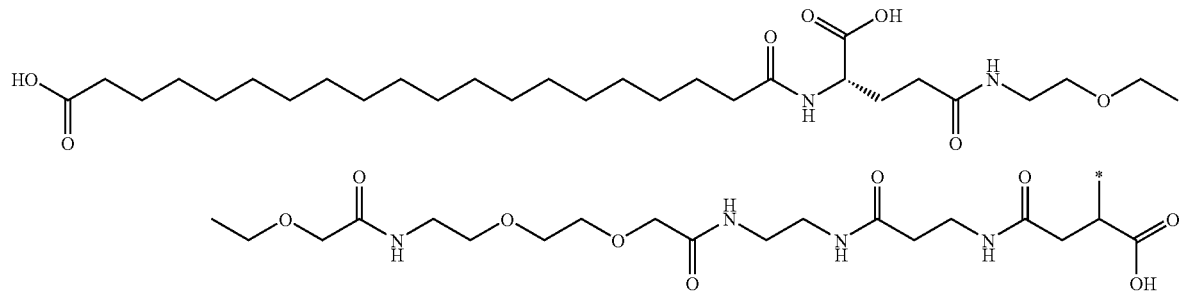

(8):
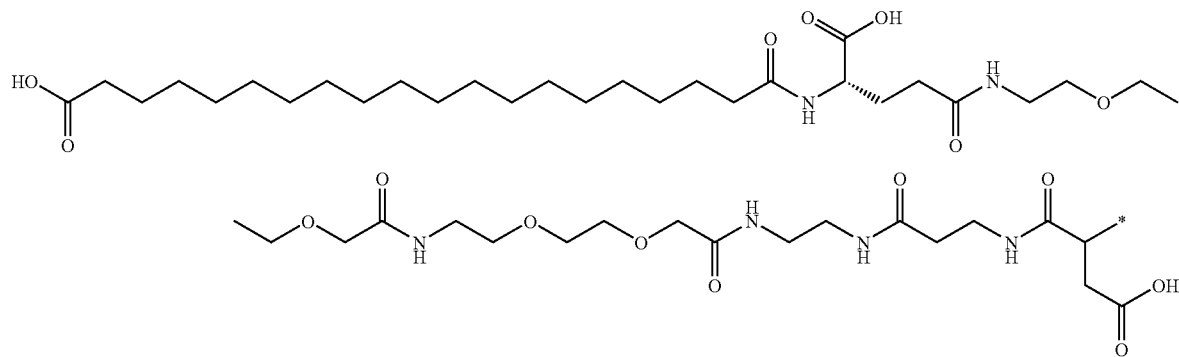
(9):
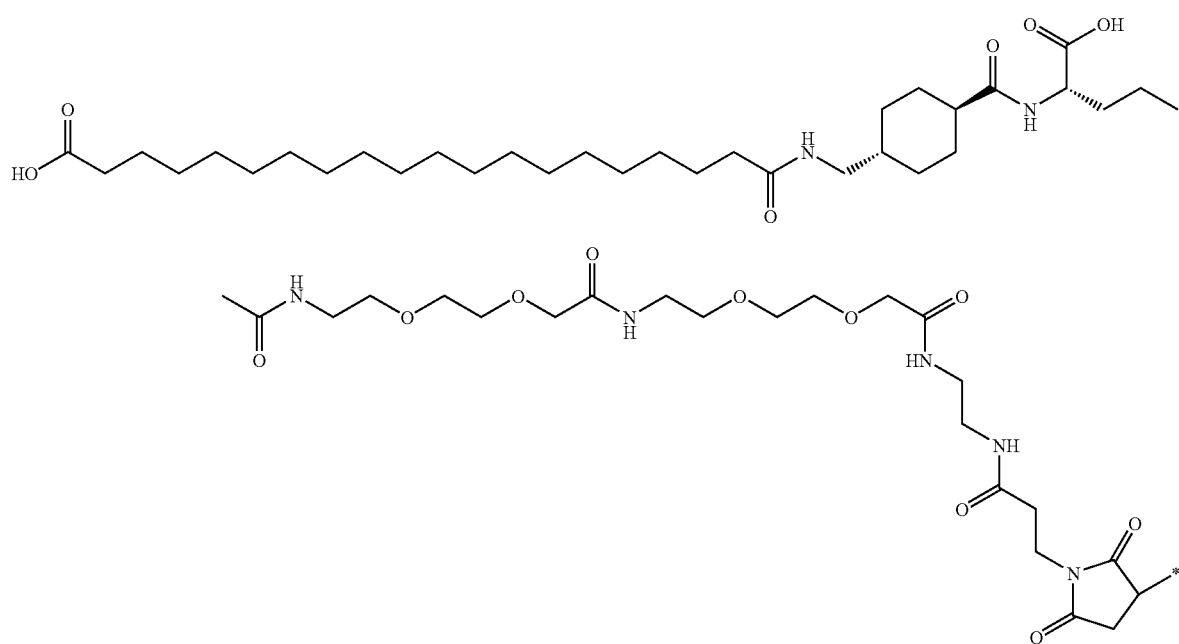
(10):
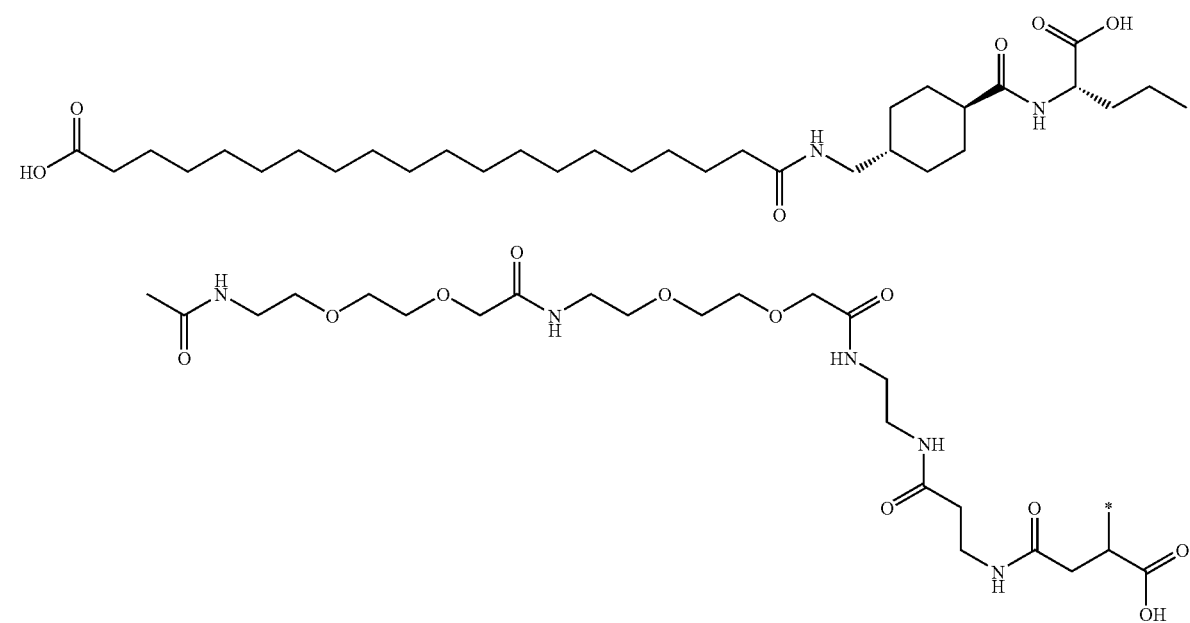

(11):

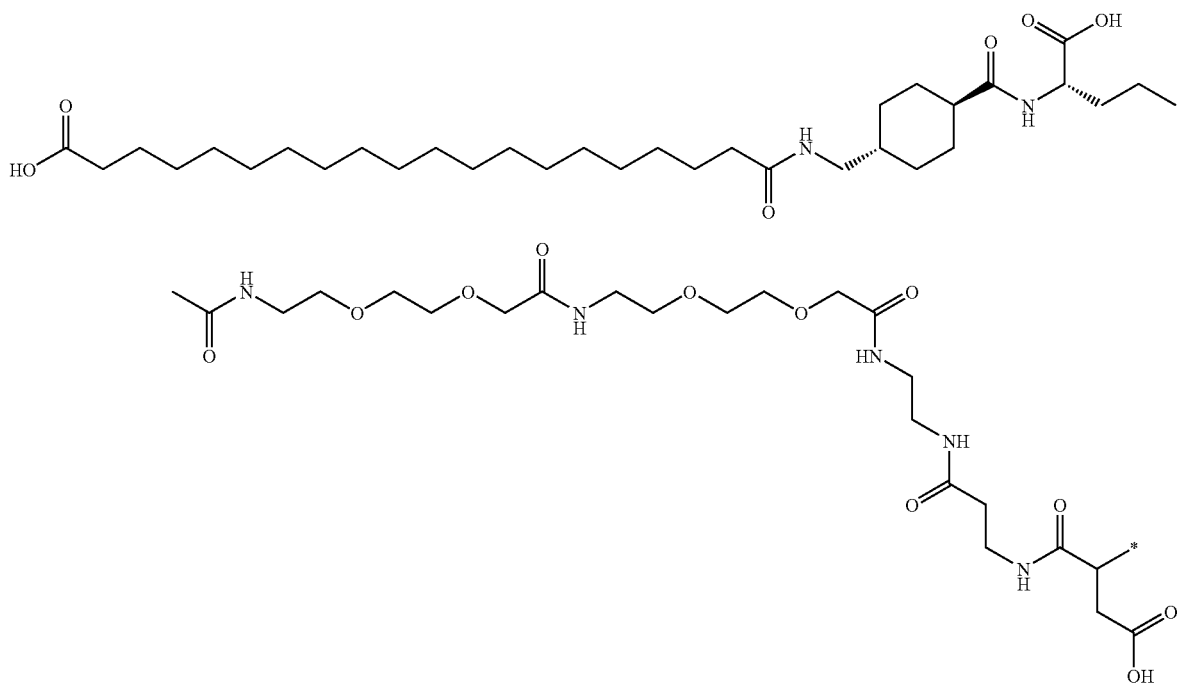

(12):

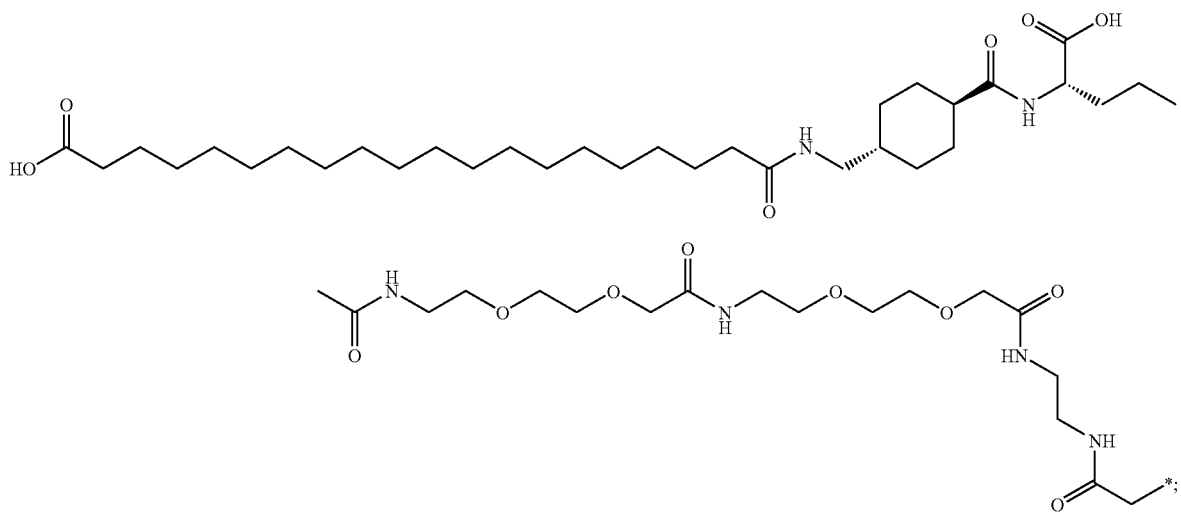

or a pharmaceutically acceptable salt of any one of the corresponding derivatives.

38. The derivative according to any one of the preceding embodiments to the extent possible, wherein the attachment of the albumin binder takes place via the thiol group of a cysteine residue.
39. The derivative according to any one of the preceding embodiments to the extent possible, wherein the albumin binder is attached to a cysteine residue at one or more positions selected from positions −1, 6, 71 and 122 of the FGF21 compound, wherein the position numbering is by reference to SEQ ID NO:1.
40. A compound selected from the derivatives of Examples 4, 5 and 6, according to any one of the preceding embodiments to the extent possible, preferably the following:

S-122-[1-(2-{2-[2-(2-{2-[2-(2-{2-[(S)-4-carboxy-4-(17-carboxy-heptadecanoylamino)-butyryl-amino]-ethoxy}-ethoxy)-acetylamino]-ethoxy}-ethoxy)-acetylamino]-ethylcarbamoyl}-ethyl)-2,5-dioxo-pyrrolidin-3-yl] [Cys122]-Met-FGF21 (Compound F);

S-71-[1-(2-{2-[2-(2-{2-[2-(2-{2-[(S)-4-carboxy-4-(19-carboxy-nonadecanoylamino)-butyryl-amino]-ethoxy}-ethoxy)-acetylamino]-ethoxy}-ethoxy)-acetylamino]-ethylcarbamoyl}-ethyl)-2,5-dioxo-pyrrolidin-3-yl] [Cys71]Met-FGF21 (Compound H); and S-71-({2-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-ethylcarbamoyl}-methyl) [Cys71]Met-FGF21 (Compound O);

or a pharmaceutically acceptable salt of any one of these compounds.

41. A derivative of an FGF21 compound having an albumin binder of the formula A-B-C- covalently attached to an amino group of the FGF21 compound, according to any one of the preceding embodiments to the extent possible, wherein A- is an element of formula I, II or III:

(formula I)

(formula II)

(formula III)

wherein n is 10, 11, 12, 13, 14, 15, 16, 17, 18 or 19, and * is the point of attachment to -B-;
-B- is -B1-, -B2- or combinations thereof, wherein
-B1- is an element of formula IV, V, VI or VII:

(formula IV or Trx)

(formula V or Inp)

(formula VI)

(formula VII)

wherein * is the point of attachment to -B2- or -C-, and # is the point of attachment to A- or -B2-; and
-B2- is an element of formula IIX or IX or a combination of up to four elements of formula IIX and/or formula IX:

(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2- or (formula IX)

wherein d is 1 or 2, e is 0, 1 or 2, * is the point of attachment to -C- or -B1-, and # is the point of attachment to A- or -B1-; and
-C- is an element of formula X or XI:

(formula X)

wherein p is 0, 1, 2, 3, 4, 5 or 6, q is 0, 1, 2, 3, 4, 5 or 6, * is the point of attachment to the FGF21 compound, and # is the point of attachment to -B-; or (formula XI)

wherein k is 0, 1, 2, 3, 4, 5, 11 or 23, m is 0, 1, 2, 3, 4, 5 or 6, * is the point of attachment to the FGF21 compound; and # is the point of attachment to -B-;
or a pharmaceutically acceptable salt thereof.

42. A derivative of an FGF21 compound having an albumin binder of the formula A-B-C- covalently attached to an amino group of the FGF21 compound, according to any one of the preceding embodiments to the extent possible, wherein
A- is an element of formula I, II III:

(formula I)

-continued

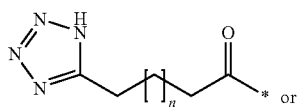
(formula II)

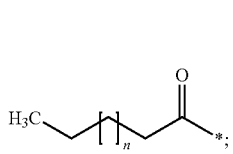
(formula III)

wherein n is 10, 11, 12, 13, 14, 15, 16, 17, 18 or 19, and * is the point of attachment to -B-;

-B- is -B1-, -B2- or combinations thereof, wherein

-B1- is an element of formula IV, V, VI or VII:

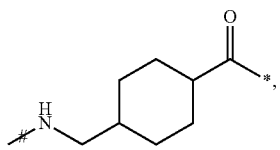
(formula IV or Trx)

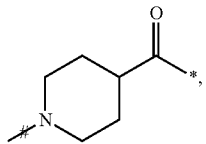
(formula V or Inp)

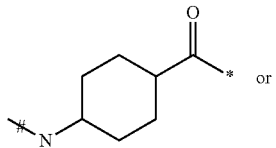
(formula VI)

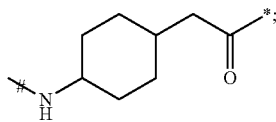
(formula VII)

wherein * is the point of attachment to -B2- or -C-, and # is the point of attachment to A- or -B2-; and -B2- is an element of formula IIX or IX or a combination of up to four elements of formula IIX and/or formula IX:

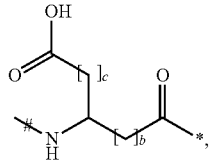
(formula IIX)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2- or

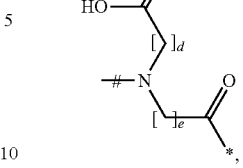
(formula IX)

wherein d is 1 or 2, e is 0, 1 or 2, * is the point of attachment to -C- or -B1-, and # is the point of attachment to A- or -B1-, or

—NH—SO$_2$—(CH$_2$)$_u$—CO—*   (formula XXVIII)

wherein u is 2, 3 or 4, * is the point of attachment to -C- or -B1-, and # is the point of attachment to A- or -B1- and;

-C- is an element of formula X or XI:

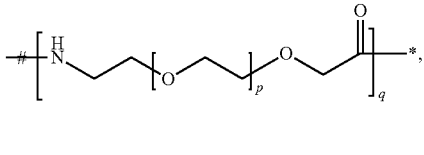
(formula X)

wherein p is 0, 1, 2, 3, 4, 5 or 6, q is 0, 1, 2, 3, 4, 5 or 6, * is the point of attachment to the FGF21 compound, and # is the point of attachment to -B-; or

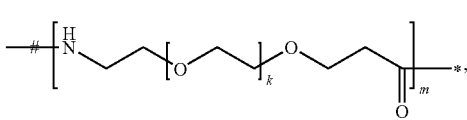
(formula XI)

wherein k is 0, 1, 2, 3, 4, 5, 11 or 23, m is 0, 1, 2, 3, 4, 5 or 6, * is the point of attachment to the FGF21 compound; and # is the point of attachment to -B-;

or a pharmaceutically acceptable salt thereof.

43. The derivative, according to any one of the preceding embodiments to the extent possible, preferably according to any one of embodiments 1-3 and 29, in which A- is an element of formula I:

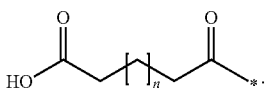
(formula I)

44. The derivative, according to any one of the preceding embodiments to the extent possible, in which n is 14, 16 or 18.

45. The derivative, according to any one of the preceding embodiments to the extent possible, in which -B- comprises -B1-, preferably an element of formula IV or V:

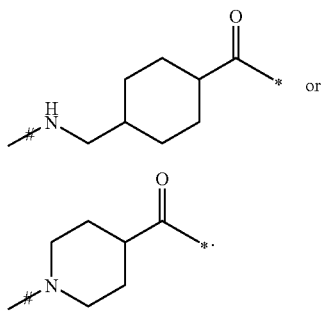
(formula IV)

(formula V)

46. The derivative, according to any one of the preceding embodiments to the extent possible, in which -B- comprises -B2-, preferably one or two elements of formula IIX:

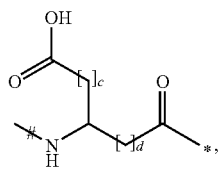
(formula IIX)

in which more preferably c is 0 and b is 2, or c is 0 and b is 1.

47. The derivative, according to any one of the preceding embodiments to the extent possible, in which -B- comprises -B2-, preferably one or two elements of formula IX:

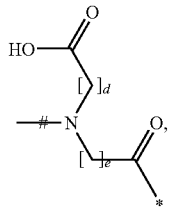
(formula IX)

In which more preferably d is 1 and e is 2 or, d is 2 and e is 1.

48. The derivative according to any one of the preceding embodiments to the extent possible, in which -B- comprises -B2-, preferably one or two elements of formula XXVIII:

—NH—SO$_2$—(CH$_2$)$_u$—CO—*      (formula XXVIII)

in which more preferably u is 3.

49. The derivative, according to any one of the preceding embodiments to the extent possible, in which -C- is an element of formula X:

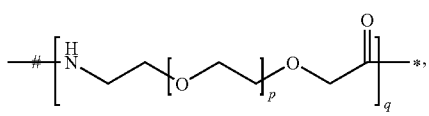
(formula X)

in which preferably q is 0, 1, 2, 3 or 4, more preferably q is 1 or 2.

50. The derivative, according to any one of the preceding embodiments to the extent possible, in which -C- is an element of formula X:

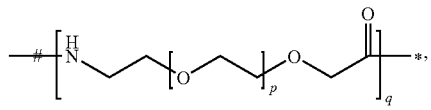
(formula X)

in which preferably p is 1 or 2, more preferably p is 1.

51. The derivative, according to any one of the preceding embodiments to the extent possible, in which p is 1 and q is 1 or 2, preferably p is 1 and q is 2.

52. The derivative, according to any one of the preceding embodiments to the extent possible, in which -C- is an element of formula XI:

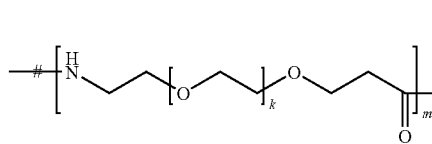
(formula XI)

in which preferably m is 0, 1 or 2, more preferably m is 1 or 2.

53. The derivative, according to any one of the preceding embodiments to the extent possible, in which in which -C- is an element of formula XI:

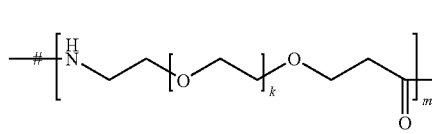
(formula XI)

in which preferably k is 1, 2, 3, 4, 5 or 11, more preferably k is 5.

54. The derivative, according to any one of the preceding embodiments to the extent possible, in which m is 1 and k is 4, 5 or 11, preferably m is 1 and k is 5.

55. The derivative, according to any one of the preceding embodiments to the extent possible, having one or two albumin binders of the formula A-B-C-.

56. The derivative, according to any one of the preceding embodiments to the extent possible, which has two albumin binders.

57. The derivative, according to any one of the preceding embodiments to the extent possible, wherein A- is an element of formula I, II or III:

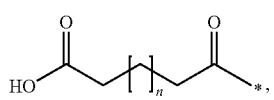
(formula I)

-continued

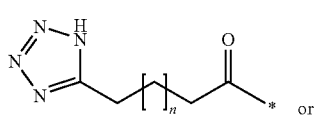 (formula II)

or

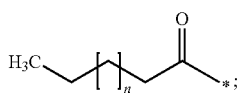 (formula III)

wherein n is 10, 11, 12 or 13.

58. The derivative, according to any one of the preceding embodiments to the extent possible, wherein A- is an element of formula I, II or III:

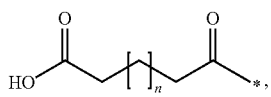 (formula I)

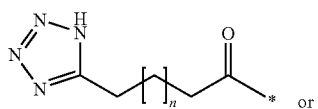 (formula II)

or

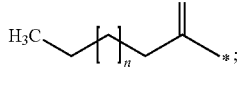 (formula III)

wherein n is 8, 9, 10, 11, 12 or 13.

59. The derivative, according to any one of the preceding embodiments to the extent possible, which has one albumin binder.

60. The derivative, according to any one of the preceding embodiments to the extent possible, wherein A- is an element of formula I, II or III:

(13):

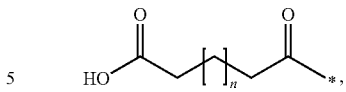 (formula I)

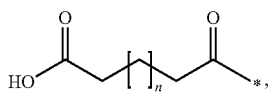 (formula II)

or (formula III)

wherein n is 14, 15, 16, 17, 18 or 19.

61. The derivative, according to any one of the preceding embodiments to the extent possible, wherein A- is an element of formula I, II or III:

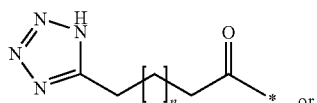 (formula I)

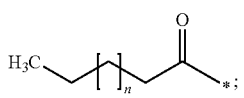 (formula II)

or (formula III)

wherein n is 12, 13, 14, 15, 16, 17, 18 or 19.

62. A derivative of an FGF21 compound having an albumin binder of the formula A-B-C- covalently attached, according to any one of the preceding embodiments to the extent possible, wherein A-B-C- is selected from the following formulas (13)-(19):

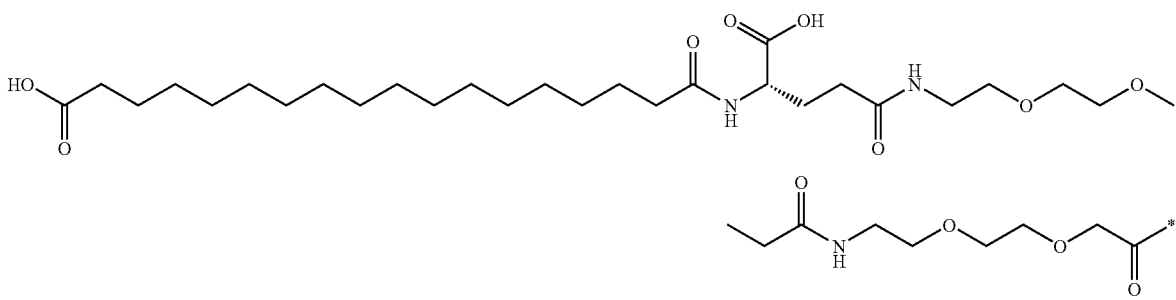

(14):
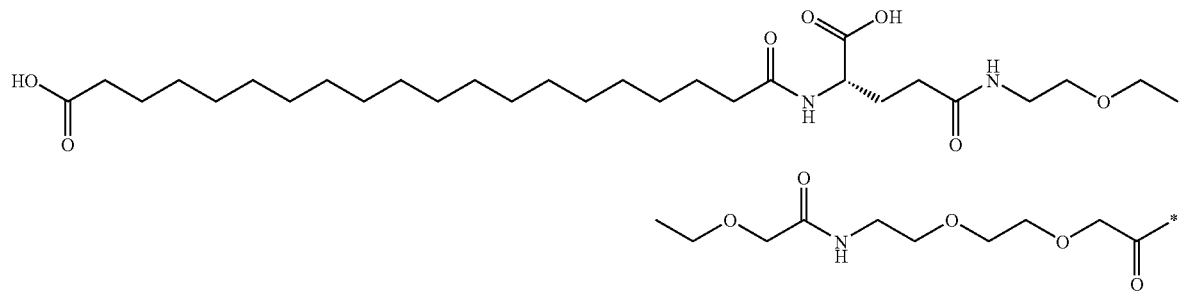
(15):
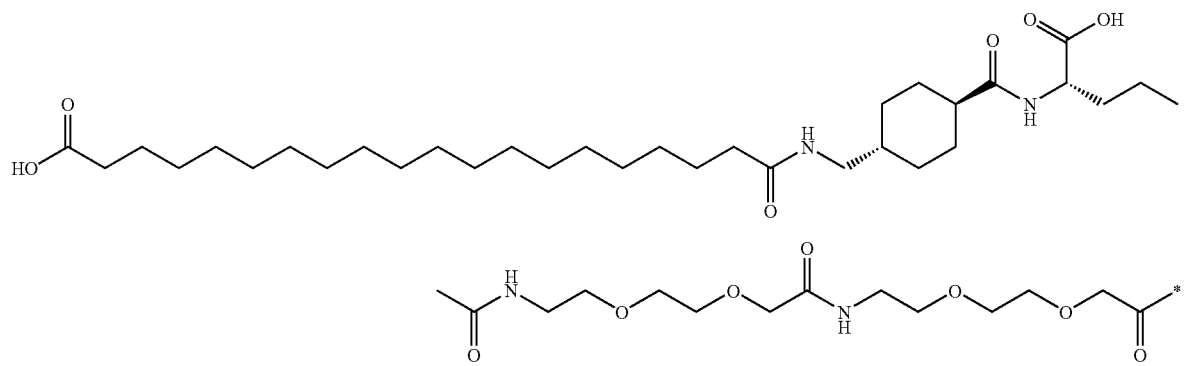
(16):
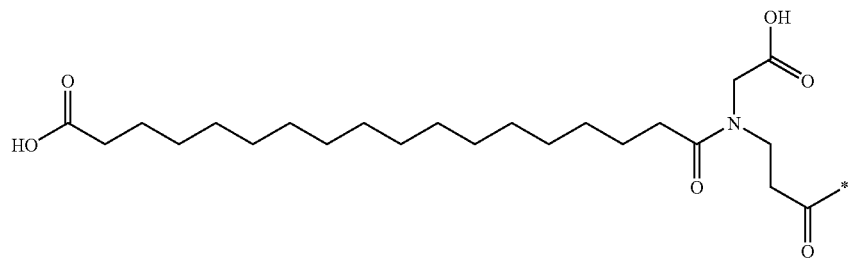
(17):
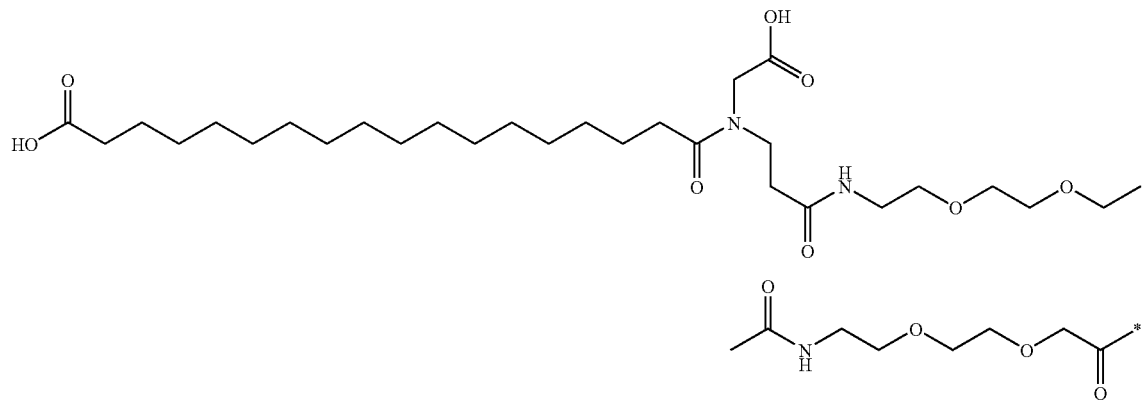
(18):
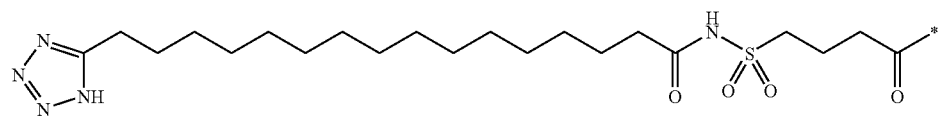

(19):

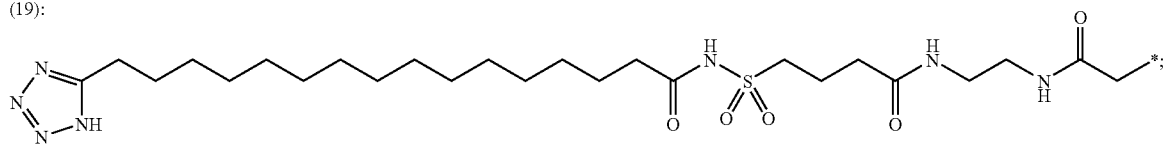

or a pharmaceutically acceptable salt of any of the corresponding derivatives.

63. A derivative of an FGF21 compound having an albumin binder of the formula A-B-C- covalently attached, according to any one of the preceding embodiments to the extent possible, wherein A-B-C- is selected from the following formulas (13)-(15):

(13):

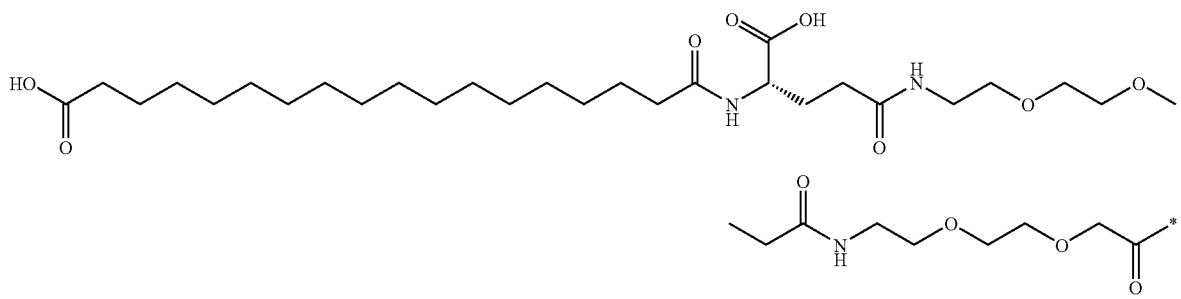

(14):

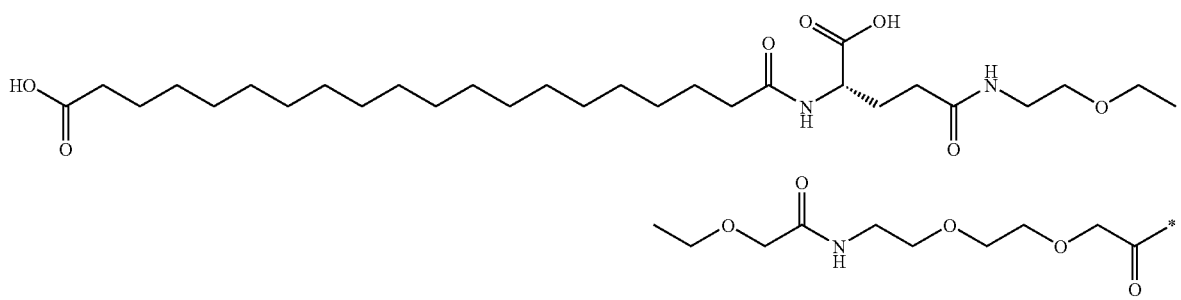

(15):

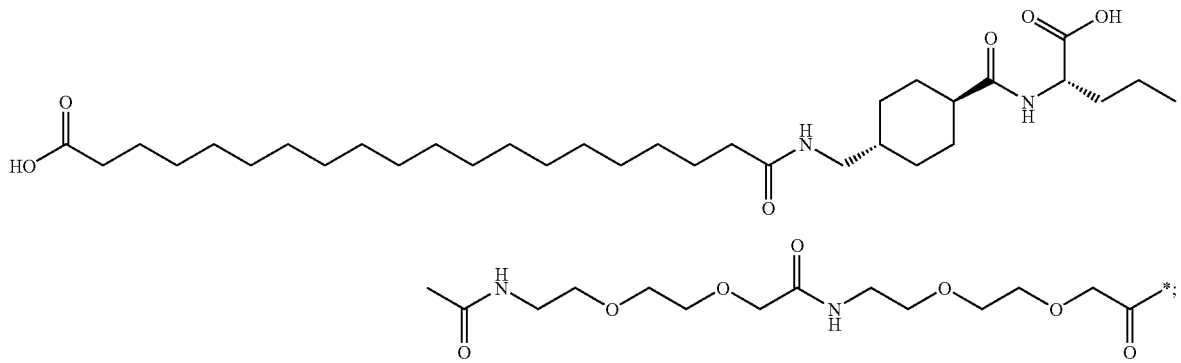

or a pharmaceutically acceptable salt of any of the corresponding derivatives.

64. The derivative, according to any one of the preceding embodiments to the extent possible, wherein the attachment of the albumin binder takes place via the amino group of the N-terminal amino acid residue.

65. The derivative, according to any one of the preceding embodiments to the extent possible, wherein the attachment of the albumin binder takes place via the epsilon amino group of a lysine residue.

66. The derivative, according to any one of the preceding embodiments to the extent possible, in which one albumin binder is attached to the N-terminal amino acid residue and another to an internal lysine residue.

67. The derivative, according to any one of the preceding embodiments to the extent possible, wherein the albumin binder(s) is/are attached to a lysine residue at one or more positions selected from positions 56, 59, 69, 122 and 152 of the FGF21 compound, wherein the position numbering is by reference to SEQ ID NO:1.

68. The derivative, according to any one of the preceding embodiments to the extent possible, preferably of Example 7, preferably the following: N-alpha1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Arg56, Arg59, Arg69, Arg122] Met-FGF21 (Compound V);
or a pharmaceutically acceptable salt thereof.

69. The derivative, according to any one of the preceding embodiments to the extent possible, wherein the FGF21 compound has an identity of at least 80%, to SEQ ID NO:1, preferably at least 85%, more preferably at least 90%, even more preferably at least 95%.

70. The derivative, according to any one of the preceding embodiments to the extent possible, wherein the FGF21 compound has a maximum of 36 amino acid modifications as compared to SEQ ID NO:1, preferably a maximum of 30, 25, 20, 15, 10 or 5 amino acid changes, or a maximum of 30, 25, 20, 15, 14, 13, 12, 11,10, 9, 8, 7, 6, 5, 4, 3, 2 or 1 amino acid change(s); more preferably a maximum of 15, 14, 13, 12, 11 or 10 amino acid modifications; even more preferably a maximum of 9, 8, 7, 6 or 5 amino acid modifications; or most preferably a maximum of 4, 3, 2 or 1 amino acid modification(s).

71. The derivative, according to any one of the preceding embodiments to the extent possible, wherein the FGF21 compound has an N-terminal extension of up to 25 amino acid residues, preferably up to 20 amino acid residues, more preferably up to 15 amino acid residues, even more preferably up to 10 amino acid residues, or most preferably up to 6 amino acid residues.

72. The derivative, according to any one of the preceding embodiments to the extent possible, in which at least 50%, preferably at least 60%, more preferably at least 70%, even more preferably at least 80%, or most preferably at least 90% of the N-terminally extending amino acid residues are glycine or serine.

73. The derivative, according to any one of the preceding embodiments to the extent possible, wherein the FGF21 compound comprises the amino acid sequence of SEQ ID NO:1.

74. The derivative, according to any one of the preceding embodiments to the extent possible, wherein the FGF21 compound comprises
(a) at least one of the following modifications as compared to SEQ ID NO:1: −1M, −1G, −1C, −1S, S6C, S6K, A26E, Q27E, Q28R, A31 E, K56R, K59R, K69R, S71 C, D102T, L118C, K122C, K122R, A134C, I152K, L166F, S167G, M168L, V169aT, P171L, S172E, Q173A, G174V, Y179F, A180E and/or S181K,R (preferably at least one of the following: −1M, −1G, −1C, −1S, S6C, S6K, A26E, Q27E, Q28R, A31E, K56R, K59R, K69R, S71C, D102T, L118C, K122C, K122R, A134C, I152K and/or M168L); and/or
(b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S.

75. The derivative, according to any one of the preceding embodiments to the extent possible, wherein the FGF21 compound comprises (a) the following modifications, as compared to SEQ ID NO:1:
(i) K122C, (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q173A, G174V, A31E), Q27E, M168L, (Y179F, A180E, S181R), (V169aT, P171L, S172E, Q173A, G174V, Y179F, A180E, S181K) and/or (L166F, S167G, M168L, V169aT, P171L, S172E, Q173A, G174V, Y179F, A180E, S181K) (preferably K122C, (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31 E), Q27E and/or M168L),
(ii) −1G and (−1G, M168L), or
(iii) S6C, (L118C-A134C, K56R, K59R, K69R, K122R) and (S6K, K56R, K59R, K69R, K122R),
wherein the FGF21 compound of (i) and (iii) may further, optionally, include an N-terminal M; and/or
(b) an N-terminal extension as compared to SEQ ID NO:1 selected from the following:
(iv) MG-, MC-, MS-, MSGSGSGSGSG-, MGGGGG-, MSHSGSGSGSGSGSGSGSGSG-, MSGGGGG-, MSGGGS-, MSGGSSG- and MSGSGSG-,
wherein the N-terminal M in each of the FGF21 compounds of (iv) may, optionally, be deleted.

76. The derivative, according to any one of the preceding embodiments to the extent possible, wherein the FGF21 compound comprises the following substitutions as compared to SEQ ID NO:1: (a) K122C; (b) (K59R, K69R, K122R); (c) (K56R, K69R, K122R); (d) (K56R, K59R, K69R); (e) S71C; (f) S6C; (g) (K56R, K59R, K69R, K122R); (h) (K56R, K59R, K69R, K122R, I152K); (i) (L118C-A134C, K56R, K59R, K69R, K122R); (j) (S6K, K56R, K59R, K69R, K122R); or (k) M168L.

77. The derivative, according to any one of the preceding embodiments to the extent possible, wherein the FGF21 compound comprises the following amendments as compared to SEQ ID NO: 1: Y179F, A180E and S181K or S181R (i); preferably additionally V169aT, P171L, S172E, Q173A and G174V (ii); more preferably additionally L166F, S167G and M168L (iii); most preferably (i), (ii) and (iii), wherein each embodiment independently and optionally includes an N-terminal M (e.g., −1M).

78. The derivative, according to any one of the preceding embodiments to the extent possible, wherein the FGF21 compound comprises the following amendments as compared to FGF21 (SEQ ID NO:1): (i) Met-Gly- at the N-terminus, (ii) M168L, (iii) embodiment (i) and (ii), (iv) Met-Cys- at the N-terminus, (v) Gly- at the N-terminus, (vi) embodiment (v) and (ii), (vii) Met-Ser- at the N-terminus, or (iix) Ser- at the N-terminus; preferably the FGF21 compound is selected from the following: (I) Met-Gly-FGF21, (m) Met-Gly-FGF21-M168L, (n) Met-Cys-FGF21, (o) Gly-FGF21-M168L, (p) Gly-FGF21, (q) Met-Ser-FGF21, or (r) Ser-FGF21; wherein FGF21 refers to the polypeptide of SEQ ID NO:1.

79. The derivative, according to any one of the preceding embodiments to the extent possible, wherein the FGF21 compound comprises the following N-terminal extensions as compared to SEQ ID NO:1: (q) MS-FGF21, (s) MSGSGSGSGSG-, (t) MGGGGG-, (u) MSHSGSGSGSGSGSGSGSGSG-, (v) MSGGGGG-, (x) MSGGGS-, (y) MSGGSSG- and (z) MSGSGSG-; as well as any one of the embodiments (q), (s), (t), (u), (v), (x), (y) and (z) without the N-terminal Met.

80. The derivative, according to any one of the preceding embodiments to the extent possible, wherein the FGF21 compound is selected from the following variants of the polypeptide of SEQ ID NO:1: (a) K122C, (e) S71C, (f) S6C, (n) Met-Cys-FGF21, any one of the compounds (a), (e) and (f) with an N-terminal Met, and compound (n) without the N-terminal Met.

81. The derivative, according to any one of the preceding embodiments to the extent possible, wherein the FGF21 compound is selected from the following variants of the polypeptide of SEQ ID NO:1: (b) (K59R, K69R, K122R); (c) (K56R, K69R, K122R); (d) (K56R, K59R, K69R); (g) (K56R, K59R, K69R, K122R); (h) (K56R, K59R, K69R, K122R, I152K); (i) (L118C-A134C, K56R, K59R, K69R, K122R); (j) (S6K, K56R, K59R, K69R, K122R); (k) (179F, 180E, 181R); (l) (169aT, 171L, 172E, 173A, 174V, 179F, 180E, 181K); and (m) (166F, 167G, 168L, 169aT, 171L, 172E, 173A, 174V, 179F, 180E, 181K); as well as any one of the compounds (b), (c), (d), (g), (h), (i) and (j) with an N-terminal Met (preferably (b)-(j) +/− N-terminal Met).

82. The derivative, according to any one of the preceding embodiments to the extent possible, which has a proline at position 146, wherein the position number refers to SEQ ID NO:1.

83. The derivative, according to any one of the preceding embodiments to the extent possible, which has a T½ when dosed s.c. in mice of at least 1.5 hours, preferably at least 2 hours, more preferably at least 4 hours, even more preferably at least 5 hours, or most preferably at least 6 hours.

84. The derivative, according to any one of the preceding embodiments to the extent possible, which has a T½ when dosed s.c. in mice of at least 10 hours, preferably at least 15 hours, more preferably at least 24 hours, or most preferably at least 48 hours.

85. The derivative, according to any one of the preceding embodiments to the extent possible, in which (i) the mice are db/db mice, preferably mice that lack the leptin receptor, and/or (ii) the dosage of the derivative is 0.5 mg/kg.

86. The derivative, according to any one of the preceding embodiments to the extent possible, or an FGF analogue according to any of the embodiments below to the extent possible, which has a potency of at least 1%, preferably of at least 5%, more preferably of at least 10%, even more preferably of at least 20%, or most preferably of at least 30%, relative to the potency of Met-FGF21, wherein the potency is determined by measuring glucose uptake in 3T3-L1 adipocytes.

87. The derivative, according to any one of the preceding embodiments to the extent possible, or an FGF analogue according to any of the embodiments below to the extent possible, which has a potency of at least 40%, preferably of at least 50%, more preferably of at least 60%, even more preferably of at least 70%, relative to the potency of Met-FGF21.

88. The derivative, according to any one of the preceding embodiments to the extent possible, or an FGF analogue according to any of the embodiments below to the extent possible, which has a potency of at least 80%, preferably at least 90%, more preferably at least 100%, even more preferably at least 110%, or most preferably at least 120%, relative to the potency of Met-FGF21.

89. The derivative, according to any one of the preceding embodiments to the extent possible, or an FGF analogue according to any of the embodiments below to the extent possible, in which the potency is calculated as the $EC_{50}$ of the derivative relative to the $EC_{50}$ of Met-FGF21.

90. The derivative, according to any one of the preceding embodiments to the extent possible, or an FGF analogue according to any of the embodiments below to the extent possible, in which the 3T3-L1 adipocytes derive from mouse 3T3-L1 fibroblasts, preferably ATCC CL-173.

91. The derivative, according to any one of the preceding embodiments to the extent possible, or an FGF analogue according to any of the embodiments below to the extent possible, in which the glucose uptake in 3T3-L1 adipocytes is measured as outlined in Example 8.

92. The derivative, according to any one of the preceding embodiments to the extent possible, or an FGF analogue according to any of the embodiments below to the extent possible, which has a potency of at least 1% relative to the potency of Met-FGF21, wherein the potency is determined as described in any one of embodiments 64-69.

93. The derivative, according to any one of the preceding embodiments to the extent possible, or an FGF analogue according to any of the embodiments below to the extent possible, wherein the potency relative to Met-FGF21 is at least 1%, preferably at least 5%, more preferably at least 10%, even more preferably at least 20%, or most preferably at least 30%.

94. The derivative, according to any one of the preceding embodiments to the extent possible, or an FGF analogue according to any of the embodiments below to the extent possible, wherein the potency relative to Met-FGF21 is at least 40%, preferably at least 50%, more preferably at least 60%, or most preferably at least 70%.

95. The derivative, according to any one of the preceding embodiments to the extent possible, or an FGF analogue according to any of the embodiments below to the extent possible, wherein the potency relative to Met-FGF21 is at least 80%, preferably at least 90%, more preferably at least 100%, even more preferably at least 110%, or most preferably at least 120%.

96. The derivative, according to any one of the preceding embodiments to the extent possible, or an FGF analogue according to any of the embodiments below to the extent possible, which is capable of lowering blood glucose in vivo in db/db mice relative to a vehicle control.

97. The derivative, according to any one of the preceding embodiments to the extent possible, wherein blood glucose is lowered 24 hours, preferably 48 hours, after a last dose of the derivative has been administered.

98. The derivative, according to any one of the preceding embodiments to the extent possible, or an FGF analogue according to any of the embodiments below to the extent possible, wherein the blood glucose is lowered by at least 10%, preferably by at least 15%, more preferably by at least 20%, even more preferably by at least 25%, or most preferably by at least 30%, based on the mean blood glucose measurements in mM and relative to the corresponding vehicle control.

99. The derivative, according to any one of the preceding embodiments to the extent possible, or an FGF analogue according to any of the embodiments below to the extent possible, wherein the blood glucose is lowered by at least 35%, preferably by at least 40%, more preferably by at least 45%, or most preferably by at least 50%.

100. The derivative, according to any one of the preceding embodiments to the extent possible, wherein (i) the db/db mice are male and 9-11 weeks old, (ii) the derivative is administered s.c., (iii) the derivative dosage is in the range of 0.2-1.0 mg/kg, preferably 0.2, 0.4, 0.6, 0.8 or 1.0 mg/kg, (iv) the derivative is dissolved in PBS, (v) the derivative is dosed once daily, preferably on day 1, day 2 and day 3, (vi) the vehicle control is treated with PBS, preferably 250 ul/50 g mouse, and/or (vii) blood glucose is measured using the glucose oxidase method, preferably using a glucose analyzer such as Biosen 5040.

101. The derivative, according to any one of the preceding embodiments to the extent possible, wherein the vehicle control is replaced by Met-FGF21.
102. The derivative, according to any one of the preceding embodiments to the extent possible, or an FGF analogue according to any of the embodiments below to the extent possible, which is more stable than Met-FGF21 after oxidation by incubation in the presence of 300 mM $H_2O_2$ for 1 hour at 25° C.
103. The derivative, according to any one of the preceding embodiments to the extent possible, or an FGF analogue according to any of the embodiments below to the extent possible, in which the stability refers to potency, determined according to any one of embodiments 70-75.
104. The derivative, according to any one of the preceding embodiments to the extent possible, or an FGF analogue according to any of the embodiments below to the extent possible, which after incubation with $H_2O_2$ has a potency of at least 15%, preferably at least 20%, more preferably at least 30%, even more preferably at least 40%, or most preferably at least 50%, wherein the potency is relative to Met-FGF21 treated in the same way, however without $H_2O_2$.
105. The derivative, according to any one of the preceding embodiments to the extent possible, in which (i) the derivative and Met-FGF21 are both dissolved in PBS, pH 7.2, and/or (ii) the concentration of the derivative and Met-FGF21 is 1 mg/mL.
106. The derivative, according to any one of the preceding embodiments to the extent possible, which is any one of the specific derivatives mentioned in the above examples 4-7 and 12-55.
107. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [71C, 121Q, 166F, 167G, 168L, 169aT, 171L, 172E, 173A, 174V, 179F, 180E, des181K] Ala-FGF21.
108. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [28R, 56R, 59R, 69R, S71C, 102T, 121Q, 122R, 166F, 167G, 168L, 170T] Ala-FGF21.
109. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Q28R, K56R, K59R, K69R, D102T, N121Q, K122R, L166F, S167G, M168L, G170T]Ala-FGF21.
110. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [K56R, K59R, K69R, N121Q, K122R, L166F, S167G, M168L, 169aT, P171L, S172E, Q173A, G174V, Y179F, A180E, des S181] Ala-FGF21.
111. The derivative, according to any one of the preceding embodiments to the extent possible, which is N-alpha-1-[4-(16-1H-tetrazol-5-yl-hexadecanoylsulfamoyl)-butyryl] [K56R, K59R, K69R, N121Q, K122R, L166F, S167G, M168L, 169aT, P171L, S172E, Q173A, G174V, Y179F, A180E, des S181] Ala-FGF21.
112. The derivative, according to any one of the preceding embodiments to the extent possible, which is N-alpha-1-[4-(16-1H-tetrazol-5-yl-hexadecanoylsulfamoyl)-butyryl] [Q28R, K56R, K59R, K69R, D102T, N121Q, K122R, L166F, S167G, M168L, G170T]Ala-FGF21.
113. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) (Q28R, K56R, K59R, K69R, S71C, D102T, N121Q, K122R, L166F, S167G, M168L, G170T) Ala-FGF21.
114. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R) Gly-FGF21.
115. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R) Ala-FGF21.
116. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R) Ser-FGF21.
117. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R) FGF21.
118. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R, L166F, S167G, M168L, G170T) Gly-FGF21.
119. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R, L166F, S167G, M168L, G170T) Ala-FGF21.
120. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R, L166F, S167G, M168L, G170T) Ser-FGF21.

121. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R, L166F, S167G, M168L, G170T) FGF21.

122. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethyl-carbamoyl}-methyl) (S71C, 121Q, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21.

123. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethyl-carbamoyl}-methyl) (S71C, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21.

124. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21.

125. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetyl] (K56R, K59R, K69R, K122R, P143V, A145E, L146E, 148aD, P149L, P150R, I152H, 153aE, 153bS, 153aE, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21.

126. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethyl-carbamoyl}-methyl) (S71C, 121Q, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21.

127. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethyl-carbamoyl}-methyl) (S71C, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21.

128. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21.

129. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21.

130. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethyl-carbamoyl}-methyl) (S71C, 121Q, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21.

131. The derivative, according to any one of the preceding embodiments to the extent possible, which is S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethyl-carbamoyl}-methyl) (S71C, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21.

132. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, N121Q, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21.

133. The derivative, according to any one of the preceding embodiments to the extent possible, which is N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] (K56R, K59R, K69R, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21.

134. The derivative, according to any one of the preceding embodiments to the extent possible, in which the FGF compound is an FGF analogue, which is any one of the specific analogues mentioned in the above examples 2 (preferably examples 2a-2af), 56 (preferably examples 56a-56as) and 57 (preferably examples 57a-57v).

135. The derivative, according to any one of the preceding embodiments to the extent possible, in which the FGF compound is a FGF compound present in any one of the examples 4-7 and 12-55 herein.

136. The derivative, according to any one of the preceding embodiments to the extent possible, in which the FGF compound is (Q28R, K56R, K59R, K69R, D102T, N121Q, K122R, L166F, S167G, M168L, G170T) Ala-FGF21.

137. The derivative, according to any one of the preceding embodiments to the extent possible, in which the FGF compound is (S71C, N121Q, L166F, S167G, M168L, 169aT, P171 L, S172E, Q173A, G174V, Y179F, A180E, des S181) Ala-FGF21.

138. The derivative, according to any one of the preceding embodiments to the extent possible, in which the FGF compound is (K56R, K59R, K69R, N121Q, K122R, L166F, S167G, M168L, 169aT, P171L, S172E, Q173A, G174V, Y179F, A180E, des S181) Ala-FGF21.

139. The derivative, according to any one of the preceding embodiments to the extent possible, in which the FGF compound is (Q28R, K56R, K59R, K69R, S71C, D102T, N121Q, K122R, L166F, S167G, M168L, G170T) Ala-FGF21.

140. The derivative, according to any one of the preceding embodiments to the extent possible, wherein the FGF21 compound is any one of the FGF21 analogues mentioned in any one of the following embodiments.

141. An FGF21 analogue comprising
(a) at least one of the following modifications as compared to SEQ ID NO:1: −1G, −1C, −1S, -1A, S6C, S6K, Q27E, Q28R, A31E, K56R, K59R, K69R, S71C, D102E, D102T, N121Q, K122R, I152K, L166F, S167G, M168L, V169aT, G170T, P171L, S172E, Q173A, G174V, Y179F, A180E and/or S181K,R (preferably −1G, −1C, −1S, S6C, S6K, A26E, Q27E, Q28R, A31E, K56R, K59R, K69R, S71C, D102T, K122R, I152K and/or M168L); and/or (b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S.

142. An FGF21 analogue comprising (a) at least one of the following modifications as compared to SEQ ID NO:1: −1G, −1C, −1S, S6C, S6K, A26E, Q27E, Q28R, A31E, K56R, K59R, K69R, S71C, D102T, K122R, I152R, L166F, S167G, M168L, V169aT, P171L, S172E, Q173A, G174V, Y179F, A180E and/or S181K,R (preferably −1G, −1C, −1S, S6C, S6K, A26E, Q27E, Q28R, A31E, K56R, K59R, K69R, S71C, D102T, K122R, I152K and/or M168L); and/or
(b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S.

143. An FGF21 analogue comprising (a) at least one of the following modifications as compared to SEQ ID NO:1: −1A, −1C, −1S, −1G, S6K, S6C, Q15F, V16K, D24K, A26E, Q27E, Q28R, A31E, K56R, K59R, K69R, S71C, D102E, D102N, D102T, des121D, D121D, D121Q, K122R, P143V, A145E, 145aP, 145bM, L146V, L146E, 148aD, P149L, P149E, P150R, G151E, I152E, I152K, I152H, 153aE, 153b5, 153cD, 153dM, 1154F, 1154R, P155G, Q156H, Q156S, P157L, P158L, P158E, D159E, D159S, V160D, V160T, G161M, G161D, S162F, S163M, D164S, L166F, S167E, S167G, M168T, M168A, M168I, M168L, M168S, V169D, 169aT, G170T, G1705, P171M, P171L, S172D, S172E, Q173P, Q173A, G174F, G174A, G174V, R175G, 5176L, P177V, S178T, Y179G, Y179F, A180E, S181 K, S181R, 182G, and/or (b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S or at least one of the following modifications −15E, −14E, −13E, −12A, −10A, −11A, −11E, −10S, −9G, −8G, −8A, −7A, −6A, −6G, −5G, −4S, −3A, −3G, −2A, −2G, −2S.

144. An FGF21 analogue comprising (a) at least one of the following modifications as compared to SEQ ID NO:1: −1A, −1C, −1S, −1G, S6K, S6C, Q15F, V16K, D24K, A26E, Q27E, Q28R, A31 E, K56R, K59R, K69R, S71C, D102E, D102N, D102T, des121D, D121D, D121Q, K122R, P143V, A145E, L146E, 148aD, P149L, P150R, I152K, I152H, 153aE, 153bS, 153cD, 153dM, 1154F, P155S, Q156S, P158L, D159E, V160T, G161D, S163M, L166F, S167G, M168A, M168I, M168L, M168S, 169aT, G170T, P171L, S172E, Q173A, G174A, G174V, Y179F, A180E, S181 K, S181R, 182G, and/or (b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S or at least one of the following modifications −15E, −14E, −13E, −12A, −10A, −11A, −11E, −10S, −9G, −8G, −8A, −7A, −6A, −6G, −5G, −4S, −3A, −3G, −2A, −2G, −2S.

145. An FGF21 analogue comprising (a) at least one of the following modifications as compared to SEQ ID NO:1: −1A, −1C, −1S, −1G, S6K, S6C, Q15F, V16K, D24K, A26E, Q27E, Q28R, A31 E, K56R, K59R, K69R, S71C, D102E, D102N, D102T, des121D, D121D, D121Q, K122R, I152K, D159E, L166F, S167G, M168A, M168I, M168L, M168S, 169aT, G170T, P171L, S172E, Q173A, G174A, G174V, Y179F, A180E, S181K, S181R, 182G, and/or (b) an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are G or S or at least one of the following modifications −15E, −14E, −13E, −12A, −10A, −11A, −11E, −10S, −9G, −8G, −8A, −7A, −6A, −6G, −5G, −4S, −3A, −3G, −2A, −2G, −2S.

146. The FGF21 analogue, according to any one of the preceding embodiments relating to analogues, to the extent possible, wherein said FGF21 analogue contains not more than 210 amino acid residues, preferably not more than 209 amino acid residues, more preferred not more than 206 amino acid residues.

147. The FGF21 analogue, according to any one of the preceding embodiments relating to analogues, to the extent possible, wherein if the N-terminal extension is only a sigle amino acid, said amino acid is different from Met.

148. The FGF21 analogue, according to any one of the preceding embodiments relating to analogues, to the extent possible, which comprises
(a) the following modifications, as compared to SEQ ID NO:1:
(i) (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31E), Q27E, M168L, (Y179F, A180E, S181R), (V169aT, P171L, S172E, Q173A, G174V, Y179F, A180E, S181 K), (L166F, S167G, M168L, V169aT, P171L, S172E, Q173A, G174V, Y179F, A180E, S181K) (preferably (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31E), Q27E, or M168L),
(ii) −1G and (−1G, M168L), or
(iii) S6C, (L118C-A134C, K56R, K59R, K69R, K122R) and (S6K, K56R, K59R, K69R, K122R),
wherein the FGF21 analogue of (i) and (iii) may further, optionally, include an N-terminal M; and/or
(b) an N-terminal extension as compared to SEQ ID NO:1 selected from the following: (iv) MG-, MC-, MS-, MSGSGSGSGSG-, MGGGGG-, MSHSGSGSGSGSGSGSGSG-, MSGGGGG-, MSGSGGS-, MSGGSSG- and MSGSGSG-,
wherein the N-terminal M in each of the FGF21 analogues of (iv) may, optionally, be deleted.

149. The FGF21 analogue, according to any one of the preceding embodiments relating to analogues, to the extent possible, which comprises
(a) the following modifications, as compared to SEQ ID NO:1: (K59R, K69R, K122R), (K56R, K69R, K122R), (K56R, K59R, K69R), S71C, (K56R, K59R, K69R, K122R), (K56R, K59R, K69R, K122R, I152K), D102T, A26E, (Q28R, A31E), Q27E, M168L, (Y179F, A180E, S181R), (V169aT, P171L, S172E, Q173A, G174V, Y179F, A180E, S181K), or (L166F, S167G, M168L, V169aT, P171L, S172E, Q173A, G174V, Y179F, A180E, S181K) (preferably (K59R, K69R, K122R), (K56R, K69R, K122R), (K56R, K59R, K69R), S71C, (K56R, K59R, K69R, K122R), or (K56R, K59R, K69R, K122R, I152K), D102T, A26E, (Q28R, A31E), Q27E, or M168L),
wherein the FGF21 analogue may further, optionally, include an N-terminal M; and/or (b) an N-terminal extension as compared to SEQ ID NO:1 selected from the following:
(iv) MG-, MC-, MS-, MSGSGSGSGSG-, MGGGGG-, MSHSGSGSGSGSGSGSGSG-, MSGGGGG-, MSGSGGS-, MSGGSSG- and MSGSGSG-, wherein the N-terminal M in each of the FGF21 analogues of (iv) may, optionally, be deleted.

150. The FGF21 analogue, according to any one of the preceding embodiments relating to analogues, to the extent possible, which comprises (a) the following modifications, as compared to SEQ ID NO:1: −1G and (−1G, M168L); and/or (b) an N-terminal extension as compared to SEQ ID NO:1 selected from the following: (iv) MG-, MC-, MS-, MSGSGSGSGSG-, MGGGGG-, MSHSGSGSGSGSGSGSGSG-, MSGGGGG-, MSGSGGS-, MSGGSSG- and MSGSGSG-, wherein the N-terminal M in each of the FGF21 analogues of (iv) may, optionally, be deleted.

151. The FGF21 analogue, according to any one of the preceding embodiments relating to analogues, to the extent possible, which comprises (a) the following modifications, as compared to SEQ ID NO:1: S6C, (L118C-A134C, K56R, K59R, K69R, K122R) and (S6K, K56R, K59R, K69R, K122R), wherein the FGF21 analogue may further, optionally, include an N-terminal M; and/or (b) an N-terminal extension as compared to SEQ ID NO:1 selected from the following: (iv) MG-, MC-, MS-, MSGSGSGSGSG-, MGGGGG-, MSHSGSGSGSGSGSGSGSG-, MSGGGGG-, MSGSGGS-, MSGGSSG- and MSGSGSG-, wherein the N-terminal M in each of the FGF21 analogues of (iv) may, optionally, be deleted.

152. An FGF21 analogue, according to any one of the preceding embodiments relating to analogues, to the extent possible, comprising one or more of the following modifications, as compared to the polypeptide of SEQ ID NO:1: S6C, S6K, K56R, K59R, K69R, S71C, K122R, I152K, L166F, S167G, M168L, V169aT, P171L, S172E, Q173A, G174V, Y179F, A180E and/or S181K,R (preferably S6C, S6K, K56R, K59R, K69R, S71C, K122R, I152K and/or M168L).

153. An FGF21 analogue, according to any one of the preceding embodiments relating to analogues, to the extent possible, comprising one or more of the following modifications, as compared to the polypeptide of SEQ ID NO:1: S6C, S71C, M168L, (S6K, K56R, K59R, K69R, K122R), (K56R, K59R, K69R), (K56R, K69R, K122R), (K59R, K69R, K122R), (K56R, K59R, K69R, K122R), (K56R, K59R, K69R, K122R, I152K) and (K56R, K59R, K69R, K122R, L118C-A134C), (L166F, S167G, M168L, V169aT, P171L, S172E, Q173A, G174V, Y179F, A180E, S181K), (V169aT, P171L, S172E, Q173A, G174V, Y179F, A180E, S181K) and/or (Y179F, A180E, S181R); preferably (S6C, S71C, M168L, (S6K, K56R, K59R, K69R, K122R), (K56R, K59R, K69R), (K56R, K69R, K122R), (K59R, K69R, K122R), (K56R, K59R, K69R, K122R), (K56R, K59R, K69R, K122R, I152K) and/or (K56R, K59R, K69R, K122R, L118C-A134C).

154. An FGF21 analogue, according to any one of the preceding embodiments relating to analogues, to the extent possible, comprising Y179F, Al 80E and S181 K or S181R (i); preferably additionally comprising V169aT, P171L, S172E, Q173A and G174V (ii); more preferably additionally comprising L166F, S167G and M168L (iii); most preferably comprising (i), (ii) and (iii).

155. The FGF21 analogue, according to any one of the preceding embodiments relating to analogues, to the extent possible, preferably according to any one of embodiments 89-90 including 90a, further including a Met at position -1 of SEQ ID NO:1.

156. An FGF21 analogue, according to any one of the preceding embodiments relating to analogues, to the extent possible, selected from amongst the following: (I) Met-Gly-FGF21, (m) Met-Gly-FGF21-M168L, (n) Met- Cys-FGF21, (o) Gly-FGF21-M168L, (p) Gly-FGF21, (q) Met-Ser-FGF21, or (r) Ser-FGF21; wherein FGF21 designates the polypeptide of SEQ ID NO:1.

157. An FGF21 analogue, according to any one of the preceding embodiments relating to analogues, to the extent possible, which has an N-terminal extension as compared to SEQ ID NO:1 of up to 25 amino acid residues, preferably up to 20 amino acid residues, more preferably up to 15 amino acid residues, even more preferably up to 10 amino acid residues, or most preferably up to 6 amino acid residues, wherein at least 50%, preferably at least 60%, more preferably at least 70%, even more preferably at least 80%, or most preferably at least 90% of the N-terminally extending amino acid residues are glycine or serine.

158. An FGF21 analogue, according to any one of the preceding embodiments relating to analogues, to the extent possible, preferably the analogue of embodiment 93, which comprises the following N-terminal extensions as compared to SEQ ID NO:1: (q) MS-FGF21, (s) MSGSGSGSGSG-, (t) MGGGGG-, (u) MSHSGSGSGSGSGSGSGSGSG-, (v) MSGGGGG-, (x) MSGSGGS-, (y) MSGGSSG- and (z) MSGSGSG-; as well as any one of the embodiments (q), (s), (t), (u), (v), (x), (y) and (z) without the N-terminal Met.

159. An FGF21 analogue, according to any one of the preceding embodiments relating to analogues, to the extent possible, which is selected from amongst the following: (r) MSGSGSGSGSG-FGF21, (s) MGGGGG-FGF21, (t) MSHSGSGSGSGSGSGSGSGSG-FGF21, (u) MSGGGGG-FGF21, (v) MSGSGGS-FGF21, (x) MSGGSSG-FGF21 and (y) MSGSGSG-FGF21, as well as any one of embodiments (r), (s), (t), (u), (v), (x) and (y) without the N-terminal Met; wherein FGF21 refers to SEQ ID NO:1.

160. The FGF21 analogue, according to any one of the preceding embodiments relating to analogues, to the extent possible, which has a P (proline) at position 146, wherein the position number refers to SEQ ID NO:1.

161. The FGF21 analogue, according to any one of the preceding embodiments relating to analogues, to the extent possible, which has a potency of at least 1%, preferably at least 5%, more preferably at least 10%, or most preferably at least 20% relative to the potency of Met-FGF21, wherein the potency is determined by measuring glucose uptake in 3T3-L1 adipocytes.

162. The FGF21 analogue, according to any one of the preceding embodiments relating to analogues, to the extent possible, wherein the potency is at least 30%, preferably at least 40%, more preferably at least 50%, even more preferably at least 60%, or most preferably at least 70%, relative to the potency of Met-FGF21.

163. The FGF21 analogue, according to any one of the preceding embodiments relating to analogues, to the extent possible, wherein the potency is (i) at least 80%, preferably at least 90%, more preferably at least 100%, even more preferably at least 110%, or most preferably at least 120%, relative to the potency of Met-FGF21; (ii) at least 100%, preferably at least 120%, more preferably at least 140%, even more preferably at least 160%, or most preferably at least 180%, relative to the potency of Met-FGF21; or (iii) at least 200%, preferably at least 250%, more preferably at least 300%, even more preferably at least 350%, or most preferably at least 400%, relative to the potency of Met-FGF21.

164. The FGF21 analogue, according to any one of the preceding embodiments relating to analogues, to the extent possible, in which potency is determined as described in any one of embodiments 70-75.

165. The FGF21 analogue, according to any one of the preceding embodiments relating to analogues, to the extent possible, which is capable of lowering blood glucose in db/db mice relative to a vehicle control.

166. The FGF21 analogue, according to any one of the preceding embodiments relating to analogues, to the extent possible, wherein blood glucose is lowered by at least 1%, preferably by at least 2%, more preferably by at least 3%, even more preferably by at least 4%, or most preferably by at least 5%, based on the mean blood glucose measurements in mM and relative to the corresponding vehicle control.

167. The FGF21 analogue, according to any one of the preceding embodiments relating to analogues, to the extent possible, wherein (i) the db/db mice are male and 9-11 weeks old, (ii) the analogue is administered s.c., (iii) the analogue dosage is in the range of 0.1-1.0 mg/kg, preferably 0.1, 0.2, 0.4, 0.6, 0.8 or 1.0 mg/kg, (iv) the analogue is dosed once daily, preferably on day 1, day 2 and day 3, and/or (v) blood glucose is measured using the glucose oxidase method, preferably using a glucose analyzer such as Biosen 5040.

168. The FGF21 analogue, according to any one of the preceding embodiments relating to analogues, to the extent possible, which is more stable than Met-FGF21 after oxidation by incubation in the presence of 300 mM $H_2O_2$ for 1 hour at 25° C.

169. The FGF21 analogue, according to any one of the preceding embodiments relating to analogues, to the extent possible, in which the stability refers to potency, determined according to any one of embodiments 70-75.

170. The FGF21 analogue, according to any one of the preceding embodiments relating to analogues, to the extent possible, which after incubation with $H_2O_2$ has a potency of at least 15%, preferably at least 20%, more preferably at least 30%, even more preferably at least 40%, or most preferably at least 50%, wherein the potency is relative to Met-FGF21 treated in the same way, however without $H_2O_2$.

171. The FGF21 analogue, according to any one of the preceding embodiments relating to analogues, to the extent possible, which comprises the following amendments as compared to FGF21 (SEQ ID NO:1): (i) Met-Gly- at the N-terminus, (ii) M168L, (iii) embodiment (i) and (ii), (iv) Met-Cys- at the N-terminus, (v) Gly- at the N-terminus, (vi) embodiment (v) and (ii), (vii) Met-Ser- at the N-terminus, or (iix) Ser- at the N-terminus; preferably the FGF21 analogue is selected from the following: (I) Met-Gly-FGF21, (m) Met-Gly-FGF21-M168L, (n) Met-Cys-FGF21, (o) Gly-FGF21-M168L, (p) Gly-FGF21, (q) Met-Ser-FGF21, or (r) Ser-FGF21; wherein FGF21 refers to the polypeptide of SEQ ID NO:1.

172. The FGF21 analogue, according to any one of the preceding embodiments relating to analogues, to the extent possible, which has a P (proline) at position 146, wherein the position number refers to SEQ ID NO:1.

173. The FGF analogue, according to any one of the preceding embodiments to FGF analogues to the extent possible, which is any one of the specific analogues mentioned in the above examples 2 (i.e., 2a-2af), 56 (i.e. 56a-56as) and 57.

174. A composition comprising an analogue of any one of the above embodiments to analogues or a derivative of any one of the above embodiments to derivatives, and a pharmaceutically acceptable carrier.

175. An analogue, according to any one of the preceding embodiments relating to analogues, to the extent possible, preferably according to any one of embodiments 141-173, a derivative, according to any one of the preceding embodiments relating to derivatives, to the extent possible, preferably according to any one of embodiments 1-140, or a composition of embodiment 174, for use as a medicament.

176. An analogue, according to any one of the preceding embodiments relating to analogues, to the extent possible, preferably according to any one of embodiments 141-173, a derivative of any one of embodiments 1-140, or a composition of embodiment 174, for use as a medicament in the treatment or prevention of diabetes, dyslipidemia, obesity, cardiovascular diseases, metabolic syndrome, and/or Non Alcoholic Fatty Liver Disease (NAFLD).

177. An analogue, according to any one of the preceding embodiments relating to analogues, to the extent possible, preferably according to any one of embodiments 141-173, a derivative, according to any one of the preceding embodiments relating to derivatives, to the extent possible, preferably according to any one of embodiments 1-140, or a composition of embodiment 174, for use in the preparation of a medicament for the treatment or prevention of diabetes, dyslipidemia, obesity, cardiovascular diseases, metabolic syndrome, and/or Non Alcoholic Fatty Liver Disease (NAFLD).

178. A method for treating a patient exhibiting diabetes, dyslipidemia, obesity, cardiovascular diseases, metabolic syndrome, and/or Non Alcoholic Fatty Liver Disease (NAFLD) comprising administering to the patient a therapeutically effective amount of an analogue of any one of embodiments 141-173, a derivative of any one of embodiments 1-140, or a pharmaceutical composition of embodiment 174.

179. A method for treating a patient needing intensive care comprising administering to the patient a therapeutically effective amount of an analogue of any one of embodiments 141-173, a derivative of any one of embodiments 1-140, or a pharmaceutical composition of embodiment 174.

180. Any novel combination of embodiments, features and claims described herein.

Various references are cited herein, the disclosures of which are incorporated by reference in their entireties.

EXAMPLES

The following examples serve to illustrate the invention.
Abbreviations

The following abbreviations are used in the following, in alphabetical order: DCM is dichloromethane, DIC is diisopropylcarbodiimide, DIPEA is diisopropylethylamine, DPBS is Dulbecco's Phosphate-Buffered Saline, DVB is divinyl benzene, EDAC is (3-dimethylaminopropyl) ethyl carbodiimide hydrochloride, Fmoc is 9H-fluoren-9-ylmethoxycarbonyl, HEPES is 4-(2-hydroxyethyl)-1-piperazineethanesulfonic acid, HOAt is 1-hydroxy-7-azabenzotriazole, HOBt is 1-hydroxybenzotriazole, HPβCD is Hydroxypropyl Beta Cyclodextrin, HPLC is High Performance Liquid Chromatography, IBMX is 3-isobutyl-1-methylxanthine, Inp is isonipecotic acid, IPTG is isopropyl β-D-1-thiogalactopyranoside check, LCMS is Liquid Chromatography Mass Spectroscopy, MALDI-TOF MS is Matrix-Assisted Laser Desorption/Ionization Time of Flight Mass Spectroscopy, MeOH is methanol, NanoES-MS is Nano-ElectroSpray tandem Mass Spectrometry, NMP is 1-methyl-pyrrolidin-2-one, OEG is 8-amino-3,6-dioxaoctanic acid, OtBu is tert.butyl ester, PBS is phosphate buffered saline, RT is room temperature, TFA is trifluoroacetic acid, THF is tetrahydrofuran, TIPS is triisopropylsilane, Tris is tris(hydroxymethyl)aminomethane or 2-amino-2-hydroxymethylpropane-1,3-diol, Trx is tranexamic acid, TSTU is O-(N-succimidyl)-N,N,N',N'-tetramethyluronium tetrafluoroborate and UPLC is Ultra Performance Liquid Chromatography.

General Methods

LCMS Method 1 (LCMS1)

An Agilent Technologies LC/MSD TOF (G1969A) mass spectrometer was used to identify the mass of the sample after elution from an Agilent 1200 series HPLC system. The deconvolution of the protein spectra was calculated with Agilent's protein confirmation software.
Eluents:
A: 0.1% Trifluoroacetic acid in water
B: 0.1% Trifluoroacetic acid in acetonitrile
Column: Zorbax 5 u, 300SB-C3, 4.8×50 mm
Gradient: 25% -95% acetonitrile over 15 min LCMS Method 2 (LCMS2)

A Perkin Elmer Sciex API 3000 mass spectrometer was used to identify the mass of the sample after elution from a Perkin Elmer Series 200 HPLC system.
Eluents:
A: 0.05% Trifluoroacetic acid in water
B: 0.05% Trifluoroacetic acid in acetonitrile
Column: Waters Xterra MS C-18 X 3 mm id 5 μm
Gradient: 5% -90% acetonitrile over 7.5 min at 1.5 ml/min LCMS Method 3 (LCMS3)

A Waters Micromass ZQ mass spectrometer was used to identify the mass of the sample after elution from a Waters Alliance HT HPLC system.
Eluents:
A: 0.1% Trifluoroacetic acid in water
B: 0.1% Trifluoroacetic acid in acetonitrile
Column: Phenomenex, Jupiter C4 50 X 4.60 mm id 5 μm
Gradient: 10% -90% B over 7.5 min at 1.0 ml/min Example 1

Cloning and Expression of FGF21

The DNA and amino acid sequences for human FGF21 have been disclosed by, e.g., Nishimura et al. in *Biochim. Biophys. Acta* 1492(1):203-206 (2000). The sequences are also available from public databases with accession nos. EMBL:AB021975 and UNIPROT:Q9NSA1, respectively.

The native polypeptide is synthesised with a signal peptide of 28 amino acids for secretion:

```
  1  MDSDETGFEH SGLWVSVLAG LLLGACQAHP IPDSSPLLQF GGQVRQRYLY

51  TDDAQQTEAH LEIREDGTVG GAADQSPESL LQLKALKPGV IQILGVKTSR

101  FLCQRPDGAL YGSLHFDPEA CSFRELLLED GYNVYQSEAH GLPLHLPGNK
```

```
-continued
151 SPHRDPAPRG PARFLPLPGL PPALPEPPGI LAPQPPDVGS SDPLSMVGPS

201 QGRSPSYAS
```

The signal peptide, shown in italics above, is included in the appended sequence listing as SEQ ID NO:2. The mature FGF21 polypeptide consisting of the remaining 181 amino acids is included in the sequence listing as SEQ ID NO:1.

The mature FGF21 polypeptide was cloned and expressed as an intracellular protein in *E. coli*, without the signal peptide, but with an added N-terminal methionine. More in particular, a 550 by coding region including at the 3'-end the ATG codon for Met, as well as Nde1 and BamH1 restriction sites at the 3'- and 5'-ends, respectively, was inserted into the expression vector pET 11c in Nde1-BamH1 under control of the phage T7 promoter, and transformed into *E. coli* B BL21(DE3). The cells were grown in LB amp 100 ug/mL to $OD_{450}$ 0.5, and expression was induced with 0.3 mM IPTG for 4 hours at 37° C. Crude extracts of cells were made by sonication for analysis of FGF21 expression.

A Coomassie stained SDS-PAGE showed successful expression of FGF21 which was identified mainly in the soluble supernatant fraction, with very little in the insoluble pellet. Although the calculated MW of the thus expressed FGF21 (Met-FGF21) (Compound A) is 19.5 kD, it migrated on the gel as a 25 kD protein, which is likely due to the high content of prolines, delaying the movement of the protein.

Example 2

Cloning and Expression of FGF21 Analogues

The following 12 analogues of Met-FGF21 were designed as is known in the art and expressed in *E. coli* as generally described in Example 1 or in *S. cerevisiae* using similar methods:

2a) K122C Met-FGF21 (Compound B),
2b) (K59R, K69R, K122R) Met-FGF21 (Compound C),
2c) (K56R, K69R, K122R) Met-FGF21 (Compound D),
2d) (K56R, K59R, K69R) Met-FGF21 (Compound G),
2e) S71C Met-FGF21 (Compound E),
2f) (K56R, K59R, K69R, K122R) Met-FGF21 (Compound S),
2g) (K56R, K59R, K69R, K122R, I152K) Met-FGF21 (Compound R),
2h) D102T Met-FGF21 (Compound M),
2i) A26E Met-FGF21 (Compound N),
2j) (Q28R, A31 E) Met-FGF21 (Compound P),
2k) Q27E Met-FGF21 (Compound Q) and
21) M168L Met-FGF21 (Compound K).

Still 3 further analogues of Met-FGF21 that were prepared include the following:

2m) (179F, 180E, 181R) Met-FGF21 (Compound X),
2n) (169aT, 171L, 172E, 173A, 174V, 179F, 180E, 181K) Met-FGF21 (Compound Y) and
2o) (166F, 167G, 168L, 169aT, 171L, 172E, 173A, 174V, 179F, 180E, 181K) (Compound Z).

The following 2 analogues of FGF21 were also prepared as described above:

2p) Gly-FGF21-M168L (Compound J) and
2q) Gly-FGF21 (Compound 1).

Still 14 further analogues of FGF21 which are prepared as described above are the following:

2r) S6C-Met-FGF21,
2s) (L118C-A134C, K56R, K59R, K69R, K122R)-Met-FGF21,
2t) (S6K, K56R, K59R, K69R, K122R)-Met-FGF21,
2u) Met-Gly-FGF21,
2v) Met-Gly-FGF21-M168L,
2x) Met-Cys-FGF21,
2y) Met-Ser-FGF21,
2z) (r) MSGSGSGSGSG-FGF21,
2aa) (s) MGGGGG-FGF21,
2ab) (t) MSHSGSGSGSGSGSGSGSGSG-FGF21,
2ac) (u) MSGGGGG-FGF21,
2ad) (v) MSGSGGS-FGF21,
2ae) (x) MSGGSSG-FGF21 and
2af) (y) MSGSGSG-FGF21.

Example 3

Purification of FGF21 and Analogues

The FGF21 polypeptide and its analogues prepared as described in Examples 1-2 were further purified as follows or using similar technics:

A slurry (20% w/v) of *E.coli* in 10 mM potassium phosphate buffer pH 7.5 was sonicated (3 seconds on/off intervals on ice for 5 minutes). The polypeptide was pelleted by centrifugation (10,000×g, for 30 minutes), re-solubilised by sonication in 50 mM Tris pH 8.0, and debris removed by centrifugation (10,000×g, for 30 minutes). The polypeptide in the resulting supernatant was purified by anion exchange chromatography (50 mM Tris pH 8.0, 50-250 mM NaCl) using Q Sepharose Fast Flow resin (GE Healthcare), as generally described in *Protein Purification*. Principles and Practice Series: Springer Advanced Texts in Chemistry Scopes, Robert K. 3rd ed., 1994. In some instances, further purification was done by size exclusion chromatography using a HiLoad 26/60 Superdex pg 75 column (GE Healthcare) operated with 50 mM Tris pH 8.0 and 200 mM NaCl. For storage the polypeptide was transferred to 50 mM ammonium bicarbonate pH 7.9, lyophilized and kept at −80° C.

Example 4

Derivatisation of FGF21 Compounds at Cys with Albumin Binders

Albumin binders containing a maleimide may be synthesised as described in the following and FGF21 and analogues thereof containing a free cysteine may be derivatised with such albumin binders as also described in the following.

Preparation of 17-(S)-1-carboxy-3-{2-[2-({2-[2-({2-[3-(2,5-dioxo-2,5-dihydro-pyrrol-1-yl)-propionylamino]-ethylcarbamoyl}-methoxy)-ethoxy]-ethylcarbamoyl}-methoxy)-ethoxy]-ethylcarbamoyl}-propylcarbamoyl)-heptadecanoic acid Step 1: Fmoc-ethylenediamine 2-chlorotrityl resin 5.8 g (7.5 mmol) 2-Chlorotrityl chloride resin (100-200 mesh, 1% DVB, loaded 1.3 mmol/g) was swollen in DCM (80 mL) for ca 1 h and then it was drained. Fmoc-ethylene diamine hydrogen chloride was suspended in NMP (30 mL)

and DCM (30 mL) and DIPEA (5 eq, 6.42 mL). This suspension was added to the resin and shaken for 3 h. The resin was drained and washed with 17:2:1, DCM:MeOH:DIPEA, DCM, NMP and DCM (3×80 mL). It was dried over KOH/NaOH in a dessicator.

Step 2: Fmoc-OEG-ethylenediamine 2-chlorotrityl resin 3 mmol of the Fmoc-ethylenediamine 2-chlorotrityl resin was modified using a CEM Liberty microwave peptide synthesizer and Fmoc-based solid-phase peptide methodology. The resin was swollen in NMP (60 mL) and drained.

The resin was Fmoc deprotected using 5% piperidine in NMP (60 mL), heated for 30 sec, drained, washed with NMP (60 ml), followed by additional 5% piperidine in NMP (60 mL), heated for 3 min at 70-75° C., followed by washing with NMP (4×60 mL). A 0.3 M solution of Fmoc-8-amino-3,6-dioxaoctanic acid +0.3 M HOAt in NMP (45 mL) was added to the resin followed by addition of a 0.75 M solution of DIC in NMP (18 mL). The reaction was heated to 70-75° C. for 10 min, followed by a wash with NMP (4×60 mL).

Step 3: Fmoc-OEG-OEG-ethylenediamine 2-chlorotrityl resin

The resin was Fmoc deprotected using 5% piperidine in NMP (60 mL), heated for 30 sec, drained, washed with NMP (60 ml), followed by additional 5% piperidine in NMP (60 mL), heated for 3 min at 70-75° C. followed by washing with NMP (4×60 mL). A 0.3 M solution of Fmoc-8-amino-3,6-dioxaoctanic acid +0.3 M HOAt in NMP (45 mL) was added to the resin, followed by addition of a 0.75 M solution of DIC in NMP (18 mL). The reaction was heated to 70-75° C. for 10 min followed by a wash with NMP (4×60 mL).

Step 4: Fmoc-gamma-Glu-OEG-OEG-ethylenediamine 2-chlorotrityl resin

The resin was Fmoc deprotected using 5% piperidine in NMP (60 mL), heated for 30 sec, drained, washed with NMP (60 ml), followed by additional 5% piperidine in NMP (60 mL), heated for 3 min at 70-75° C., followed by washing with NMP (4×60 mL). A 0.3M solution of Fmoc-Glu-OtBu+0.3 M HOAt in NMP (45 mL) was added to the resin, followed by addition of a 0.75M solution of DIC in NMP (18 mL). The reaction was heated to 70-75° C. for 10 min, followed by a wash with NMP (4×60 mL).

Step 5: C18-diacid-gamma-Glu-OEG-OEG-ethylenediamine 2-chlorotrityl resin

The resin was Fmoc deprotected using 5% piperidine in NMP (60 mL), heated for 30 sec, drained, washed with NMP (60 ml), followed by additional 5% piperidine in NMP (60 mL), heated for 3 min at 70-75° C., followed by washing with NMP (4×60 mL). A 0.3M solution of octadecanedioic acid mono-tert-butyl ester+0.3 M HOAt in NMP (45 mL) was added to the resin, followed by addition of a 0.75M solution of DIC in NMP (18 mL). The reaction was heated to 70-75° C. for 10 min, followed by a wash with NMP (4×60 mL).

Step 6: 17-[(S)-3-(2-{2-[(2-{2-[(2-amino-ethylcarbamoyl)-methoxy]-ethoxy}-ethylcarbamoyl)-methoxy]-ethoxy}-ethylcarbamoyl)-1-carboxy-propylcarbamoyl]-heptadecanoic acid The resin was treated with TFA/TIPS/water 95:2.5:2.5 for 1 h. The resin was filtered off and the filtrate was concentrated under vacuum. Acetonitrile was added and the sample was re-concentrated. The crude product was purified by HPLC (10-50% acetonitrile, 0.1% TFA, 60 mL/min, C18, 50 mm×200 mm, 15 Å)
LCMS2 m/z: 777 (M+1).

Step 7: 17-((S)-1-carboxy-3-{2-[2-({2-[2-({2-[3-(2,5-dioxo-2,5-dihydro-pyrrol-1-yl)-propionyl-amino]-ethylcarbamoyl}-methoxy)-ethoxy]-ethylcarbamoyl}-methoxy)-ethoxy]-ethyl-carbamoyl}-propylcarbamoyl)-heptadecanoic acid N-maleoyl-beta-alanine (0.65 mmol, 110 mg) was dissolved in NMP. EDAC (0.65 mmol, 125 mg) and HOBt (0.65 mmol, 88 mg) were added, and the mixture was stirred for 1 h at RT. A solution of 17-[(S)-3-(2-{2-[(2-{2-[(2-amino-ethylcarbamoyl)-methoxy]-ethylcarbamoyl}-methoxy]-ethoxy}-ethylcarbamoyl)-1-carboxy-propylcarbamoyl]-heptadecanoic acid (0.65 mmol, 504 mg) in NMP (5 ml) was added, and the mixture was stirred for 16 h at RT. The crude product was purified by HPLC (25-65% acetonitrile, 0.1% TFA, 60 mL/min, C18, 50 mm×200 mm, 15 Å) to yield 200 mg of the title compound.
LCMS2 m/z: 927.8 (M+1).

Preparation of the K122C Met-FGF21 derivative S-122-[1-(2-{2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-ethyl)-2,5-dioxo-pyrrolidin-3-yl] [Cys122] Met-FGF21 (Compound F)

The Cys residue at position 122 in the K122C Met-FGF21 analogue, prepared as described in Examples 2 and 3 (SEQ ID NO:1 with K122C and an N-terminal M), was modified at the thiol group with the following reagent, which was prepared as described above:

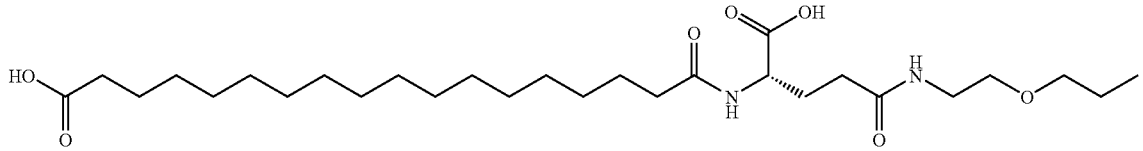

-continued

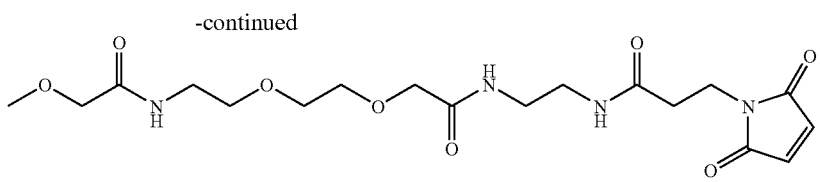

[Cys122]-Met-FGF21 (lyophilized) was dissolved in 20 mM Tris buffer pH 7.5 and buffer exchanged to 20 mM Tris buffer using PD-10 columns (GE Healthcare 170851-01). To 7 ml (1.48 µmol) of this solution (4.1 mg/ml) was added 1.5 ml of a solution containing 17-((S)-1-carboxy-3-{2-[2-({2-[2-({2-[3-(2,5-dioxo-2,5-dihydro-pyrrol-1-yl)-propionylamino]-ethylcarbamoyl}-methoxy)-ethoxy]-ethylcarbamoyl}-methoxy)-ethoxy]-ethylcarbamoyl}-propylcarbamoyl)-heptadecanoic acid in acetonitrile/Tris buffer (1.3:1) (2.96 µmol). The reaction was allowed to react at RT for 1 h. The reaction mixture was filtered through a 0.22 um filter and was purified using a size exclusion chromatography (GE Healthcare, Superdex 200, 26/60) eluting with 20 mM Tris buffer pH 7.5, followed by ion exchange chromatography (Mono-Q 5/50, gradient from 0-0.5 M NaCl in 20 mM Tris, pH 7.5 over 60 column volumes). After analysis by LCMS and SDS-PAGE the relevant fractions were pooled and buffer exchanged to 50 mM $NH_4HCO_3$ and lyophilized.
LCMS1: Theoretical mass =20442.2, found 20442.3

Example 5

Preparation of another Cys Derivative of an FGF21 Analogue

Preparation of the S71C Met-FGF21 derivative S-71-[1-(2-{2-[2-(2-{2-[2-(2-{2-[(S)-carboxy-4-(19-carboxy-nonadecanoylamino)-butyrylamino]-ethoxy}-ethoxy)-acetylamino]-ethoxy}-ethoxy)-acetylamino]-ethylcarbamoyl}-ethyl)-2,5-dioxo-pyrrolidin-3-yl] [Cys71]Met-FGF21 (Compound H)

Preparation of 19-((S)-1-Carboxy-3-{2-[2-({2-[2-({2-[3-(2,5-dioxo-2,5-dihydro-pyrrol-1-yl)-propionylamino]-ethylcarbamoyl}-methoxy)-ethoxy]-ethylcarbamoyl}-methoxy)-ethoxy]-ethylcarbamoyl}-propylcarbamoyl)-nonadecanoic acid Step 1: 19-{(S)-1-tert-Butoxycarbonyl-3-[2-(2-{[2-(2-carboxymethoxy-ethoxy)-ethyl-carbamoyl]-methoxy}-ethoxy)-ethylcarbamoyl]-propylcarbamoyl}-nonadecanoic acid tert-butyl ester:

To a solution of 2-(19-tert-Butoxycarbonylnonadecanoylamino)pentanedioic acid 1-tert-butyl ester 5-(2,5-dioxopyrrolidin-1-yl) ester (2.50 g) and [2-(2-{2-[2-(2-Aminoethoxy)-ethoxy]-acetylamino}-ethoxy)-ethoxy]-acetic acid (1.47 g) in ethanol (40 ml) was added DIPEA (1.26 ml). The mixture was stirred at room temperature over night and then concentrated in vacuo. To the residue was added aqueous 0.1 N HCl (150 ml) and ethyl acetate (200 ml). The layers were separated and the aqueous layer was extracted with ethyl acetate (100 ml). The combined organic layers were washed with water and brine, dried (magnesium sulphate) and concentrated in vacuo to give an oil, which crystallised on standing. Yield 96% (3.1 g). LCMS3: Theoretical mass: 874.2. Found: 874.49.

Step 2: 19-((S)-1-tert-Butoxycarbonyl-3-{2-[2-({2-[2-(2,5-dioxo-pyrrolidin-1-yloxycarbonyl-methoxy)-ethoxy]-ethylcarbamoyl}-methoxy)-ethoxy]-ethylcarbamoyl}-propylcarbamoyl)-nonadecanoic acid tert-butyl ester:

To a solution of 19-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-nonadecanoic acid tert-butyl ester (3.1 g) in acetonitrile (50 ml) was added TSTU (1.39 g) and DIPEA (0.91 ml). The mixture was stirred at room temperature over night and then concentrated in vacuo. To the residue was added aqueous 0.1 N HCl (100 ml) and ethyl acetate (200 ml). The layers were separated and the aqueous layer was extracted with ethyl acetate (50 ml). The combined organic layers were washed with water and brine, dried (magnesium sulphate) and concentrated in vacuo to give an oil. Yield 99% (3.4 g). LCMS3: Theoretical mass: 971.2 Found: 971.8.

Step 3: 19-((S)-1-Carboxy-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-nonadecanoic acid 19-((S)-1-tert-Butoxycarbonyl-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-nonadecanoic acid tert-butyl ester (3.4 g) was stirred in TFA (75 ml) for 45 min and then concentrated in vacuo. The residue was concentrated with toluene 3 times to give a solid. The residue was crystallised in 2-propanol and filtered to give a white crystalline compound. Yield 80% (2.4 g). LCMS3: Theoretical mass: 859.03 Found: 859.44.

Step 4: 3-(2,5-Dioxo-2,5-dihydropyrrol-1-yl)propionic acid 2,5-dioxopyrrolidin-1-yl ester Malimidopropionic acid (500 mg) was dissolved in dry THF (15 ml). TSTU (790 mg) and DIPEA (0.62 ml) was added. The mixture was stirred at room temperature under nitrogen over night. The yellow thick suspension was concentrated. The residue was dissolved in DCM and extracted with 0.1 N HCl (2×) and brine (1×). The organic layer was dried ($Na_2SO_4$) and concentrated to give a white solid. LCMS3: Theoretical mass: 266.21 Found: 267.26 (M+1).

Step 5: 19-((S)-1-Carboxy-3-{2-[2-({2-[2-({2-[3-(2, 5-dioxo-2,5-dihydro-pyrrol-1-yl)-propionylamino]-ethylcarbamoyl}-methoxy)-ethoxy]-ethylcarbamoyl}-methoxy)-ethoxy]-ethylcarbamoyl}-propylcarbamoyl)-nonadecanoic acid To a solution of N-butoxycarbonyl ethylenediamine (70 mg) in acetonitrile (4 ml) was added DIPEA (0.07 ml) and 3-(2,5-Dioxo-2,5-dihydropyrrol-1-yl)propionic acid 2,5-dioxopyrrolidin-1-yl ester (100 mg) was added. After stirring for 1 h the mixture was concentrated in vacuo. The residue was dissolved in DCM and washed with 5% Citric acid, dried with magnesium sulphate and concentrated. To the residue was added TFA (8 ml). After stirring for 1 h at RT the mixture was concentrated in vacuo and co-concentrated with toluene twice. The residue was dissolved in THF (5 ml). 19-((S)-1-Carboxy-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-nonadecanoic acid (75 mg) and DIPEA (0.09 ml) was added. The mixture was stirred at RT over night. Purification by HPLC using A-buffer: 0.1% TFA in water and B-buffer: 0.1% TFA in acetonitrile. Gradient 10-80%B over 45 min. Flow: 20 ml/min, C18 column 30 mm×250 mm, 110 Å. Yield 116 mg (34%).
LCMS3: Theoretical mass: 955.17 Found: 955.7

The Cys residue at position 71 in the S71C Met-FGF21 analogue, prepared as generally described in Examples 2 and 3 (SEQ ID NO:1 with S71C and an N-terminal M), was modified at the thiol group at position 71 with the reagent prepared as described above:

superdex 200 prep grade in DPBS-buffer from Bio Whittaker. Yield 0.466 g.
LCMS1: Theoretical mass: 20511.3 Found: 20511.3

Example 6

Preparation of a Further Cys Derivative of an FGF21 Analogue

Preparation of the S71C Met-FGF21 derivative S-71-({2-[2-(2-{2-[2-(2-{2-[(S)-4-(19-carboxy-nonadecanoylamino)-butyrylamino]-ethoxy}-ethoxy)-acetylamino]-ethoxy}-ethoxy)-acetylamino]-ethylcarbamoyl}-methyl) [Cys71] Met-FGF21 (Compound O)

Preparation of 9-{(S)-1-carboxy-3-[2-(2-{[2-(2-{[2-(2-iodo-acetylamino)-ethylcarbamoyl]-methoxy}-ethoxy)-ethylcarbamoyl]-methoxy}-ethoxy)-ethylcarbamoyl]-propylcarbamoyl}-nonadecanoic acid Step 1: 19-[(S)-3-(2-{2-[(2-{2-[(2-Amino-ethylcarbamoyl)-methoxy]-ethoxy}-ethylcarbamoyl)-methoxy]-ethoxy}-ethylcarbamoyl)-1-tert-butoxycarbonyl-propylcarbamoyl]-nonadecanoic acid tert-butyl ester To a solution of 19-{(S)-1-tert-butoxycarbonyl-3-[2-(2-{[2-(2-carboxymethoxy-ethoxy)-ethylcarbamoyl]-methoxy}-ethoxy)-ethylcarbamoyl]-propylcarbamoyl}-nonadecanoic acid tert-butyl ester (500 mg) in acetonitrile

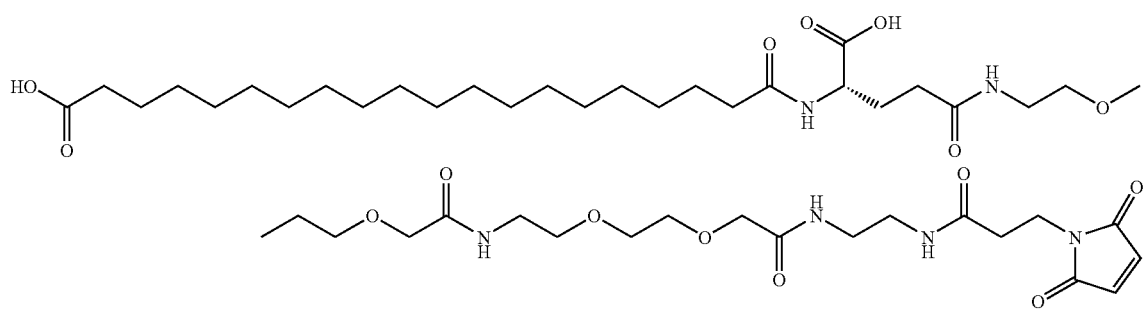

[Cys71] Met-FGF21 (1.68 mg, 85.9 nmol) freeze dried from NH$_4$HCO$_3$ was dissolved in MiliQ water (1 ml). The buffer was exchanged to 0.02M Tris, pH 7.8 on a PD 10 column (GE healthcare 179851-01). An eluate of approximately 3.5 ml was collected. To this eluate 19-((S)-1-carboxy-3-{2-[2-({2-[2-({2-[3-(2,5-dioxo-2,5-dihydro-pyrrol-1-yl)-propionylamin]-ethylcarbamoyl}-methoxy)-ethoxy]-ethylcarbamoyl}-methoxy)-ethoxy]-ethylcarbamoyl}-propylcarbamoyl)-nonadecanoic acid (0.86 umol) in 0.02M Tris, pH 7.8/acetonitril 1:1 (0.205 ml) was added. The mixture was left at room temperature for 1 h and then at 5° C. over night. Purification by anion exchange on a monoQ 5/50 GL column using A-buffer: 20 mM Tris, pH 7.8; B-buffer: 20 mM Tris, 50 mM NaCl, pH 7.8, flow 0.5 ml and a gradient from 0-100% B over 20 CV. The isolated fractions containing product were further purified by size exclusion chromatography on a HiLoad 26/60

(15 ml) was added TSTU (224 mg) and DIPEA (0.13 ml). After stirring for 2 h at RT this mixture was poured into a solution of ethylene-diamine (0.50 ml) in acetonitrile (5 ml). After stirring for 2 h the mixture was concentrated in vacuo. The residue was stirred in 1 N NaOH (100 ml) and ethyl acetate (400 ml). The layers were separated. The organic layer was dried with magnesium sulphate and concentrated in vacuo to give a white solid. This solid was stirred in ethanol and then filtrated. The filtrate was concentrated to give a sirup. Yield 250 mg (48%)
LCMS3: Theoretical mass: 916.26 Found: 916.7

Step 2:. 19-{(S)-1-tert-Butoxycarbonyl-3-[2-(2-{[2-(2-{[2-(2-iodo-acetylamino)-ethyl-carbamoyl]-methoxy}-ethoxy)-ethylcarbamoyl]-methoxy}-ethoxy)-ethylcarbamoyl]-propylcarbamoyl}-nonadecanoic acid tert-butyl ester To a solution of iodoacetic acid (60 mg) in DCM (8 ml) was added TSTU (90 mg) and DIPEA (0.05 ml). After stirring at RT for 60 min a solution of 19-[(S)-3-(2-{2-[(2-{2-[(2-amino-ethylcarbamoyl)-methoxy]-ethoxy}-ethylcarbamoyl)-methoxy]-ethoxy}-ethyl-carbamoyl)-1-tert-butoxycarbonyl-propylcarbamoyl]-nonadecanoic acid tert-butyl ester (0.25 g) in DCM (8 ml) and DIPEA (0.05 ml) was added. After stirring for 120 min, the mixture was diluted with DCM (100 ml) and 1 N HCl (50 ml) was added. The layers were separated. The organic layer was dried with magnesium sulphate and concentrated in vacuo. The residue was co-concentrated with ethanol to give a solid compound. Yield 225 mg (76%).

LCMS3: Theoretical mass: 1084.2 Found: 1084.8

Step 3: 19-{(S)-1-Carboxy-3-[2-(2-{[2-(2-{[2-(2-iodo-acetylamino)-ethylcarbamoyl]-methoxy}-ethoxy)-ethylcarbamoyl]-methoxy}-ethoxy)-ethyl-carbamoyl]-propylcarbamoyl}-nonadecanoic acid 19-{(S)-1-tert-Butoxycarbonyl-3-[2-(2-{[2-(2-{[2-(2-iodo-acetylamino)-ethyl-carbamoyl]-methoxy}-ethoxy)-ethylcarbamoyl]-methoxy}-ethoxy)-ethylcarbamoyl]-propyl-carbamoyl}-nonadecanoic acid tert-butyl ester (225 mg) was treated with TFA (10 ml) for 90 min. The mixture was concentrated in vacuo and co-concentrated with toluene twice. The residue was purified by HPLC using A-buffer: 0.1% TFA in water and B-buffer: 0.1% TFA in acetonitrile. Gradient 10-80% B over 45 min. Flow: 20 ml/min, C18 column 30 mm×250 mm, 110 Å. Yield 45 mg (22%).

LCMS3: Theoretical mass: 971.98 Found: 972.6

The Cys residue at position 71 in the S71C Met-FGF21 analogue, prepared as generally described in Examples 2 and 3 (SEQ ID NO:1 with S71C and an N-terminal M), was modified at the thiol group with the following reagent:

General Procedure A

[Cys71] Met-FGF21 (7.53 mg, 385 nmol), freeze dried from $NH_4HCO_3$, was dissolved in 3×350 ul 0.02M Tris, pH 7.8, and buffer exchanged through PD 10 columns to 0.02M Tris, pH 7.8. Approximately 3.5 ml was collected. 19-{(S)-1-Carboxy-3-[2-(2-{[2-(2-{[2-(2-iodo-acetylamino)-ethyl-carbamoyl]-methoxy}-ethoxy)-ethylcarbamoyl]-methoxy}-ethoxy)-ethylcarbamoyl]-propylcarbamoyl}-nonadecanoic acid (1.5 mg), which was prepared as described above, was dissolved in 0.02M Tris, pH 7.8 buffer/acetonitrile 1:1 (0.75 ml). To the solution of [Cys71] Met-FGF21 was added iodo acetamide solution (0.561 ml, 3 eq). The acetonitrile concentration was 7%. The mixture was left at RT for 70 h. The mixture was ultra filtrated in Amicon Ultra-4 centrifugal device MWCO 10000 at 4000 g for 10 min. Ultrafiltration with approximately 4 ml A-buffer was repeated for another 4 times to remove reagent. The sample was purified by anion exchange on a monoQ 5/50 GL column using A-buffer: 20 mM TRIS, pH 7.8; B-buffer: 20 mM TRIS, 50 mM NaCl, pH 7.8, flow 0.5 ml and a gradient from 0-100% B over 60CV. The isolated fractions containing product were pooled and concentrated by ultracentrifugation in Amicon Ultra-4 centrifugal device MWCO 10000 at 6000 rpm for 2×10 min.

A buffer exchange to 50 mM $NH_4HCO_3$ was made using PD 10 (GE 179851-01) columns. Approximately 4.0 ml eluate was collected. This was filtered through a Millex GV sterile 0.22 um filter and freeze dried. Yield 2.18 mg.

LCMS1: Theoretical mass: 20400.2 Found: 20400.13

Example 7

Derivatisation of FGF21 Compounds at the N-Terminus with Albumin Binders

Preparation of the (K56R, K59R, K69R, K122R) Met-FGF21 derivative N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Arg56, Arg59, Arg69, Arn122] Met-FGF21 (Compound V)

The N-terminal Met residue in the K56R, K59R, K69R, K122R Met-FGF21 analogue, prepared as generally described in Examples 2 and 3 (SEQ ID NO:1 with K56R, K59R, K69R, and K122R and an N-terminal M), was modified at the alpha amino group with the following reagent:

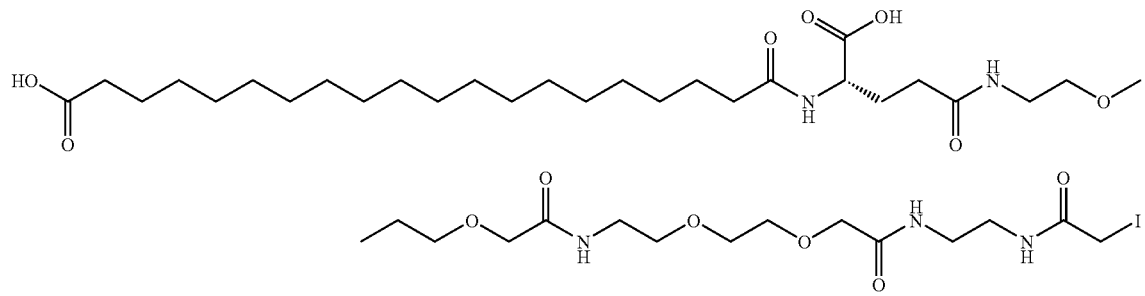

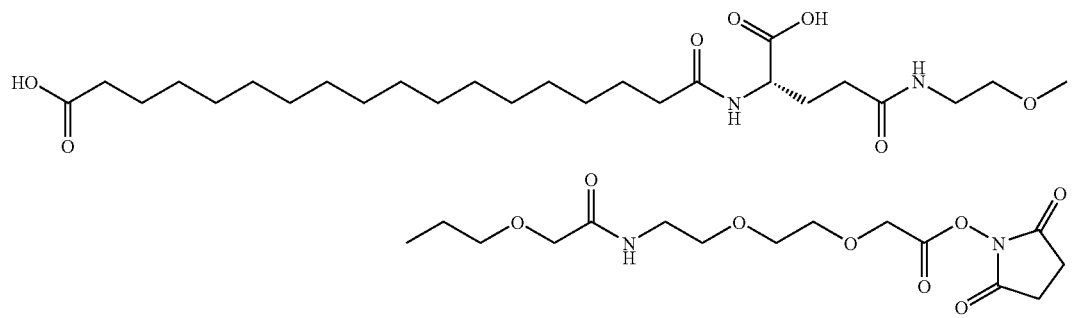

[Arg56, Arg59, Arg69, Arg122] Met-FGF21 (lyophilized) was dissolved in DPBS buffer and buffer exchanged to DPBS buffer using PD-10 columns (GE Healthcare170851-01) yielding 3.5 ml (4.3 mg/ml, 0.77 μmol). The sample was diluted with DPBS buffer (10.5 ml) and a solution of 17-((S)-1-carboxy-3-{2-[2-({2-[2-(2,5-dioxo-pyrrolidin-1-yloxycarbonyl-methoxy)-ethoxy]-ethylcarbamoyl}-methoxy)-ethoxy]-ethylcarbamoyl}-propylcarbamoyl)-heptadecanoic acid (6.2 μmol), which was prepared as generally described in Example 4, in acetonitrile (7.5 ml) was added. After 1 h at RT, the mixture was cooled to 0° C. and cold 0.2 M NaOH (21 ml) was added. After 30 min at 0° C. the mixture was neutralized with hydrochloric acid. The mixture was concentrated using Amicon Centriprep ultracel YM10 centrifugal filters (10000 MWCO), then diluted with 5 ml 20 mM Tris buffer, pH 7.5 and re-concentrated twice (final volume approximately 5 ml). The solution mixture was filtered through a 0.22 um filter and was purified by ion exchange chromatography and lyophilized as described in Example 4.
LCMS1: Theoretical mass: 20368.1 Found: 20367.2

Example 8

Potency Assay—Glucose Uptake in 3T3-L1 Adipocytes

The following assay was used for determining the biological activity, or potency, of FGF21 compounds of the invention.

Mouse 3T3-L1 fibroblasts (e.g. available from ATCC, catalogue no. CL-173) are maintained in basal medium (DMEM (4500 mg/l Glucose) with 10% Fetal Bovine Serum (FBS) and Penicillin/Streptomycin). The cells are not allowed to reach confluence and should be passed (transferred to new vials) before reaching approx. 60% of confluency (by visual inspection).

For the glucose uptake assay, cells are plated 80,000 cells/well in a 24 well plate, or 20,000 cells/well in a 96 well plate, and when they reach confluency (high density, with a view to have differentiated adipose cells made), the medium is changed from basal medium to basal medium containing Troglitazone, IBMX, Dexamethasone (commercially available from, e.g., Sigma) and human insulin (commercially available from, e.g., Novo Nordisk A/S).

The cells are used 7-14, preferably 7-10, days after initiation of differentiation. The cells are stimulated with increasing concentrations (0-300 nM) of the FGF21 polypeptides or derivatives of the invention for 20 hours in basal medium. Before addition of 3H-deoxy-glucose (in what follows: the tracer) the cells are washed in warm (approximately 37° C.) assay buffer (PBS with 1 mM $MgCl_2$ and 2 mM $CaCl_2$), HEPES and 0.1% Human serum albumin) and the cells are incubated with the tracer for 1 hour. This incubation is terminated by washing twice in ice cold assay buffer. The cells are lysed with Triton X-100 and lysates transferred to a 96 wells plate, microscint-40 (commercially available from, e.g., Perkin Elmer) is added and amount of tracer counted in a TOP-counter (e.g. a Packard top-counter from Perkin Elmer). The $EC_{50}$ of the polypeptide in question is calculated. The results which are shown in Table 1 below indicate the $EC_{50}$ (potency) of the FGF21 compounds of the invention relative to that of Met-FGF21.

TABLE 1

Potency of FGF21 compounds

| Compound from Example number | Compound | Glucose uptake 3T3-L1 Potency (%) rel. to Met-FGF21 |
|---|---|---|
| 1 | A | 100 |
| 56h | | 20 |
| 56m | | 114 |
| 56l | | 198 |
| 2i | I | 91 |
| 56af | | 8 |
| 2p | J | 60 |
| 56as | | 9 |
| 56ae | | 10 |
| 56am | | 47 |
| 56ao | | 133 |
| 56c | | 38 |
| 47 | | 1 |
| 56a | T | 50 |
| 46 | | 10 |
| 53 | | 12 |
| 54 | | 25 |
| 56g | | 667 |
| 49 | | 111 |
| 56b | U | 33 |
| 48 | | 6 |
| 56ab | | 4 |
| 56k | | 209 |
| 56j | | 341 |
| 16 | | 131 |
| 56ag | | 403 |
| 15 | | 182 |
| 56x | | 27 |
| 56r | | 91 |
| 2h | M | 106 |
| 56ar | | 46 |
| 56z | | 122 |
| 2a | B | 57 |
| 4 | F | 52 |
| 56ac | | 520 |
| 56ad | | 700 |
| 56s | | 68 |
| 2o | Z | 356 |
| 56ai | | 7 |
| 21 | K | 36 |
| 56aj | | 5 |

TABLE 1-continued

Potency of FGF21 compounds

| Compound from Example number | Compound | Glucose uptake 3T3-L1 Potency (%) rel. to Met-FGF21 |
|---|---|---|
| 2n | Y | 45 |
| 56u | | 14 |
| 2m | X | 6 |
| 56t | | 5 |
| 2i | N | 85 |
| 2k | Q | 72 |
| 2j | P | 48 |
| 2d | G | 89 |
| 2f | S | 45 |
| 7 | V | 19 |
| 2g | R | 26 |
| 2c | D | 67 |
| 2b | C | 130 |
| 2 | | 36 |
| 2e | E | 52 |
| 5 | H | 3 |
| 6 & 12 | O | 6 |
| 13 | | 1 |
| 14 | | 5 |
| 56aa | | 13 |
| 56ah | | 443 |
| 56al | | 4 |
| 56f | | 600 |
| 56i | | 329 |
| 56d | | 10 |
| 55 | | 1 |
| 56y | | 7 |

It appears from the results of Table 1 that the FGF21 compounds of the invention have an acceptable, some even a very fine potency as compared to the potency of Met-FGF21.

Example 9

Oxidation Stability of FGF21 Compounds

The oxidative stability of a number of FGF21 compounds of the invention was determined in accelerated experiments using hydrogen peroxide.

The compound in question, e.g. Met-FGF21, dissolved in PBS, pH 7.2, at a concentration of 51 μM (1 mg/mL) was incubated for 1 hour at 25° C. in the presence of 300 mM $H_2O_2$. The control (not oxidized Met-FGF21) was treated in the same way, however without $H_2O_2$. The reactions were terminated by desalting on a gel filtration column (Zeba or Superose 12) equilibrated in PBS.

Oxidation status and kinetics of the two Met residues (the N-terminal met in wild type Met-FGF21, SEQ ID NO:1 with an N-terminal met, in what follows "Met1", and Met168 in SEQ ID NO:1, in what follows "Met168") was determined by peptide mapping using the digestive enzyme trypsin (see e.g. Patten, SMV et al., Journal of biological chemistry, 274, 10268-10276, 1999), at an enzyme:substrate (i.e., trypsin:FGF21) ratio of 1:100 (w/w) for 2-18 h at 37° C. The resultant digests were quenched with 1% TFA and mapped by reverse phase UPLC (Waters) on a C18 column. Peptide elution was monitored by absorbance at 214 nm. Peptides were collected, dried in a speed-vac, and reconstituted in 50% acetonitrile, 0.1% formic acid. Mass spectrometry of collected peptides, digests and intact protein was carried out using MALDI-TOF MS (Bruker Daltonics, autoflex II, ToF/ToF) and NanoES-MS (Q-ToF Ultima, Waters) using NanoES spray capillaries.

Analysis of non-oxidized and oxidized Met-FGF21 samples by UPLC demonstrated complete oxidation of the Met1 and Met168 residues to Met-S-oxide (sulfoxide) in the digests at 300 mM $H_2O_2$ (1 h, 25° C.). MALDI analysis of collected peptides confirmed sites of oxidation to the Met1 and Met168 containing peptides and the Met residues were shown to be oxidized to Met-S-oxide using MS/MS sequencing of the peptides. Similar oxidation kinetics of the two residues was observed in the presence of various hydrogen peroxide concentrations (25, 50, 100, 200, and 300 mM $H_2O_2$ incubated for 30 min at 0° C.) using MALDI and UPLC analysis. The half-lives determined by UPLC for peptide 1-18 and peptide 137-176 were 36.3 and 40.3 min, respectively. Oxidation products were also observed by direct analysis of the intact protein using NanoES-MS.

The activity of oxidized Met-FGF21 was reduced to 10% compared to non-oxidized Met-FGF21 in the fat cell assay of Example 8.

In a similar way, the oxidation stability of a number of FGF21 compounds of the invention are determined, and the results are shown in Table 2 below. The oxidation conditions were 300 mM $H_2O_2$, 1 h, 25° C.

TABLE 2

Potency of FGF21 compounds

| FGF21 compound | $EC_{50}$ relative to the $EC_{50}$ of Met-FGF21 (%) |
|---|---|
| Met-FGF21 (control) (Compound A) | 100 |
| Met-FGF21 + Oxidation | 10 |
| Gly-FGF21 | 88 |
| Gly-FGF21-M168L | 60 |
| Met-FGF21-M168L (Compound A1) | 36 |

Example 10

In Vivo Test of FGF21 Compounds—Pharmacodynamics

The db/db mouse is a mouse model for Type 2 diabetes. The mice lack the leptin receptor and they are characterized by hyperglycemia, insulin resistance, hyperphagia and obesity.

Male db/db mice (9-11 weeks old) were used to measure the effect on blood glucose of the following FGF21 compounds: (1) Wild type FGF21 (SEQ ID NO:1 with an N-terminal Met), (2) the K122C analogue of FGF21 with an N-terminal Met, derivatised at Cys122 with an albumin binder as described in Example 4 (in two dosages), and (3) the S71C analogue of FGF21 with an N-terminal Met, derivatised at Cys71 with an albumin binder as described in Example 6. The analogues were expressed in E. coli as described in Examples 1-2 and purified as described in Example 3.

The compounds were administered s.c. 0.2-1.0 mg/kg in PBS once daily (dosing on day 1, day 2 and day 3). The vehicle treated group (control) was treated with PBS, (250 ul/50 g mouse) s.c. once daily. Blood glucose levels were measured on day 0, 1, 3, 4 and 5 using a glucose analyzer (Biosen 5040) based on the glucose oxidase method. On day 0 the blood glucose was measured in order to allocate the mice to 4 different groups, with 8-10 mice in each, with a mean blood glucose which does not significantly differ from each other. On day 1, blood glucose was measured 2 hours after first dose. On day 3 blood glucose was measured 2 hours after the third dose. On day 4 blood glucose was measured 24 hours after the third dose. The blood sample on day 5 was taken, and blood glucose thus measured, 48 hours after the last (third) dose.

The results are shown in Table 3 below, in which blood glucose is indicated in mM (mean±S.E.M (n=8 or 10).

TABLE 3

Effect on Blood glucose in db/db mice

| Treatment/Dosage | Day 0 | Day 1 | Day 3 | Day 4 | Day 5 |
|---|---|---|---|---|---|
| Vehicle | 21.7 ± 1.4 | 23.6 ± 1.2 | 22.8 ± 1.1 | 22.3 ± 2.1 | 23.9 ± 1.6 |
| Met-FGF21/0.24 mg/kg | 21.6 ± 1.0 | 24.0 ± 0.8 | 20.5 ± 1.2 | 20.6 ± 1.8 | 22.5 ± 1.9 |
| Derivative of Example 4/0.22 mg/kg (Compound F) | 22.8 ± 1.5 | 21.0 ± 1.4 | 18.5 ± 1.4 | 14.7 ± 1.3 | 17.1 ± 1.5 |
| Derivative of Example 4/0.70 mg/kg (Compound F) | 21.5 ± 1.7 | 17.3 ± 2.2 | 13.8 ± 1.8 | 11.6 ± 1.5 | 13.6 ± 1.5 |
| Derivative of Example 6/1.01 mg/kg (Compound O) | 20.6 ± 2.0 | 16.8 ± 2.0 | 15.7 ± 2.1 | 12.4 ± 2.2 | 12.9 ± 1.5 |

The results show that the FGF21 derivatives of the invention are biologically active in vivo, viz. they effectively lower blood glucose as compared to the vehicle. The derivatives of the invention even seem to be more effective than wild type FGF21 with respect to their blood lowering capacity as well as the duration of action.

Example 11

In Vivo Test of FGF21 Compounds—Pharmacokinetics db/db Mice

The pharmokinetic profile of FGF21 compounds of the invention (Compounds F, H, and O, prepared as described in Examples 4, 5 and 6, respectively) was evaluated in male db/db mice. Met-FGF21 (Compound A) was included for comparison at three different dose levels, viz. 0.125, 0.5 and 1 mg/kg subcutaneously.

The compounds of the invention were tested at one dose level, viz. 0.5 mg/kg subcutaneously (approximately 24 nm/kg). Plasma levels of the comparative compound were followed for 6 hours, whereas plasma levels of the compounds of the invention were followed for 48 hours.

Plasma T½ was estimated to be 1.3-1.7 hours for the comparative compound (1.4 hours when dosed 0.5 mg/kg, like the test compounds), 8.2 hours for Compound F, 15.9 hours for Compound H, and 14.6 hours for Compound O.

Mini Pig

The pharmokinetic profile of Met-FGF21 (Compound A), and an FGF21 compound of the invention (Compound F, prepared as described in Example 4) were tested in normal male Gottingen mini pigs, n=3-4, (12-15 months old, 25 kg).

The plasma concentration of Compound A was monitored for one week, whereas the plasma concentration of Compound F was monitored for two weeks. Both compounds were dosed as a single intravenous dose of 0.1 mg/kg (approximately 5 nmol/kg).

The mean half-life (T½) of the comparative compound (Compound A) was 10.4 hours with a standard deviation of 3.1 hours, whereas the mean T½ of the compound of the invention (Compound F) was 91.9 hours, with a standard deviation of 17.1 hours.

The plasma levels of the FGF21 compounds were determined using Fibroblast Growth Factor-21 Human ELISA (available from BioVendor, catalogue no. RD191108200R).

These results strongly confirm the protracted effect of the FGF21 derivatives of the invention.

Example 12

Preparation of a Further Cys Derivative of an FGF21 Analogue

Preparation of the S71C Met-FGF21 derivative S-71-({2-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-ethylcarbamoyl}-methyl) [Cvs71] Met-FGF21 (Compound O)

The Cys residue at position 71 in the S71C Met-FGF21 analogue, prepared as generally described in Examples 2 and 3 (SEQ ID NO:1 with S71C and an N-terminal M), was modified at the thiol group with the following reagent:

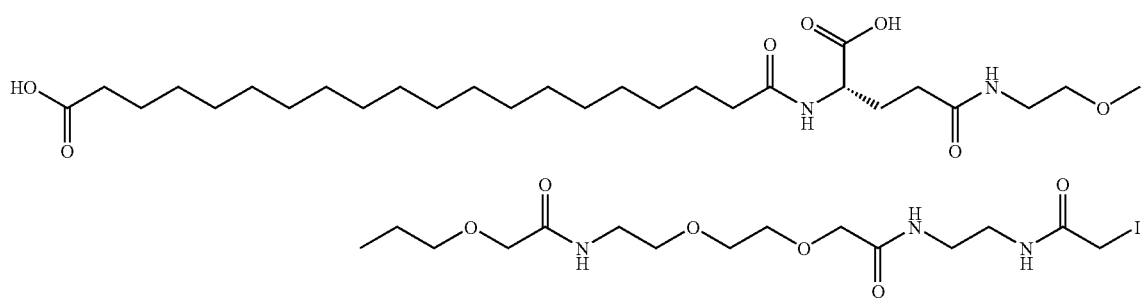

General Procedure B

[Cys71] Met-FGF21 (21.8 mg, 1.1 umol), freeze dried from NH4HCO3, was dissolved in 20 mM TRIS, 0.5 NaCl, pH 8.0 (4.36 ml). 19-{(S)-1-Carboxy-3-[2-(2-{[2-(2-{[2-(2-iodo-acetylamino)-ethylcarbamoyl]-methoxy}-ethoxy)-ethylcarbamoyl]-methoxy}-ethoxy)-ethyl-carbamoyl]-propylcarbamoyl}-nonadecanoic acid (5.4 mg, 5 eq), which was prepared as described above, was dissolved in 0.02M TRIS, 0.5M NaCl pH 8.0 buffer/acetonitrile 1:1 (1.09 ml) and added to the solution of [Cys71] Met-FGF21. After 2 h and 15 min the mixture was desalted on HiPrep 26/10 in A-buffer (1.5 CV). The pooled fractions was purified by anion exchange on a monoQ 5/50 GL column using A-buffer: 20 mM TRIS, pH 7.8; B-buffer: 20 mM TRIS, 50 mM NaCl, pH 7.8, flow 0.5 ml and a gradient from 0-100% B over 60CV. The isolated fractions containing product were pooled and buffer exchange to 50 mM NH4HCO3 was made using PD 10 (GE 179851-01) columns. The eluate was collected and filtered through a Millex GV sterile 0.22 um filter and freeze dried. Yield 6.7 mg.

LCMS1: Theoretical mass: 20400.2 Found: 20402.3

Example 13

Preparation of another Cys Derivative of an FGF21 Analogue

Preparation of the S71C Met-FGF21 derivative S-71-[1-(2-{2-[2-(2-{2-[2-(2-{2-[)S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-ethyl]-2,5-dioxo-pyrrolidin-3-yl] [Cvs71] Met-FGF21

The Cys residue at position 71 in the S71C Met-FGF21 analogue, prepared as generally described in Examples 2 and 3 (SEQ ID NO:1 with S71C and an N-terminal M), was modified at the thiol group at position 71 with the reagent prepared as described above:

The compound was prepared using the general procedure A from Example 5, without the size exclusion purification. Yield 2.88 mg.
LCMS1: Theoretical mass: 20483.3. Found: 20483.

Example 14

Preparation of a Further Cys Derivative of an FGF21 Analogue

Preparation of the S71 C Met-FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [Cys71] Met-FGF21

Preparation of 17-{(S)-1-carboxy-3-[2-(2-{[2-(2-{[2-(2-iodo-acetylamino)-ethylcarbamoyl]-methoxy}-ethoxy)-ethylcarbamoyl]-methoxy}-ethoxy)-ethylcarbamoyl]-propylcarbamoyl}-heptadecanoic acid Step 1: 17-[(S)-3-(2-{2-[(2-{2-[(2-Amino-ethylcarbamoyl)-methoxy]-ethoxy}-ethylcarbamoyl)-methoxy]-ethoxy}-ethylcarbamoyl)-1-carboxy-propylcarbamoyl]-heptadecanoic acid To a solution of ethanol (10 ml) and ethylenediamine (1 ml) was added 17-((S)-1-carboxy-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-heptadecanoic acid (500 mg). After stirring over night at room temperature, the mixture was concentrated in vacuo at 40° C. The residue was purified by preparative HPLC (10-65% acetonitrile, 0.1% TFA, 20 mL/min, C18, 30 mm×250 mm, 110 Å). Yield 332 mg (70%).
LCMS3: Theoretical mass: 776.0. Found: 776.6 (M+1).

Step2: 17-{(S)-1-Carboxy-3-[2-(2-{[2-(2-{[2-(2-iodo-acetylamino)-ethylcarbamoyl]-methoxy}-ethoxy)-ethylcarbamoyl]-methoxy}-ethoxy)-ethylcarbamoyl]-propylcarbamoyl}-heptadecanoic acid To a solution of iodoacetic acid (92 mg) in acetonitrile (1 ml) was added TSTU (142 mg) and DIPEA (0.085 ml). After stirring at RT for 60 min a solution of 17-[(S)-3-(2-{2-[(2-{2-[(2-Amino-ethylcarbamoyl)-methoxy]-ethoxy}-ethylcarbamoyl)-methoxy]-ethoxy}-ethylcarbamoyl)-1-carboxy-propylcarbamoyl]-heptadecanoic acid (0.320 g) in 0.1M Na2CO3 (12 ml). After stirring for 120 min, pH of the

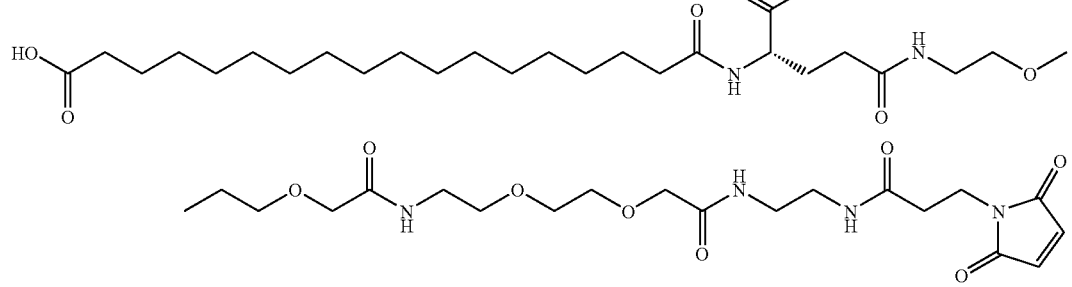

mixture was adjusted to 1 with 1N HCl. The precipitate was filtered off and washed with water and dried in vacuo. Yield 350 mg (90%).
LCMS3: Theoretical mass: 943.9 Found: 944.6 (M+1).

The Cys residue at position 71 in the S71C Met-FGF21 analogue, prepared as generally described in Examples 2 and 3 (SEQ ID NO:1 with S71C and an N-terminal M), was modified at the thiol group at position 71 with the reagent prepared as described above:

General Procedure B (NaCl)

The compound was prepared using the general procedure B from Example 12. The reaction was performed in a 1:1 mixture of 20 mM TRIS, 0.5 NaCl, pH 7.5 and DPBS-buffer. The size exclusion purification was excluded. Yield 19.5 mg mg (58%).

LCMS1: Theoretical mass: 20511 Found: 20511.

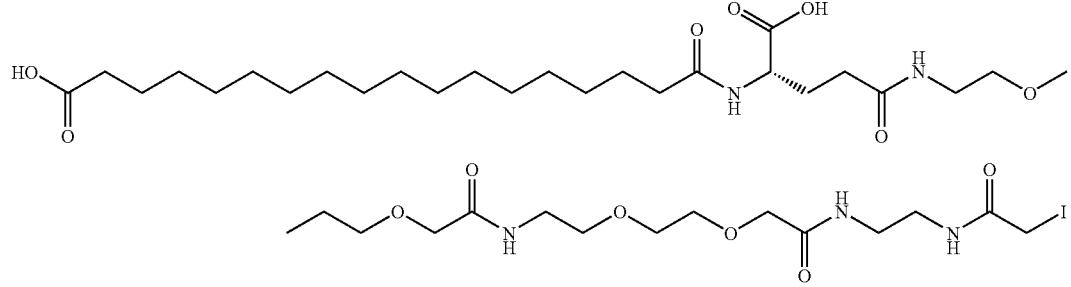

General Procedure B (NaCl)
The compound was prepared using the general procedure B from Example 12, at pH 7.5 and without the size exclusion purification. Yield 15.9 mg (38%).
LCMS1: Theoretical mass: 20372.19 Found: 20372.34.

Example 15

Preparation of a Further Cys Derivative of an FGF21 Analogue

Preparation of the (−1G, 71C, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4-(17-carboxy-heptadecanoy-lamino)-butyrylamino]-ethoxy}-ethoxy)-acety-lamino]-ethoxy}-ethoxy)-acetyl-amino]-ethylcarbamoyl}-methyl) [71C, 166F, 167G, 168L, 169aT, 171L, 172E, 173A, 174V, 179F, 180E, 181 K] Glv-FGF21

The Cys residue at position 71 in the (−1G, 71C, 166F, 167G, 168L, 169aT, 171L, 172E, 173A, 174V, 179F, 180E, 181K) FGF21 analogue, prepared as generally described in Examples 56 (SEQ ID NO:1), was modified at the thiol group at position 71 with the reagent prepared as described above:

Example 16

Preparation of a Further Cys Derivative of an FGF21 Analogue

Preparation of the (−1G, 71C, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-(17-carboxy-heptadecanoylamino)-butyrylamino]-ethoxy}-ethoxy)-acetylamino]-ethoxy}-ethoxy)-acetyl-amino]-ethylcarbamoyl}-methyl) [71 C, 121Q, 166F, 167G, 168L, 169aT, 171L, 172E, 173A, 174V, 179F, 180E, 181K] Gly-FGF21

General Procedure C:
The Cys residue at position 71 in the (−1G, 71C,121Q, 166F, 167G, 168L, 169aT, 171L, 172E, 173A, 174V, 179F, 180E, 181K) FGF21analogue, prepared as generally described in Examples 56 (SEQ ID NO: 1), was modified at the thiol group at position 71 with the reagent prepared as described above:

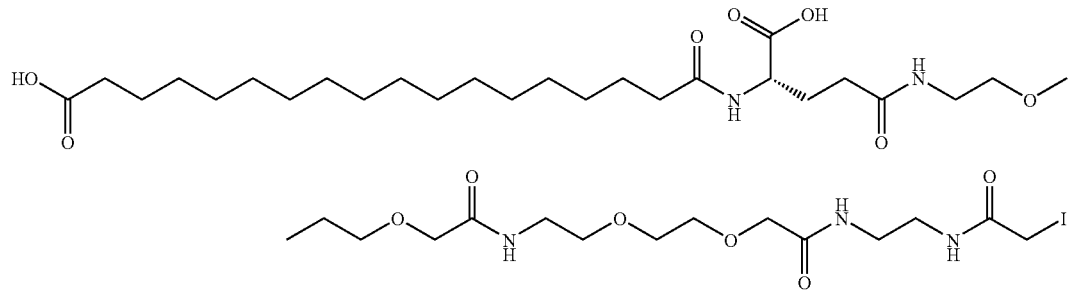

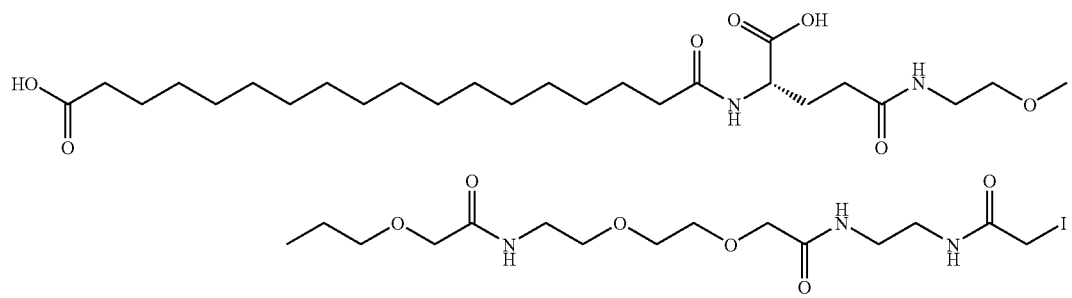

To (−1G, 71C, 121Q, 166F, 167G, 168L, 169aT, 171L, 172E, 173A, 174V, 179F, 180E, 181K) FGF21 (33.8 mg, 1.7 umol) in DPBS-buffer (2.7 mg/ml) was added TRIS (3 mg) and sodium chloride (29 mg). 17-{(S)-1-Carboxy-3-[2-(2-{[2-(2-{[2-(2-iodo-acetylamino)-ethyl-carbamoyl]-methoxy}-ethoxy)-ethylcarbamoyl]-methoxy}-ethoxy)-ethylcarbamoyl]-propyl-carbamoyl}-heptadecanoic acid (8 mg, 5 eq), which was prepared as described above, was dissolved in 0.02M TRIS, 0.5M NaCl pH 7.5 buffer (0.2 ml) and acetonitrile (0.3 ml) and added to the solution of (−1G, 71 C, 121 Q, 166F, 167G, 168L, 169aT, 171 L, 172E, 173A, 174V, 179F, 180E, 181 K) FGF21. After 5 h the mixture was filtered through a Millex GV sterile 0.22 um filter and desalted on two HiPrep 26/10 in a row in A-buffer (1.5 CV). The pooled fractions was purified by anion exchange on a Source 15Q 4,6/100 PE column using A-buffer: 20 mM TRIS, pH 7.5; B-buffer: 20 mM TRIS, 50 mM NaCl, pH 7.5, flow 2.5 ml and a gradient from 5-40% B over 40CV. The isolated fractions containing product were pooled and buffer exchange to DBPS-buffer on a HiPrep 26/10 column. The eluate was concentrated using Vivaspin 20 centrifugal filters (10000 MWCO), collected and filtered through a Millex GV sterile 0.22 um. Yield 10.9 mg (31%).
LCMS1: Theoretical mass: 20525. Found: 20525.

Example 17

Preparation of a Further Cys Derivative of an FGF21 Analogue

Preparation of the (−1A, 71C, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl-amino]-ethylcarbamoyl}-methyl) [71C, 121Q, 166F, 167G, 168L, 169aT, 171L, 172E, 173A, 174V, 179F, 180E, 181K] Ala-FGF21

The Cys residue at position 71 in the (−1A, 71C,121Q, 166F, 167G, 168L, 169aT, 171L, 172E, 173A, 174V, 179F, 180E, 181K) FGF21 analogue, prepared as generally described in Examples 56 (SEQ ID NO:1), was modified at the thiol group at position 71 with the reagent prepared as described above:

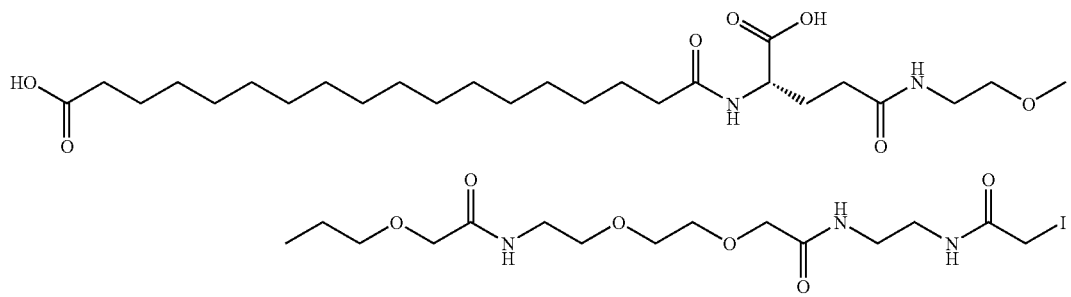

The compound was prepared using the general procedure C from Example 16. Yield 11.4 mg (33%).

LCMS1: Theoretical mass: 20539.4. Found: 20539.5.

Example 18

Preparation of a Further Cys Derivative of an FGF21 Analogue

Preparation of the (-1S, 71C, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl-amino]-ethylcarbamoyl}-methyl) [71C, 166F, 167G, 168L, 169aT, 171L, 172E, 173A, 174V, 179F, 180E, 181K] Ser-FGF21

The Cys residue at position 71 in the (-1S, 71C, 166F, 167G, 168L, 169aT, 171L, 172E, 173A, 174V, 179F, 180E, 181K) FGF21 analogue, prepared as generally described in Examples 56 (SEQ ID NO:1), was modified at the thiol group at position 71 with the reagent prepared as described above:

Example 19

Preparation of a Further N-Terminal Derivative of an FGF21 Analogue

Preparation of the (-5G, -4S, -3G, -2S, -1G, 56R, 59R, 69R, 102E, 121Q, 122R, 168L) FGF21 derivative N-alpha-3-[(17-carboxy-heptadecanoyl)-carboxymethyl-amino]-propionyl (-5G, -4S, -3G, -2S, -1G, 56R, 59R, 69R, 102E, 121Q, 122R, 168L) FGF21

Preparation of 17-{carboxymethyl-[2-(2,5-dioxo-pyrrolidin-1-yloxycarbonyl)-ethyl]-carbamoyl}-heptadecanoic acid 17-{tert-Butoxycarbonylmethyl-[2-(2,5-dioxo-pyrrolidin-1-yloxycarbonyl)-ethyl]-carbamoyl}-heptadecanoic acid tert-butyl ester (240 mg), prepared as described in WO2005/012347, was treated with 95% TFA for 1 h and concentrated in vacuo. The residue was co-concentrated with acetonitrile to give a white solid in a quantitative yield, 200 mg.

LCMS3: Theoretical mass: 540.7, Found: 541.3 (M+1).

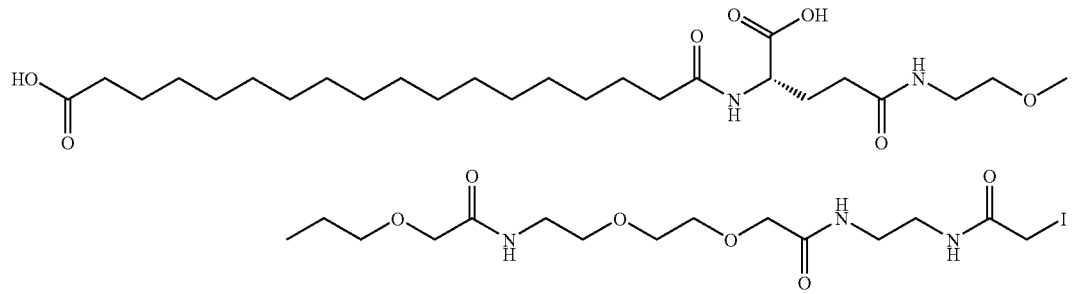

The compound was prepared using the general procedure C from Example 16, using a MonoQ 5/50 GI column for purification. Yield 20.9 mg (58%).

LCMS1: Theoretical mass: 20541, Found: 20541.

The N-teminal position in the (-5G, -4S, -3G, -2S, -1G, 56R, 59R, 69R, 102E, 121Q, 122R, 168L) FGF21 analogue, prepared as generally described in Examples 56 (SEQ ID NO:1), was modified with the reagent prepared as described above:

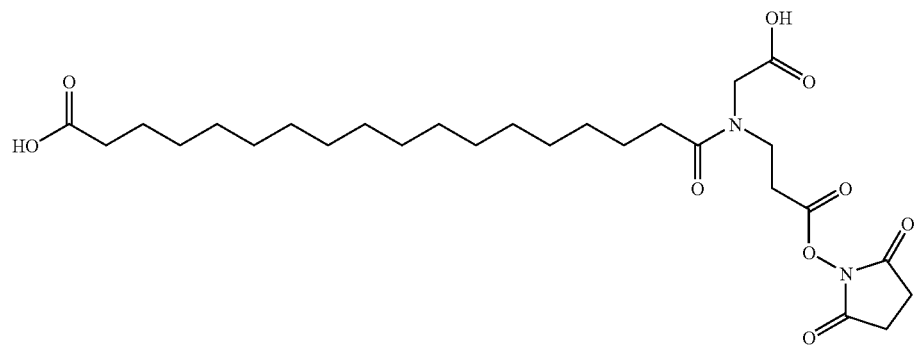 [SMILES: O=C(O)CCCCCCCCCCCCCCCCC(=O)N(CCC(=O)ON1C(=O)CCC1=O)CC(=O)O]

The compound was prepared using the procedure from Example 7, using a MonoQ 5/50 GI column for purification.
LCMS3: Theoretical mass: 20301.9, Found: 1451,2 (M+14).

The FGF21 derivatives of the invention in the following examples may be prepared similarly:

Example 20

Preparation of a Further Cys Derivative of an FGF21 Analogue

Preparation of the (−1G, 71C, 166F, 167G, 168L, 169aT, 171L, 172E, 173A, 174V, 179F, 180E, 181K) FGF21 derivative S-71-({2-[2-(2-{2-[2-(2-{2-[(S)-4-(19-carboxy-nonadecanoylamino)-butyrylamino]-ethoxy}-ethoxy)-acetylamino]-ethoxy}-ethoxy)-acetyl-amino]-ethylcarbamoyl}-methyl) [71C, 166F, 167G, 168L, 169aT, 171L, 172E, 173A, 174V, 179F, 180E, 181K] Gly-FGF21

Example 21

Preparation of a Further Cys Derivative of an FGF21 Analogue

Preparation of the (−1G, 71C, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-(19-carboxy-nonadecanoylamino)-butyrylamino]-ethoxy}ethoxy)-acetylamino]-ethoxy}-ethoxy)-acetyl-amino]-ethylcarbamoyl}-methyl) [71C, 121Q, 166F, 167G, 168L, 169aT, 171L, 172E, 173A, 174V, 179F, 180E, 181K] Gly-FGF21

Example 22

Preparation of a Further Cys Derivative of an FGF21 Analogue

Preparation of the (−1A, 71C, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetyl-amino]-ethylcarbamoyl}-methyl) [71C, 121Q, 166F, 167G, 168L, 169aT, 171L, 172E, 173A, 174V, 179F, 180E, 181 K] Ala-FGF21

Example 23

Preparation of a Further Cys Derivative of an FGF21 Analogue

Preparation of the (−1S, 71C, 166F, 167G, 168L, 169aT, 171L, 172E, 173A, 174V, 179F, 180E, 181K) FGF21 derivative S-71-({2-[2-(2-{2-[2-(2-{2-[(S)-4-(19-carboxy-nonadecanoylamino)-butyrylamino]-ethoxy}-ethoxy)-acetylamino]-ethoxy}-ethoxy)-acetyl-amino]-ethylcarbamoyl}-methyl) [71C, 166F, 167G, 168L, 169aT, 171L, 172E, 173A, 174V, 179F, 180E, 181K] Ser-FGF21

Example 24

Preparation of a Further Cys Derivative of an FGF21 Analogue

Preparation of the (−1G, 71C, 102E, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4(19-carboxy-nonadecanoylamino)-butyrylamino]-ethoxy}-ethoxy)-acetylamino]-ethoxy}-ethoxy)-acetylamino]-ethylcarbamoyl}-methyl) [71C, 102E, 121Q, 166F, 167G, 168L, 169aT, 171L, 172E, 173A, 174V, 179F, 180E, 181K] Gly-FGF21

Example 25

Preparation of a Further Cys Derivative of an FGF21 Analogue

Preparation of the (−1G, 71C, 102E, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [71C, 102E, 121Q, 166F, 167G, 168L, 169aT, 171L, 172E, 173A, 174V, 179F, 180E, 181K] Gly-FGF21

Example 26

Preparation of a Further Cys Derivative of an FGF21 Analogue

Preparation of the (−1A, 71C, 102E, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-ethylcarbamoyl}-methyl) [71C, 102E, 121Q, 166F, 167G, 168L, 169aT, 171L, 172E, 173A, 174V, 179F, 180E, 181 K] Ala-FGF21

The following example was prepared

Example 27

Preparation of a Further Cys Derivative of an FGF21 Analogue

Preparation of the (−1A, 71C, 102E, 121Q, 166F, 167G, 168L, 169aT, 171L, 172E, 173A, 174V, 179F, 180E, 181K) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [71C, 102E, 121Q, 166F, 167G, 168L, 169aT, 171L, 172E, 173A, 174V, 179F, 180E, 181 K] Ala-FGF21

The Cys residue at position 71 in the (−1A, 71C, 102E, 121Q, 166F, 167G, 168L, 169aT, 171L, 172E, 173A, 174V, 179F, 180E, 181K) FGF21analogue, prepared as generally described in Examples 56 (SEQ ID NO:1), was modified at the thiol group at position 71 with the reagent prepared as described above:

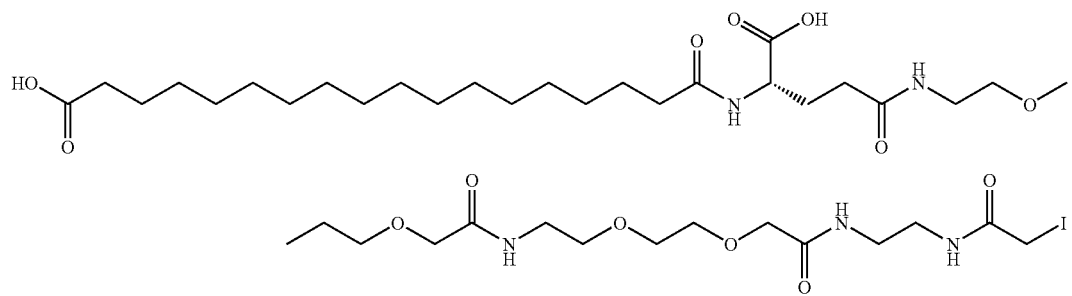

The compound was prepared using the general procedure C from Example 16, using a MonoQ 5/50 GI column for purification with the exception of the buffers, to wich 5% ethanol was added. Yield 18.2 mg (43%).
LCMS1: Theoretical mass: 20553.39, Found: 20552.88.

The FGF21 derivatives of the invention in the following examples may be prepared similarly:

Example 28

Preparation of a Further Cys Derivative of an FGF21 Analogue

Preparation of the (−1A, 71C, 121Q, 166F, 167G, 168L, 169aT, 171L, 172E, 173A, 174V, 179F, 180E, 181K, 182G) FGF21 derivative S-71-({2-[2-(2-{2-[2-(2-{2-[(S)-4carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [71C, 121Q, 166F, 167G, 168L, 169aT, 171L, 172E, 173A, 174V, 179F, 180E, 181K, 182G] Gly-FGF21

The following examples were prepared

Example 29

Preparation of a Further Cys Derivative of an FGF21 Analogue

Preparation of the (−1A, 71C, 121Q, 166F, 167G, 168L, 169aT, 171L, 172E, 173A, 174V, 179F, 180E) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl-amino]-ethylcarbamoyl}-methyl) [71C, 121Q, 166F, 167G, 168L, 169aT, 171L, 172E, 173A, 174V, 179F, 180E]Ala-FGF21

The Cys residue at position 71 in the (−1A, 71C, 121Q, 166F, 167G, 168L, 169aT, 171L, 172E, 173A, 174V, 179F, 180E) FGF21 analogue, prepared as generally described in Examples 56 (SEQ ID NO:1), was modified at the thiol group at position 71 with the reagent prepared as described above:

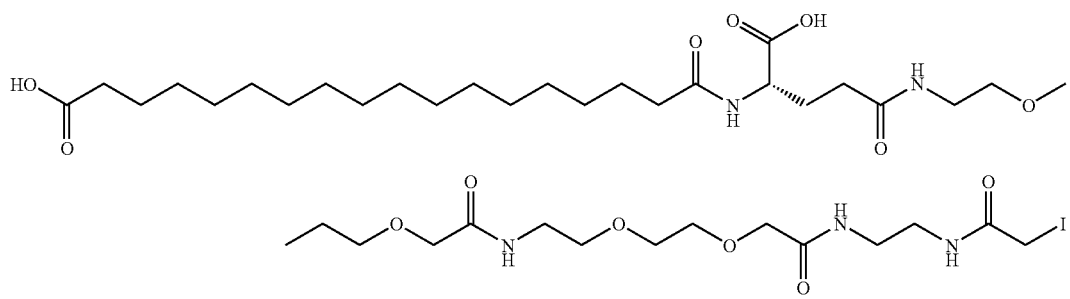

The compound was prepared using the general procedure C from Example 16, using a MonoQ 4,6/100 PE column for purification with the exception of the buffers, to wich 5% ethanol was added. Yield 19.8 mg (46%).
LCMS1: Theoretical mass: 20498.40 Found: 20498.07

Example 30

Preparation of a Further Cys Derivative of an FGF21 Analogue

Preparation of the (−1A, 71C, 121Q, 166F, 167G, 168L, 169aT, 171L, 172E, 173A, 174V, 179F, 180E, des181) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [71C, 121Q, 166F, 167G, 168L, 169aT, 171L, 172E, 173A, 174V, 179F, 180E, des181K] Ala-FGF21

The Cys residue at position 71 in the (−1A, 71C, 121Q, 166F, 167G, 168L, 169aT, 171L, 172E, 173A, 174V, 179F, 180E, des181) FGF21analogue, prepared as generally described in Examples 56 (SEQ ID NO:1), was modified at the thiol group at position 71 with the reagent prepared as described above:

Example 32

Preparation of a Further Cys Derivative of an FGF21 Analogue

Preparation of the (−1A, 28R, 56R, 59R, 69R, S71C, 102T, 121Q, 122R, 166F, 167G, 168L, 170T) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [28R, 56R, 59R, 69R, S71C, 102T, 121Q, 122R, 166F, 167G, 168L, 170T] Ala-FGF21

Example 33

Preparation of a Further Cys Derivative of an FGF21 Analogue

Preparation of the (−1G, 71C, 166F, 167G, 168L, 169aT, 171L, 172E, 173A, 174V, 179F, 180E, 181K) FGF21 derivative S-71-[(2-{3-[(17-carboxy-heptadecanoyl)-carboxymethyl-amino]-propionylamino}-ethylcarbamoyl)-methyl] [71 C, 166F, 167G, 168L, 169aT, 171 L, 172E, 173A, 174V, 179F, 180E, 181K]Gly-FGF21

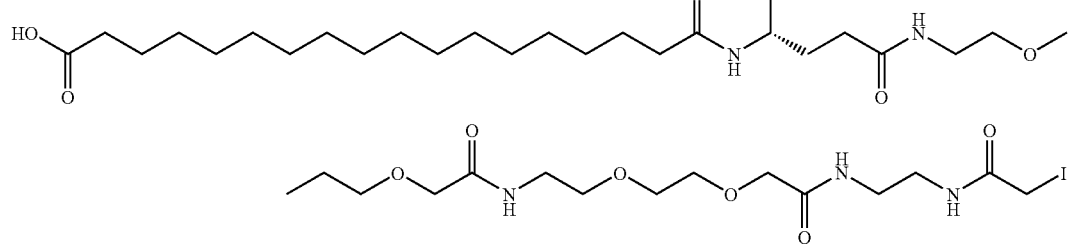

The compound was prepared using the general procedure C from Example 16, using a MonoQ 4,6/100 PE column for purification with the exception of the buffers, to wich 5% ethanol was added. Yield 11.3 mg (40%).
LCMS1: Theoretical mass: 20411.32, Found: 20410.90
The FGF21 derivatives of the invention in the following examples may be prepared similarly:

Example 31

Preparation of a Further Cys Derivative of an FGF21 Analogue

Preparation of the (−1A, 71C, 121Q, 143V, 145E, 146E, 148aD, 149L, 150R, 152H, 153aE, 153bS, 153cD, 153dM, 154F, 155S, 156S, 158L, 159E, 160T, 161D, 163M, 166F, 167G, 168L, 169aT, 171L, 172E, 173A, 174V, 179F, 180E) FGF21 derivative S-71-({2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-ethylcarbamoyl}-methyl) [71 C, N 121 Q, 143V, 145E, 146E, 148aD, 149L, 150R, 152H, 153aE, 153bS, 153cD, 153dM, 154F, 155S, 156S, 158L, 159E, 160T, 161D, 163M, 166F, 167G, 168L, 169aT, 171L, 172E, 173A, 179F, 180E] Ala-FGF21

Preparation of 17-(carboxymethyl-{2-[2-(2-iodo-acetylamino)-ethylcarbamoyl]-ethyl}-carbamoyl)-heptadecanoic acid Step 1: 17-{[2-(2-Amino-ethylcarbamoyl)-ethyl]-carboxymethyl-carbamoyl}-heptadecanoic acid To a solution of ethylene diamine (0.3 ml) in THF (4 ml) was added a solution of 17-{carboxymethyl-[2-(2,5-dioxo-pyrrolidin-1-yloxycarbonyl)-ethyl]-carbamoyl}-heptadecanoic acid (190 mg), prepared as described in Example 19. The mixture was stirred over night at room temperature and purified directly by preparative HPLC using 0.1% TFA in water and 0.1% TFA in acetonitrile as eluents. Fractions containing the product were pooled and lyophilized. Yield 60 mg (35%).
LCMS3: Theoretical mass: 485.67, Found: 486.38 (M+1).

Step 2: 17-(Carboxymethyl-{2-[2-(2-iodo-acetylamino)-ethylcarbamoyl]-ethyl}-carbamoyl)-heptadecanoic acid To a solution of iodoacetamide (35 mg) in acetonitrile (0.50 ml) was added TSTU (56 mg) and DIPEA (0.032 ml). The mixture was stirred for 1 h before a solution of 17-{[2-(2-amino-ethylcarbamoyl)-ethyl]-carboxymethyl-car bamoyl}-heptadecanoic acid (60 mg) in 0.1 M Na2CO3 (5 ml) was added. The mixture was stirred for 2 h and acidified to pH 1 with 1N HCl. The mixture was spinned down. The supernatant was decanted off and the precipitate was washed with water twice and dried in vacuo. Yield 75 mg (93%) LCMS3: Theoretical mass: 653.60, Found: 654.27 (M+1).

The Cys residue at position 71 in the (−1G, 71C, 166F, 167G, 168L, 169aT, 171L, 172E, 173A, 174V, 179F, 180E, 181K) FGF21 analogue, prepared as generally described in Example 56 can be modified at the thiol group at position 71 with the reagent prepared as described above using the general procedure A, B or C.

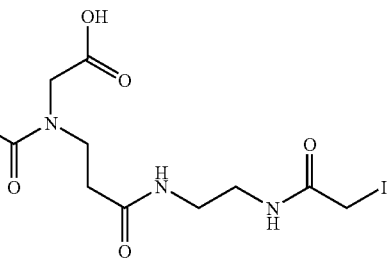

Example 34

Preparation of a Further Cys Derivative of an FGF21 Analogue

Preparation of the (−1G, 71C, 121Q, 166F, 167G, 168L, 169aT, 171L, 172E, 173A, 174V, 179F, 180E, 181K) FGF21 derivative S-71-[(2-{3-[(17-carboxy-heptadecanoyl)-carboxymethyl-amino]-propionylamino}-ethylcarbamoyl)-methyl] [71 C, 121 Q, 166F, 167G, 168L, 169aT, 171L, 172E, 173A, 174V, 179F, 180E, 181K] Gly-FGF21

The following example was prepared

Example 35

Preparation of a Further Cys Derivative of an FGF21 Analogue

Preparation of the (−1k 71C, 121Q, 166F, 167G, 168L, 169aT, 171L, 172E, 173A, 174V, 179F, 180E, 181K) FGF21 derivative S-71-[(2-{3-[(17-carboxy-heptadecanoyl)-carboxy-methyl-amino]-propionylamino}-ethylcarbamoyl)-methyl] [71 C, 121 Q, 166F, 167G, 168L, 169aT, 171L, 172E, 173A, 174V, 179F, 180E, 181K]Ala-FGF21

The Cys residue at position 71 in the (−1A, 71C,121Q, 166F, 167G, 168L, 169aT, 171L, 172E, 173A, 174V, 179F, 180E, 181K) FGF21analogue, prepared as generally described in Examples 56 (SEQ ID NO:1), was modified at the thiol group at position 71 with the reagent prepared as described above:

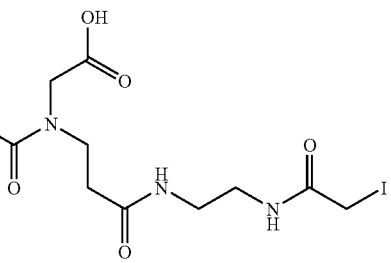

The compound was prepared using the procedure from Example 16. Yield 9.3 mg (33%).

LCMS1: Theoretical mass: 20249.05 Found: 20249.58.

The FGF21 derivatives of the invention in the following examples may be prepared similarly

Example 36

Preparation of a Further Cys Derivative of an FGF21 Analogue

Preparation of the (−1S, 71C, 166F, 167G, 168L, 169aT, 171L, 172E, 173A, 174V, 179F, 180E, 181K) FGF21 derivative S-71-[(2-{3-[(17-carboxy-heptadecanoyl)-carboxymethyl-amino]-propionylamino}-ethylcarbamoyl)-methyl] [71 C, 166F, 167G, 168L, 169aT, 171 L, 172E, 173A, 174V, 179F, 180E, 181K] Ser-FGF21

Example 37

Preparation of a Further Cys Derivative of an FGF21 Analogue

Preparation of the (−1G, 71C, 102E, 121Q, 166F, 167G, 168L, 169aT, 171L, 172E, 173A, 174V, 179F, 180E, 181K) FGF21 derivative S-71-[(2-{3-[(17-Carboxy-heptadecanoyl)-carboxymethyl-amino]-propionylamino}-ethylcarbamoyl)-methyl] [71 C, 102E, 121 Q, 166F, 167G, 168L, 169aT, 171L, 172E, 173A, 174V, 179F, 180E, 181K] Gly-FGF21

Example 38

Further Derivatisation of FGF21 Compounds at the N-Terminus with Albumin Binders Preparation of the (Q28R, K56R, K59R, K69R, D102T, N121Q, K122R, L166F, S167G, M168 L, G170T) Ala-FGF21 derivative N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Q28R, K56R, K59R, K69R, D102T, N121Q, K122R, L166F, S167G, M168L, G170T] Ala-FGF21

The N-terminal Met residue in the (Q28R, K56R, K59R, K69R, D102T, N121Q, K122R, L166F, S167G, M168L, G170T) Ala-FGF21 analogue, prepared as generally described in Example 56 (SEQ ID NO:1 with Q28R, K56R, K59R, K69R, D102T, N121Q, K122R, L166F, S167G, M168L, G170T) FGF21 and an N-terminal Ala), could be modified at the alpha amino group as described in example 7.

Example 39

Preparation of a Further Cys Derivative of an FGF21 Analogue

Preparation of the (−1A, 71C, 102E, 121Q, 166F, 167G, 168L, 169aT, 171L, 172E, 173A, 174V, 179F, 180E, 181K) FGF21 derivative S-71-[2-{3-[(17-carboxy-heptadecanoyl)-carboxymethyl-amino]-propionylamino}-ethylcarbamoyl)-methyl] [71C, 102E, 121Q, 166F, 167G, 168L, 169aT, 171L, 172E, 173A, 174V, 179F, 180E, 181 K] Ala-FGF21

Example 40

Preparation of a Further Cys Derivative of an FGF21 Analogue

Preparation of the (−1A, 71C, 121Q, 166F, 167G, 168L, 169aT, 171L, 172E, 173A, 174V, 179F, 180E, 181K) FGF21 derivative S-71-[2-{3-[(17-carboxy-heptadecanoyl)-carboxy-methyl-amino]-propionylamino}-ethylcarbamoyl)-methyl] [71 C, 121 Q, 166F, 167G, 168L, 169aT, 171L, 172E, 173A, 174V, 179F, 180E, 181K] Ala-FGF21

Example 41

Preparation of a Further Cys Derivative of an FGF21 Analogue

Preparation of the −1A, 71C, 121Q, 166F, 167G, 168L, 169aT, 171L, 172E, 173A, 174V, 179F, 180E, 181K, 182G-FGF21 derivative S-71-[(2-{3-[(17-carboxy-heptadecanoyl)-carboxymethyl-amino]-propionylamino}-ethylcarbamoyl)-methyl] [71 C, 121 Q, 166F, 167G, 168L, 169aT, 171L, 172E, 173A, 174V, 179F, 180E, 181K, 182G] Ala-FGF21

Example 42

Preparation of a Further Cys Derivative of an FGF21 Analogue

Preparation of the (−1A, 71C, 121Q, 166F, 167G, 168L, 169aT, 171L, 172E, 173A, 174V, 179F, 180E) FGF21 derivative S-71-[([(2-{3-[(17-carboxy-heptadecanoyl)-carboxymethyl-amino]-propionylamino}-ethylcarbamoyl)-methyl] [71C, 121Q, 166F, 167G, 168L, 169aT, 171L, 172E, 173A, 174V, 179F, 180E], Ala-FGF21

Example 43

Preparation of a Further Cys Derivative of an FGF21 Analogue

Preparation of the (−1A, 71C, 121Q, 166F, 167G, 168L, 169aT, 171L, 172E, 173A, 174V, 179F, 180E, des181K) FGF21 derivative S-71-[(2-{3-[(17-carboxy-heptadecanoyl)-carboxy-methyl-amino]-propionylamino}-ethylcarbamoyl)-methyl] [71 C, 121 Q, 166F, 167G, 168L, 169aT, 171L, 172E, 173A, 174V, 179F, 180E, des 181K] Ala-FGF21

Example 44

Preparation of a Further Cys Derivative of an FGF21 Analogue

Preparation of the (−1A, 71C, 121Q, 143V, 145E, 146E, 148aD, 149L, 150R, 152H, 153aE, 153bS, 153cD, 153dM, 154F, 155S, 156S, 158L, 159E, 160T, 161D, 163M, 166F, 167G, 168L, 169aT, 171L, 172E, 173A, 174V, 179F, 180E) FGF21 derivative S-71-[(2-{3-[(17-carboxy-heptadecanoyl)-carboxymethyl-amino]-propionylamino}-ethylcarbamoyl)-methyl] [71C, 121Q, 143V, 145E, 146E, 148aD, 149L, 150R, 152H, 153aE, 153bS, 153cD, 153dM, 154F, 155S, 156S, 158L, 159E, 160T, 161D, 163M, 166F, 167G, 168L, 169aT, 171L, 172E, 173A, 174V, 179F, 180E] Ala-FGF21

Example 45

Preparation of a Further Cys Derivative of an FGF21 Analogue

Preparation of the (−1A, 28R, 56R, 59R, 69R, S71C, 102T, 121Q, 122R, 166F, 167G, 168L, 170T) FGF21 derivative S-71-[(2-{3-[(17-carboxy-heptadecanoyl)-carboxymethyl-amino]-propionylamino}-ethylcarbamoyl)-methyl] [28R, 56R, 59R, 69R, S71C, 102T, 121Q, 122R, 166F, 167G, 168L, 170T] Ala-FGF21

Example 46

Derivatisation of FGF21 Compounds at the N-Terminus with Albumin Binders

Preparation of the (K56R, K59R, K69R, K122R) Gly-FGF21 derivative N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [K56R, K59R, K69R, K122R] Gly-FGF21

The FGF-21 derivative was prepared and purified in similar fashion as described in Example 7.
LCMS1: Theoretical mass: 20293.9 Found: 20294.2

Example 47

Derivatisation of FGF21 Compounds at the N-Terminus with Albumin Binders

Preparation of the (28R, K56R, 59R, 69R, 102T, 121Q, 122R, 168L, 179F, 180E, 181) Gly-FGF21 derivative N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [28R, K56R, 59R, 69R, 102T, 121Q, 122R, 168L, 179F, 180E, 181R] Gly-FGF21

The FGF-21 derivative was prepared and purified in similar fashion as described in Example 7.
LCMS1: Theoretical mass: 20415.1 Found: 20415.3

Example 48

Derivatisation of FGF21 Compounds at the N-Terminus with Albumin Binders

Preparation of the (K56R, 59R, 69R, 122R, 168L) Gly-FGF21 derivative N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [K56R, 59R, 69R, 122R, 168] Gly-FGF21

The FGF-21 derivative was prepared and purified in similar fashion as described in Example 7.
LCMS1: Theoretical mass: 20275.9 Found: 20276.1

Example 49

Derivatisation of FGF21 Compounds at the N-Terminus with Albumin Binders

Preparation of the (K56R, 59R, 69R, 122R, 166F, 167G, 168L, 169aT, 171L, 172E, 173A, 174V, 179F, 180E, 181R) Gly-FGF21 derivative N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [K56R, 59R, 69R, 122R, 166F, 167G, 168L, 169aT, 171L, 172E, 173A, 174V, 179F, 180E, 181R] Gly-FGF21

The FGF-21 derivative was prepared and purified in similar fashion as described in Example 7.
LCMS1: Theoretical mass: 20535.2 Found: 20535.6

Example 50

Derivatisation of FGF21 Compounds at the N-Terminus with Albumin Binders

Preparation of the (K56R, 59R, 69R, 122R, 166F, 167G, 168L, 169aT, 171L, 172E, 173A, 174V, 179F, 180E, 181R) Ser-FGF21 derivative N-alpha-1-[2-(2-{2-[2-(2-{2-[(S)-4carboxy-4-(17-carboxy-heptadecanoylamino)-butyrylamino]-ethoxy}-ethoxy)-acetylamino]-ethoxy}-ethoxy)-acetyl] [K56R, 59R, 69R, 122R, 166F, 167G, 168L, 169aT, 171L, 172E, 173A, 174V, 179F, 180E, 181R] Gly-FGF21

The FGF-21 derivative was prepared and purified in similar fashion as described in Example 7.
LCMS1: Theoretical mass: 20565.2 Found: 20565.5

Example 51

Derivatisation of FGF21 Compounds at the N-Terminus with Albumin Binders

Preparation of the (−14E, −13E, −12A, −11E, −10A, −9G, −8G, −7A, −6G, −5G, −4S, −3G, −2G, −1S, K56R, 59R, 69R, 122R) FGF21 derivative N-alpha-1-[(S)-4-carboxy-4-(17-carboxy-heptadecanoylamino)-butyryl] [−14E, −13E, −12A, −11E, −10A, −9G, −8G, −7A, −6G, −5G, −4S, −3G, −2G,−1S, K56R, 59R, 69R, 122R] FGF21

The FGF-21 derivative was prepared and purified in similar fashion as described in Example 7.
LCMS1: Theoretical mass: 21063.6 Found: 21063.8

Example 52

Derivatisation of FGF21 Compounds at the N-Terminus with Albumin Binders

Preparation of the (−5G, −4S, −3G, −2S, −1G, K56R, 59R, 69R, 102E, 121Q, 122R, 168L) FGF21 derivative N-alpha-1-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [−5G, −4S, −3G, −2S, −1G, K56R, 59R, 69R, 102E, 121Q, 122R, 168L] FGF21

The FGF-21 derivative was prepared and purified in similar fashion as described in Example 7.
LCMS1: Theoretical mass: 20592.2 Found: 20592.9

Example 53

Derivatisation of FGF21 Compounds at the N-Terminus with Albumin Binders

Preparation of the (K56R, K59R, K69R, K122R) Gly-FGF21 derivative N-alpha-1-(2-{2-[2-(16-1H-tetrazol-5-yl-hexadecanoylamino)-ethoxy]-ethoxy}-acetyl) [K56R, K59R, K69R, K122R] Gly-FGF21

10 mg (511 nmol) of (K56R, K59R, K69R, K122R) Gly-FGF21 in 1.72 ml buffer was buffer-changed with a 4 NAP-5-Column to DPBS-buffer. Protein concentration was determined to be 2.5 mg/ml. To the solution was added 400 µl 20% HPβCD (Hydroxypropyl Beta Cyclodextrin) and 400 µl 10% N-Acetyl-L-Methionine, pH 7.5. To this solution was added 8 eq (0,004086 mmol) active succinimidyl ester of {2-[2-(16-1H-tetrazol-5-yl-hexadecanoylamino)-ethoxy]-ethoxy}-acetic acid in 200 µl NMP at 7° C. The succinimidyl ester was generated with N,N-disuccinimidyl carbonate (CAS 74124-79-1) 1:1 for 20 min. After 90 min., 4 ml cooled 0.2M NaOH was added and the reaction was standing at 4° C. for 30 min. Then 4 ml 0.2M HCl was added and the pH was adjusted to 7.3.

The reaction mixture was filtered through a 0.22 um filter and was purified by ion exchange chromatography and lyophilized as described in Example 4.
LCMS1: Theoretical mass: 20029.66 Found: 20029.82.

Example 54

Derivatisation of FGF21 Compounds at the N-Terminus with Albumin Binders

Preparation of the (K56R, K59R, K69R, K122R) Gly-FGF21 derivative N-alpha1-[4-(16-1H-tetrazol-5-yl-hexadecanoylsulfamoyl)-butyryl] [K56R, K59R, K69R, K122R] Gly-FGF21

The succinimidyl ester of 4-(16-1H-tetrazol-5-yl-hexadecanoylsulfamoyl)-butyric acid was generated by dissolving 139 mg of 4-(16-1H-tetrazol-5-yl-hexadecanoylsulfamoyl)-butyric acid and 115 mg N-hydroxy succinimide in 1 ml DMF(warmed under hot water for a few sec). 145 mg (3-dimethylaminopropyl) ethyl carbodiimide hydrochloride was added and the mixture stirred for 20 min at room temperature. After 3.5 h the mixture was poured into 8 ml water and centrifuged. The supernatant was removed, and the suspension and centrifugation were repeated 2 times.

10 mg (K56R, K59R, K69R, K122R) Gly-FGF21 in 1.72 ml DPBS was buffer changed to DPBS, 4 ml after elution. 400 µl 10% N-acetylmethionine (pH ajusted to approx 8) and 400 µl 20% cyclodextrin were added. 200 µl of a solution of 330 µg 4-(16-(tetrazo-5-yl)hexadecanoylsulfamoyl) butyric acid succinimidyl ester in 1400 ul NMP was added. The reaction mixture was standing at 7° C. over night. 4 ml 0.2 M NaOH was added to the reaction mixture at 4° C. After 30 min the mixture was neutralized with 3.9 ml 0.2 M HCl.

The solution mixture was filtered through a 0.22 um filter and was purified by ion exchange chromatography and lyophilized as described in Example 4.
LCMS1: Theoretical mass: 20033.67 Found: 20033.72.

Example 55

Derivatisation of FGF21 Compounds at the N-Terminus with Albumin Binders

Preparation of the (−5G, −4S, −3G, −2S, −1G, K56R, 59R, 69R, 102E, 121Q, 122R, 168L) FGF21 derivative N-alpha-1-[4-(16-1H-tetrazol-5-yl-hexadecanoylsulfamoyl)-butyryl] [−5G, −4S, −3G, −2S, −1G, K56R, 59R, 69R, 102E, 121Q, 122R,168L] FGF21

The FGF-21 derivative was prepared and purified in similar fashion as described in Example 54.
LCMS1: Theoretical mass: 20331.94 Found: 20332.39

Example 56

Cloning and Expression of FGF21 Analogues

The following compounds were prepared and purified as described in example 2 and 3:
56a) (K56R, K59R, K69R, K122R) Gly-FGF21;
56b) (K56R, K59R, K69R, K122R, M168L) Gly-FGF21;
56c) (Q28R, K56R, K59R, K69R, D102T, N121Q, K122R, M168L, Y179F, A180E, S181R) Gly-FGF21;
56d) (K56R, K59R, K69R, D102E, N121Q, K122R, M168L) GSGSG-FGF21;
56e) (S71C, L166F, S167G, M168L, 169aT, P171L, S172E, Q173A, G174V, Y179F, A180E, S181K) Gly-FGF21;
56f) (K56R, K59R, K69R, K122R, L166F, S167G, M168L, 169aT, P171L, S172E, Q173A, G174V, Y179F, A180E, S181R) Ser-FGF21;
56g) (K56R, K59R, K69R, K122R, L166F, S167G, M168L, 169aT, P171L, S172E, Q173A, G174V, Y179F, A180E, S181R) Gly-FGF21;
56h) (K56R, K59R, K69R, K122R) EEAE-AGGAGGSGGS-FGF21;
56i) (S71C, L166F, S167G, M168L, 169aT, P171L, S172E, Q173A, G174V, Y179F, A180E, S181K) Ser-FGF21;
56j) (S71C, N121Q, L166F, S167G, M168L, 169aT, P171L, S172E, Q173A, G174V, Y179F, A180E, S181K) Gly-FGF21;
56k) (S71C, D102E, N121Q, L166F, S167G, M168L, 169aT, P171L, S172E, Q173A, G174V, Y179F, A180E, S181K) Gly-FGF21;
56l) (S71C, N121Q, L166F, S167G, M168L, 169aT, P171L, S172E, Q173A, G174V, Y179F, A180E, S181K) Ala-FGF21;

56m) (S71C, D102E, N121Q, L166F, S167G, M168L, 169aT, P171L, S172E, Q173A, G174V, Y179F, A180E, S181K) Ala-FGF21;
56n) (Q28R, K56R, K59R, K69R, D102T, N121Q, K122R, L166F, S167G, M168L, G170T) Ala-FGF21;
56o) (S71C, N121Q, L166F, S167G, M168L, 169aT, P171L, S172E, Q173A, G174V, Y179F, A180E) Ala-FGF21;
56p) (S71C, N121Q, L166F, S167G, M168L, 169aT, P171L, S172E, Q173A, G174V, Y179F, A180E, S181G) Ala-FGF21;
56q) (S71C, N121Q, L166F, S167G, M168L, 169aT, P171L, S172E, Q173A, G174V, Y179F, A180E, des S181) Ala-FGF21;
56r) (D102N) Met-FGF21;
56s) (Q15F) Met-FGF21;
56t) (D24K) Met-FGF21;
56u) (V16K) Met-FGF21;
56v) (S71C, M168I) Gly-FGF21;
56x) (S71C, M168L) Gly-FGF21;
56y) (K56R, K59R, K69R, K122R) FGF21;
56z) (N121Q) Met-FGF21;
56aa) (des N121) Met-FGF21;
56ab) (S71C) Gly-FGF21;
56ac) (P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, S181K) Met-FGF21;
56ad) (145aP, 145bM, L146V, P149E, G151E, I152D, A154R, P155G, Q156H, P157L, P158E, D159S, V160D, G161M, S162F, D164S, S167E, M168T, V169D, G170S, P171M, S172D, Q173P, G174V, R175G, S176L, P177V, S178T, Y179G, A180L, S181E, 182A, 183V, 184R, 185S, 186P, 187S, 188F, 189E, 190K) Met-FGF21;
56ae) (Q27E, K56R, K59R, K69R, D102T, N121Q, K122R, Y179F, A180E, S181R) Gly-FGF21;
56af) (Q15F, K56R, K59R, K69R, D102T, N121Q, K122R, Y179F, A180E, S181R) Gly-FGF21;
56ag) (S71C, L166F, S167G, M168L, 169aT, P171L, S172E, Q173A, G174V, Y179F, A180E, S181K) Gly-FGF21;
56ah) (L166F, S167G, M168L, 169aT, P171L, S172E, Q173A, G174V, Y179F, A180E, S181K) Ser-FGF21;
56ai) (M168A) Met-FGF21;
56aj) (M168S) Met-FGF21;
56ak) (K56R, K59R, K69R, K122R, L166F, S167G, M168L, 169aT, P171L, S172E, Q173A, G174V, A180E, S181R) FGF21;
56al) (M168S) Ser-FGF21;
56am) (Q28R, K56R, K59R, K69R, D102T, N121Q, K122R, D159E, M168L, G174A, Y179F) Gly-FGF21;
56an) (K56R, K59R, K69R, K122R) EESAAS-GAAAGSAAA-FGF21;
56ao) (Q28R, K56R, K59R, K69R, D102T, N121Q, L166F, S167G, M168L, G170T) Gly-FGF21;
56ap) (K56R, K59R, K69R, N121Q, K122R, L166F, S167G, M168L, 169aT, P171L, S172E, Q173A, G174V, Y179F, A180E, S181R) FGF21;
56aq) (K56R, K59R, K69R, N121Q, K122R, L166F, S167G, M168L, 169aT, P171L, S172E, Q173A, G174V, Y179F, A180E, desS181) FGF21;
56ar) (N121D) Met-FGF21; and
56as) (A26E, K56R, K59R, K69R, D102T, N121Q, K122R, Y179F, A180E, S181R) Gly-FGF21.

Example 57

Cloning and Expression of FGF21 Analogues

The following FGF21 derivative may be prepared similarly as described in examples 2 and 3:
57a) (Q28R, K56R, K59R, K69R, S71C, D102T, N121Q, K122R, L166F, S167G, M168L, G170T) Ala-FGF21;
57b) (K56R, K59R, K69R, N121Q, K122R) Gly-FGF21;
57c) (K56R, K59R, K69R, N121Q, K122R) Ala-FGF21;
57d) (K56R, K59R, K69R, N121Q, K122R) Ser-FGF21;
57e) (K56R, K59R, K69R, N121Q, K122R) FGF21;
57f) (K56R, K59R, K69R, N121Q, K122R, L166F, S167G, M168L, G170T) Gly-FGF21;
57g) (K56R, K59R, K69R, N121Q, K122R, L166F, S167G, M168L, G170T) Ala-FGF21;
57h) (K56R, K59R, K69R, N121Q, K122R, L166F, S167G, M168L, G170T) Ser-FGF21;
57i) (K56R, K59R, K69R, N121Q, K122R, L166F, S167G, M168L, G170T) FGF21;
57j) P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21;
57k) (S71C, 121Q, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21; 57l) (S71C, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21;
57m) (K56R, K59R, K69R, N121Q, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21;
57n) (K56R, K59R, K69R, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ala-FGF21;
57o) (S71C, 121Q, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21;
57p) (S71C, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21;
57q) (K56R, K59R, K69R, N121Q, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21;
57r) (K56R, K59R, K69R, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) Ser-FGF21;

57s) (S71C, 121Q, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21;

57t) (S71C, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21;

57u) (K56R, K59R, K69R, N121Q, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21;

57v) (K56R, K59R, K69R, K122R, P143V, A145E, L146E, 148aD, P149L, P150R, I152H, 153aE, 153bS, 153cD, 153dM, A154F, P155S, Q156S, P158L, D159E, V160T, G161D, S163M, L166F, S167G, M168L, 169aT, P171L, S172E, Q173A, G174V, Y179F, A180E, des181) FGF21;

Example 58

HEK293/Beta-Klotho Erk Phosphorylation Assay

Erk phosphorylation assay was performed in HEK293 cells that were stably transfected with human beta-Klotho. The HEK293T/b-klotho stable cells were seeded at 30000 cells/well on 96-well plates. After two days, fresh media was added, and after 2 hours more the FGF21 proteins were added. The plates were incubated for 12 minutes. And total ERK phosphorylation was assessed using an AlphaScreen SureFire Phospho-ERK1/2 Assay Kit (Perkin Elmer, Waltham, Mass.) according to the manufacturer's instructions and an EnVision Multilabel Microplate Reader Model 2103 (Perkin Elmer) with the AlphaScreen HTS Turbo option was used for signal detection. Data are represented as means+/−S.E.M. EC50 values were determined from a 4-parameter logistic nonlinear regression analysis using GraphPad Prism version 5.02. References: Yie, J. et al.: FGF21 N- and C-termini play different roles in receptor interaction and activation, *FEBS Letters* 583 (2009) 19-24, and Micanovic R. et al.: Different roles of N- and C-termini in the functional activity of FGF21. *J. Cell. Physiol.* 2009 May; 219(2):227-34.

TABLE 4

| | ERK | |
|---|---|---|
| Compound from example number | Compound | pERK-HEK293-Beta-klotho without HSA [EC50 (nM)] Median Value |
| 1 | A | 1.6 |
| 56h | | 2.0 |
| 51 | | 12 |

TABLE 4-continued

| | ERK | |
|---|---|---|
| Compound from example number | Compound | pERK-HEK293-Beta-klotho without HSA [EC50 (nM)] Median Value |
| 56n | | |
| 56m | | 3.3 |
| 56l | | 2.0 |
| 17 | | 3 |
| 2i | I | 2.1 |
| 56af | | 75.0 |
| 2p | J | 1.8 |
| 56as | | 44.0 |
| 56ae | | 36.0 |
| 56am | | 15.0 |
| 56ao | | 1.0 |
| 56c | | 29.0 |
| 47 | | 10.0 |
| 756a | V | 7.4 |
| 46 | | 3.9 |
| 53 | | 6.4 |
| 54 | | 4.2 |
| 56g | | 3.3 |
| 49 | | 1.2 |
| 48 | | 4.6 |
| 56ab | | 2.5 |
| 56k | | 1.8 |
| 56j | | 1.1 |
| 16 | | 1.4 |
| 56ag | | 1.4 |
| 15 | | 1.6 |
| 56r | | .7 |
| 2h | M | 1.7 |
| 56ar | | 1.2 |
| 56z | | 1.0 |
| 2a | B | n.t. |
| 4 | F | .9 |
| 56ac | | 9.5 |
| 56ad | | 17.0 |
| 56s | | 3.3 |
| 2o | | 1.0 |
| 56ai | | 100.0 |
| 21 | K | 1.4 |
| 56aj | | 100.0 |
| 2n | | 3.9 |
| 2m | | 5.9 |
| 56t | | 6.7 |
| 2i | N | 4.7 |
| 2k | Q | 2.2 |
| 2j | P | 1.0 |
| 7 | V | 1.4 |
| 2 | | 100.0 |
| 2e | E | 3.0 |
| 5 | H | 1.1 |
| 6 & 12 | O | 1.5 |
| 13 | | 4.8 |
| 14 | | 2.9 |
| 56aa | | 1.0 |
| 56ah | | 1.0 |
| 56al | | 100.0 |
| 56f | | 3.8 |
| 50 | | 2.0 |
| 56i | | 2.2 |
| 18 | | 2.5 |
| 56d | | 6.6 |
| 55 | | 2.0 |
| 52 | | 11 |
| 56ap | | 3 |
| 56y | | 12.0 |

The invention claimed is:

1. A derivative of an FGF21 compound having an albumin binder of the formula A-B-C-D-E- covalently attached to the FGF21 compound via a cysteine residue, the N-terminal amino acid residue, or the epsilon-amino group of a lysine residue, wherein said FGF21 compound has an identity of at least 80% to SEQ ID NO:1, wherein A- is an element selected from formula I, wherein n is 14 or 16, and formula II, wherein n is 13:

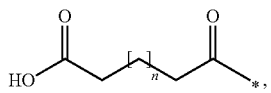
(formula I)

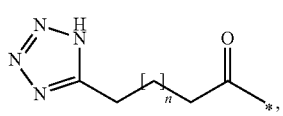
(formula II)

and * is the point of attachment to -B-;
-B- is selected from -B1-, -B2- or -B1-B2-, wherein
-B1- is an element of formula IV:

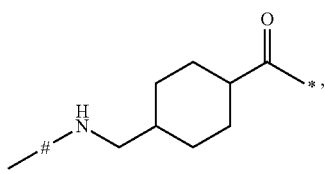
(formula IV or Trx)

wherein * is the point of attachment to -B2- or -C-, and # is the point of attachment to A;
-B2- is an element selected from formula IIX, IX and XVIII:

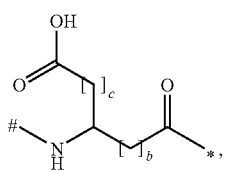
(formula IIX)

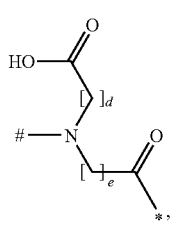
(formula IX)

—NH—SO$_2$—(CH$_2$)$_u$—CO—*    (formula XXVIII), wherein b is 2, c is 0, d is 1, e is 2, u is 3 and * is the point of attachment to -C-, -D-, E- or the FGF21 compound, and # is the point of attachment to A- or -B1-;

-C- is absent, or is an element of formula X:

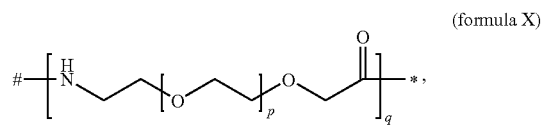
(formula X)

wherein p is 1, q is 1 or 2, * is the point of attachment to -D-, -E- or the FGF21 compound, and # is the point of attachment to -B-;

-D- is absent, or is an element selected from formula XII and XIII:

—NH—(CH$_2$)$_r$—NH—CO—(CH$_2$)$_s$—*    (formula XII),

—NH—(CH$_2$)$_t$—*    (formula XIII), wherein r is 2, s is 1 or 2, t is 2, * is the point of attachment to -E- or the FGF21 compound, and # is the point of attachment to -C-, or -B-;

-E- is absent or is an element of formula XXII, XXIV, XXV, and XXVI:

(formula XXII)

(formula XXIV)

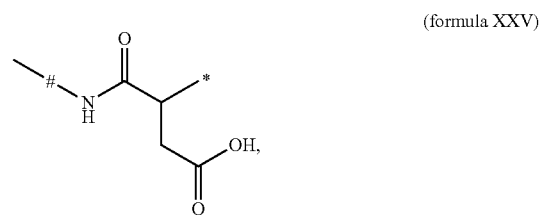
(formula XXV)

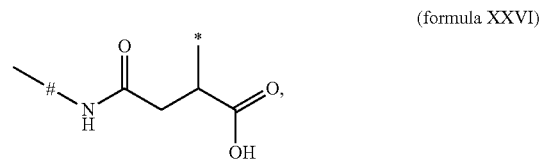
(formula XXVI)

wherein * is the point of attachment to the FGF21 compound, and # is the point of attachment to -D-, -C- or -B-;

or a pharmaceutically acceptable salt thereof.

2. The derivative of claim 1, wherein the albumin binder is selected from the group consisting of:

161 162
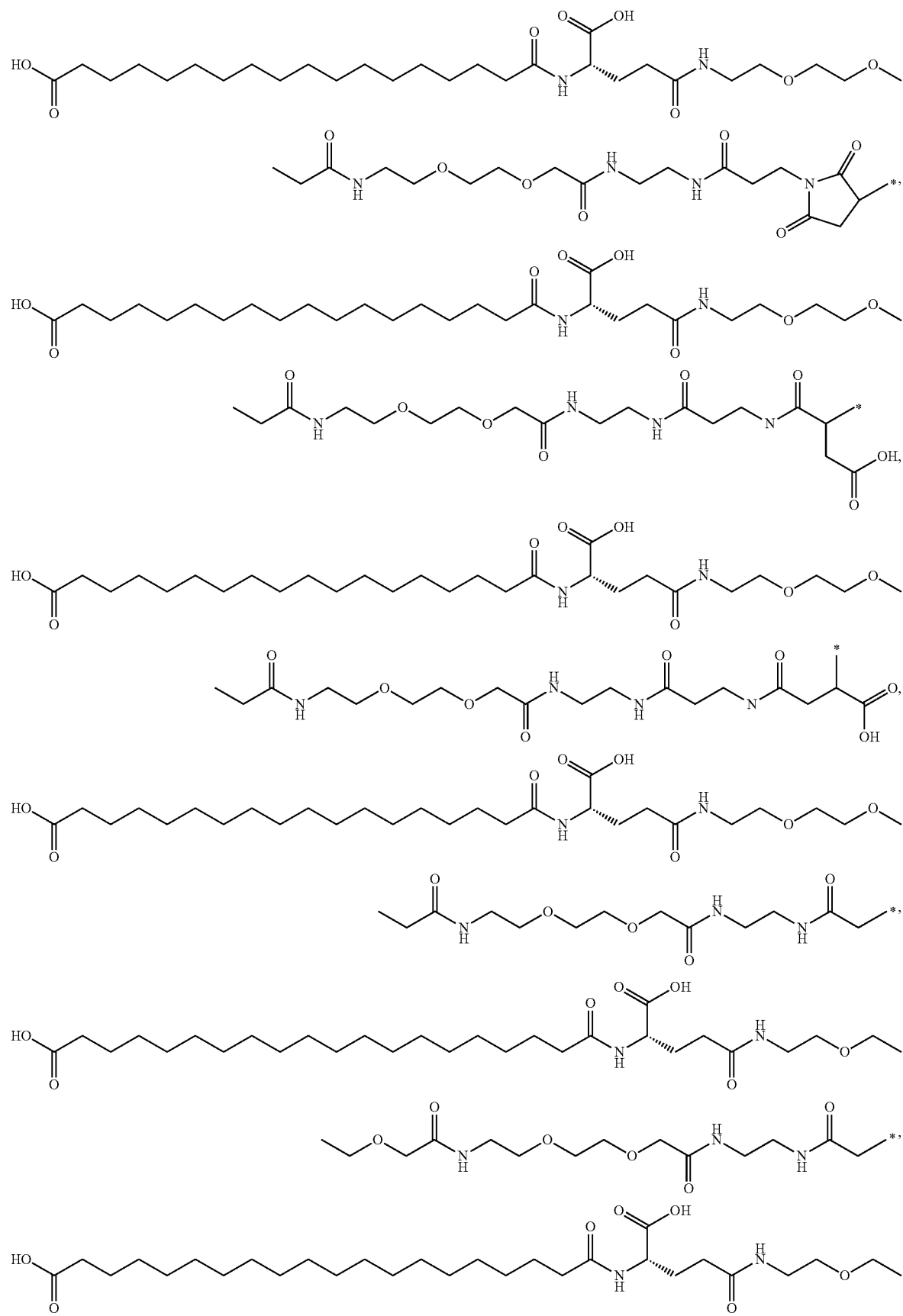

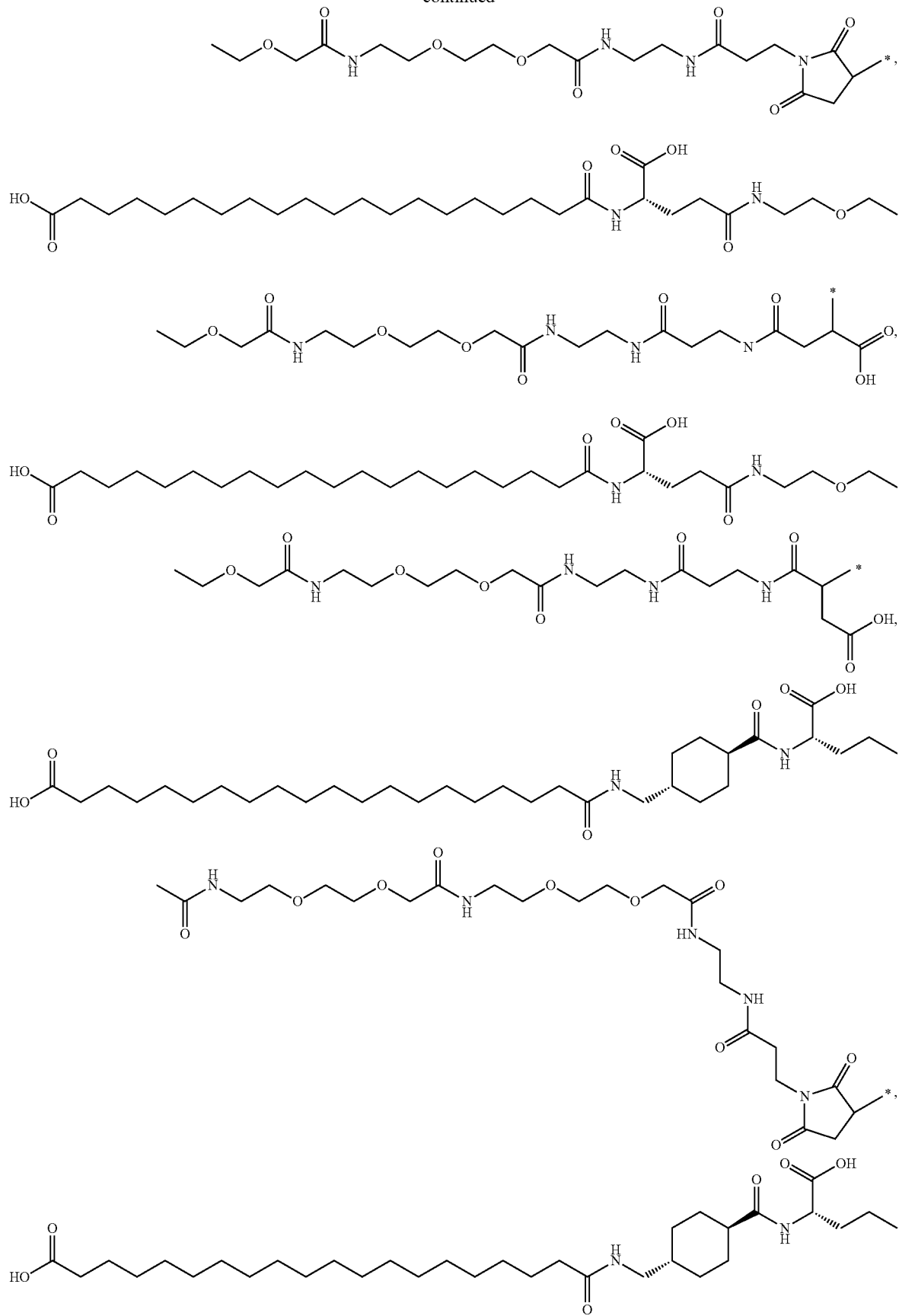

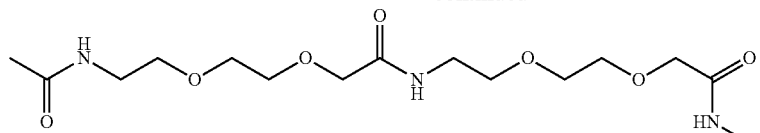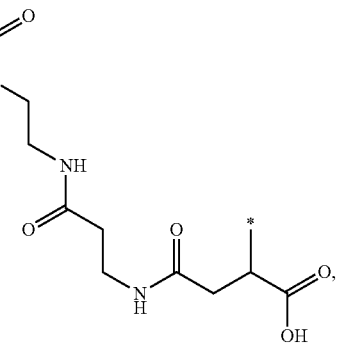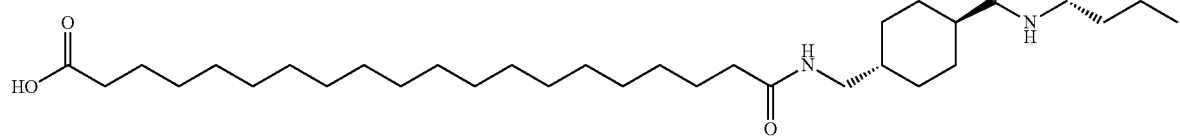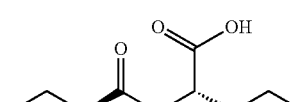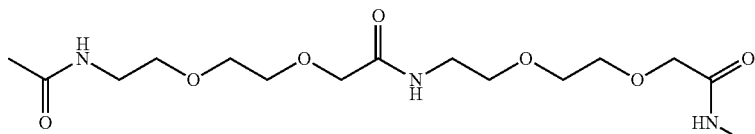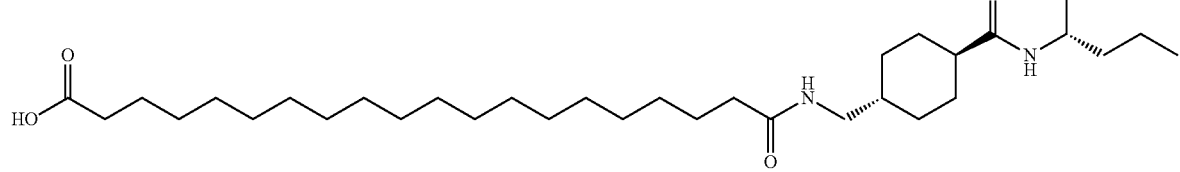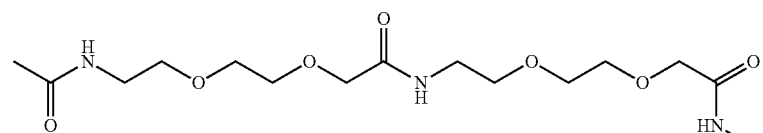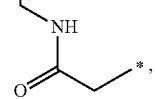

-continued
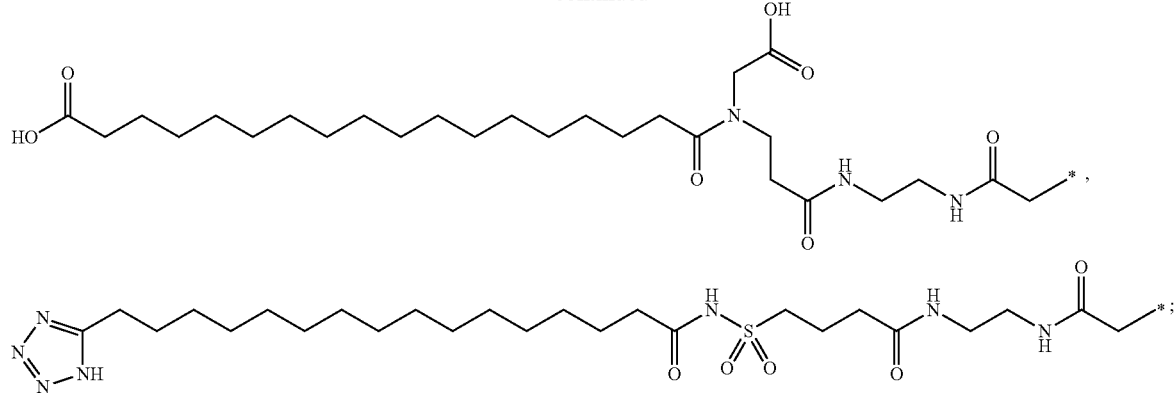
or a pharmaceutically acceptable salt of any one of the corresponding derivatives.
3. The derivative of claim 1, wherein the attachment of the albumin binder takes place via the thiol group of a cysteine residue.
4. The derivative of claim 1, wherein the albumin binder is selected from the group consisting of:
(15):
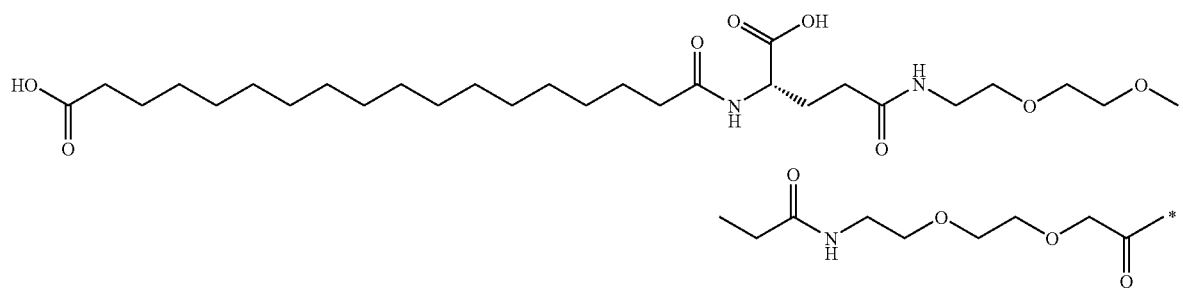
(16):
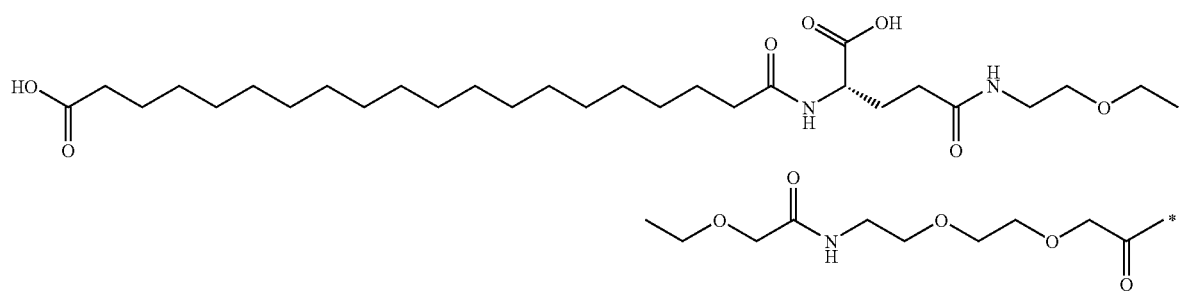
(17):
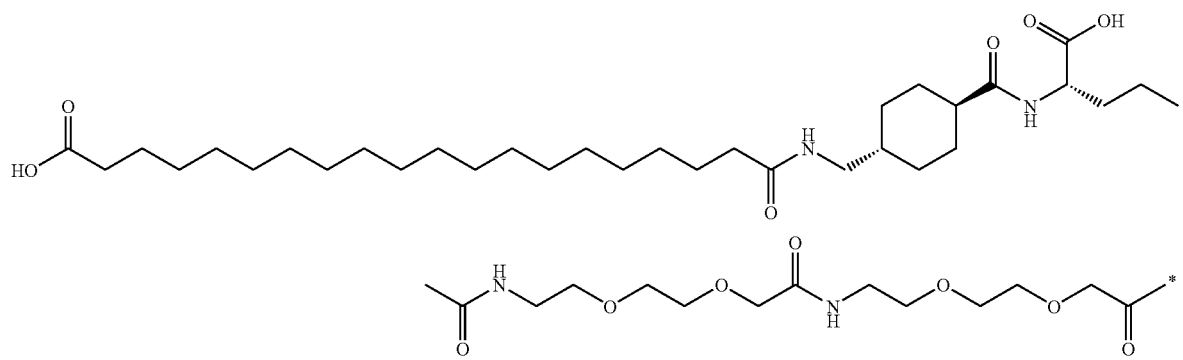

(18):

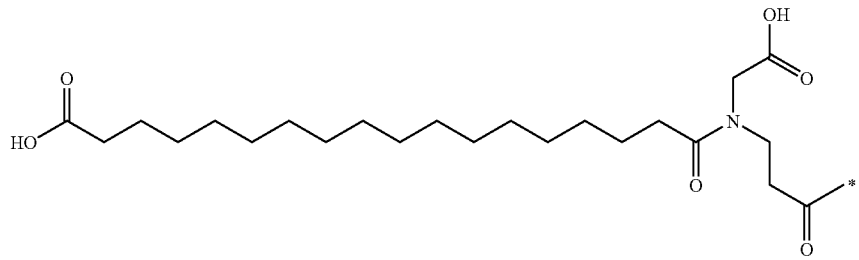

(19):

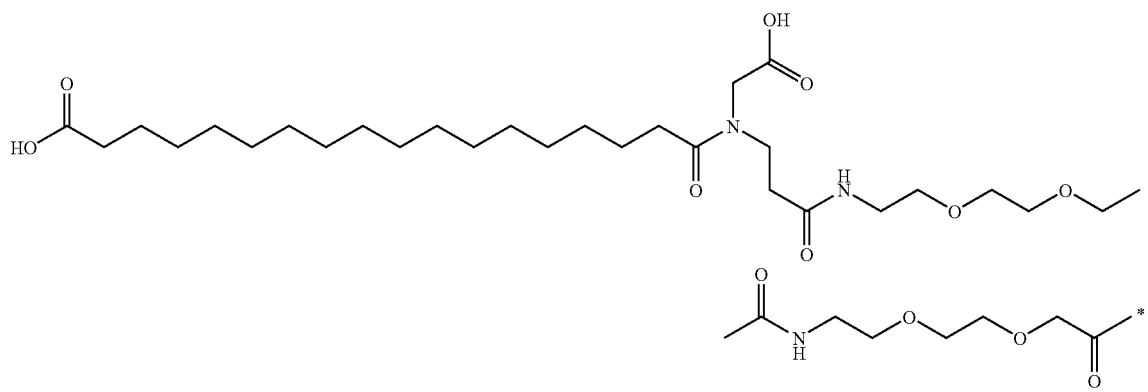

(20):

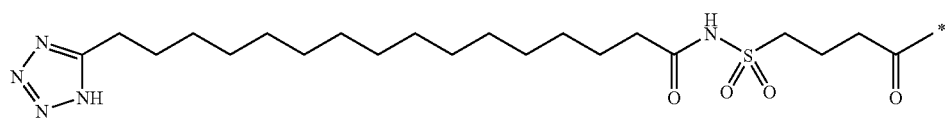

(21):

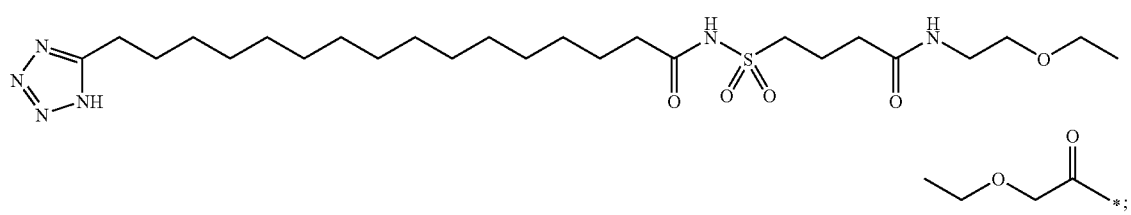

or a pharmaceutically acceptable salt of any of the corresponding derivatives.

5. The derivative of claim 1, wherein the attachment of the albumin binder takes place via the amino group of the N-terminal amino acid residue.

6. The derivative of claim 1, wherein the attachment of the albumin binder takes place via the epsilon amino group of a lysine residue selected from positions 56, 59, 69 and 122 of the FGF21 compound numbered according to SEQ ID NO:1.

7. The derivative of claim 1, wherein the FGF21 compound has an identity of at least 95% to SEQ ID NO: 1.

8. A composition comprising the derivative of claim 1, and a pharmaceutically acceptable carrier.

9. A derivative of an FGF21 compound having an albumin binder of the formula A-B-C-D-E- covalently attached to the FGF21 compound via a cysteine residue, the N-terminal amino acid residue, or the epsilon-amino group of a lysine residue, wherein said FGF21 compound has an identity of at least 80% to SEQ ID NO:1, wherein A- is an element selected from formula I, wherein n is 14 or 16, and formula II, wherein n is 13:

(formula I)

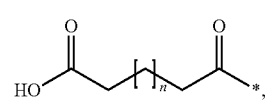

(formula II)

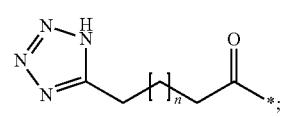

and * is the point of attachment to -B-;

-B- is absent, or is -B2- wherein

-B2- is an element selected from formula IIX, IX and XVIII:

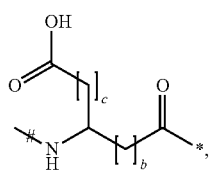
(formula IIX)

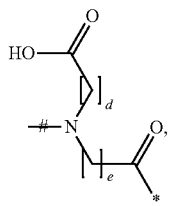
(formula IX)

—NH—SO$_2$-(CH$_2$)$_u$—CO—*  (formula XXVIII)

wherein b is 2, c is 0, d is 1, e is 2, u is 3, and * is the point of attachment to -C-, -D-, -E- or the FGF21 compound, and # is the point of attachment to A-;

-C- is absent, or is an element of formula X:

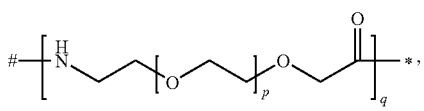
(formula X)

wherein p is 1, q is 1 or 2, * is the point of attachment to -D-, -E- or the FGF21 compound, and # is the point of attachment to -B- or -A-;

-D- is absent, or is an element selected from formula XII and XIII:

—NH—(CH$_2$)$_r$—NH—CO—(CH$_2$)$_s$—*  (formula XII),

—NH—(CH$_2$)$_t$-*  (formula XIII), wherein r is 2, s is 1 or 2, t is 2, * is the point of attachment to -E- or the FGF21 compound, and # is the point of attachment to -C- or -B-;

-E- is absent, or is an element selected from formula XXII and XXIV:

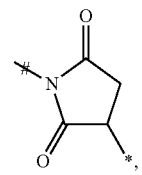
(formula XXII)

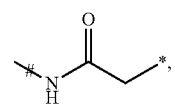
(formula XXIV)

wherein * is the point of attachment to the FGF21 compound, and # is the point of attachment to -D-, -C-, or -B-;

or a pharmaceutically acceptable salt thereof.

10. The derivative of claim 9, wherein the albumin binder is selected from the group consisting of the following formulas:

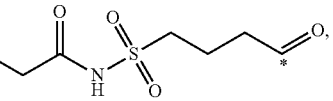

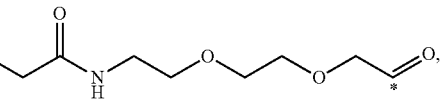

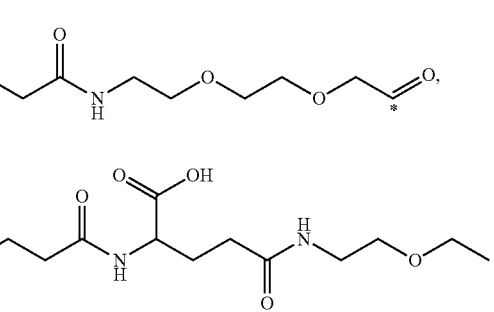

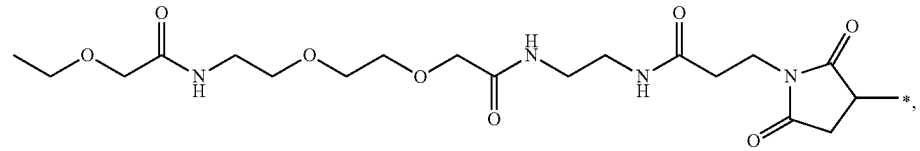

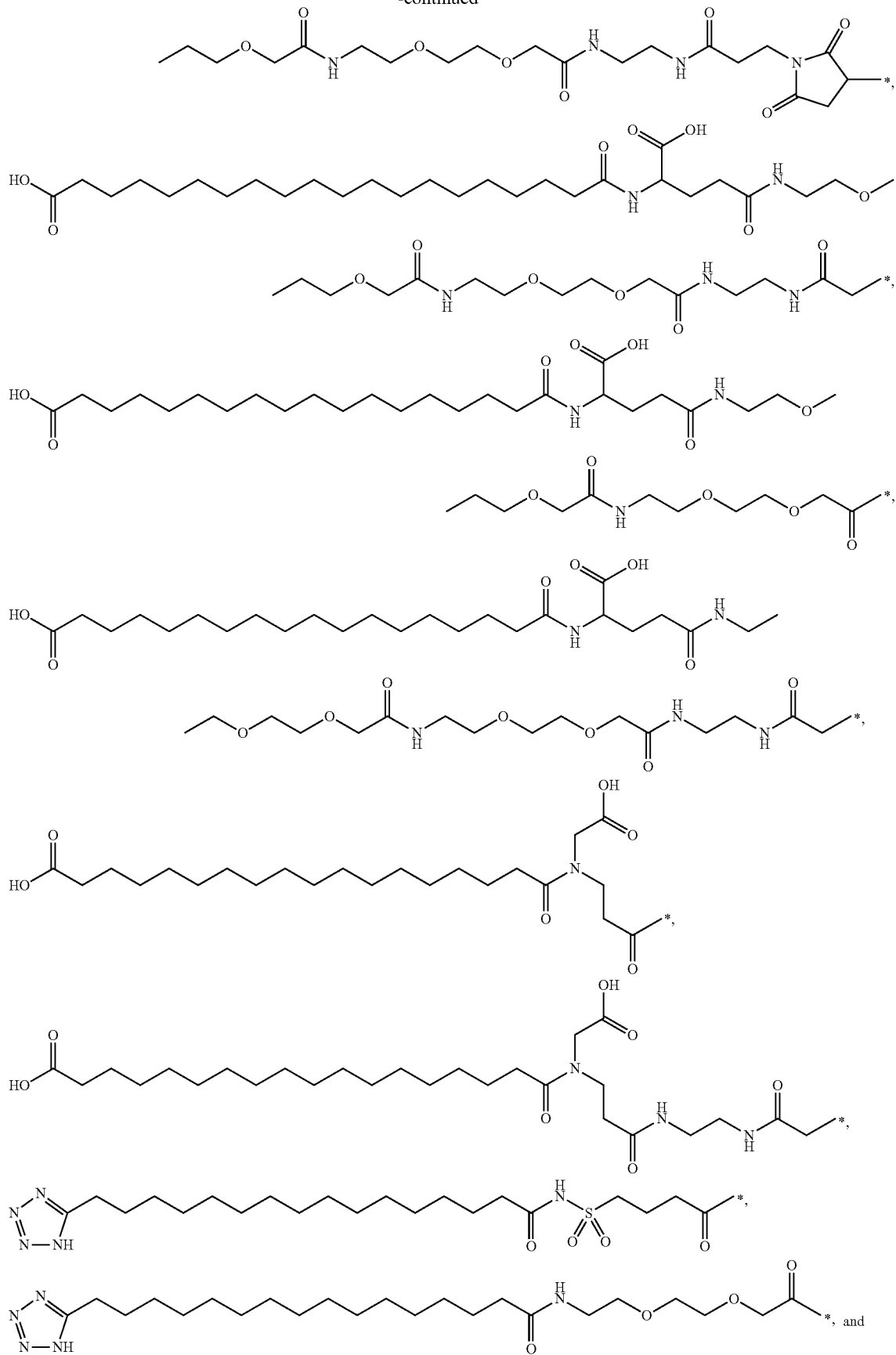

-continued
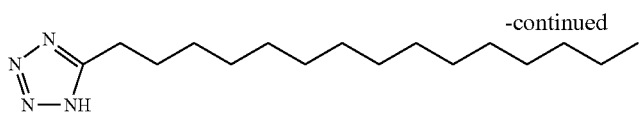
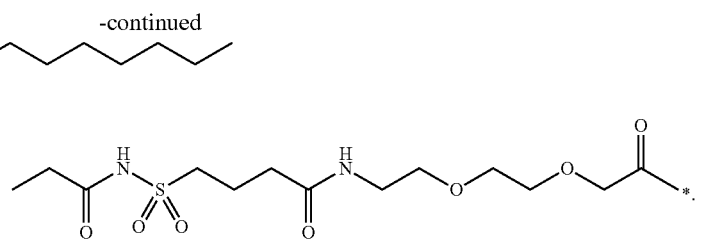
* * * * *

SEQUENCE LISTING

<160> NUMBER OF SEQ ID NOS: 2

<210> SEQ ID NO 1

```
<211> LENGTH: 181
<212> TYPE: PRT
<213> ORGANISM: Homo sapiens
<220> FEATURE:
<221> NAME/KEY: mat_peptide
<222> LOCATION: (1)..(181)
<220> FEATURE:
<221> NAME/KEY: DISULFID
<222> LOCATION: (75)..(93)

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 28
<212> TYPE: PRT
<213> ORGANISM: Homo sapiens
<220> FEATURE:
<221> NAME/KEY: SIGNAL
<222> LOCATION: (1)..(28)

<400> SEQUENCE: 2

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala
            20                  25
```